United States Patent
Venditti et al.

(10) Patent No.: US 11,372,004 B2
(45) Date of Patent: Jun. 28, 2022

(54) BIOMARKERS OF ORGANIC ACIDEMIAS

(71) Applicant: The United States of America, as represented by the Secretary, Department of Health and Human Services, Bethesda, MD (US)

(72) Inventors: Charles P. Venditti, Potomac, MD (US); Irini Manoli, Bethesda, MD (US)

(73) Assignee: The United States of America, as represented by the Secretary Department of Health and Human Services, Bethesda, MD (US)

( * ) Notice: Subject to any disclaimer, the term of this patent is extended or adjusted under 35 U.S.C. 154(b) by 0 days.

(21) Appl. No.: 16/641,994

(22) PCT Filed: Sep. 6, 2018

(86) PCT No.: PCT/US2018/049757
§ 371 (c)(1),
(2) Date: Feb. 25, 2020

(87) PCT Pub. No.: WO2019/051092
PCT Pub. Date: Mar. 14, 2019

(65) Prior Publication Data
US 2020/0217856 A1 Jul. 9, 2020

Related U.S. Application Data

(60) Provisional application No. 62/556,071, filed on Sep. 8, 2017.

(51) Int. Cl.
| | | |
|---|---|---|
| *G01N 33/68* | (2006.01) | |
| *G01N 33/50* | (2006.01) | |
| *G01N 33/74* | (2006.01) | |

(52) U.S. Cl.
CPC ..... *G01N 33/6893* (2013.01); *G01N 33/5008* (2013.01); *G01N 33/74* (2013.01); *G01N 2333/50* (2013.01); *G01N 2800/04* (2013.01); *G01N 2800/52* (2013.01)

(58) Field of Classification Search
CPC ........... G01N 33/6893; G01N 33/5008; G01N 33/74; G01N 2333/50; G01N 2800/04; G01N 2800/52; C12Q 2600/158
See application file for complete search history.

(56) References Cited

U.S. PATENT DOCUMENTS

2016/0033522 A1* 2/2016 Al-Dirbashi ........... G01N 33/94
436/129
2018/0271795 A1* 9/2018 Martini ..................... A61P 3/00

FOREIGN PATENT DOCUMENTS

| CN | 103601805 | 8/2015 |
| WO | WO 2019/051092 | 3/2019 |
| WO | WO 2019/089799 | 5/2019 |

OTHER PUBLICATIONS

Mayeux J. American Soc. Experimental NeuroTherapeutics 2004 vol. 1: 182-188 (Year: 2004).*
Kavanaugh et al. Future Rheumatol. 2008 3: 303-305 (Year: 2008).*
Tavel Curr Opin HIV AIDS 2010 5: 463-466 (Year: 2010).*
Atkuri et al. PNAS 2009 106: 3941-45 (Year: 2009).*
Perito et al. (Liver Transpl. 2014 20: doi: 10.1002/lt.23765; Total 18 pages). (Year: 2014).*
Enns et al., (2017) Journal of Clinical Medicine 6(50):1-17 "Glutathione as a Redox Biomarker in Mitochondrial Disease—Implications for Therapy".
Fisher et al., (2011) Endocrinology 152(8):2996-3004 "Integrated Regulation of Hepatic Metabolism by Fibroblast Growth Factor 21 (FGF21) in vivo".
International Search Report and Written Opinion dated Apr. 30, 2019 for PCT/US2018/049757.
International Search Report and Written Opinion dated Jan. 30, 2019 for PCT/US2018/058515.
Kirmse et al., (2017) Mol. Gen and Metabolism Reports 13:52-54 "Plasma Fibroblast Growth Factor-21 Levels in Patients With Inborn Errors of Metabolism".
Kolker et al., (2011) J Inhert. Metab. Dis. 34:677-694 "Diagnosis and Management of Glutaric Aciduria Type I—Revised Recommendations".
Lehtonen et al., (2016) Neurology 87:2291-2299 "FGF21 is a Biomarker for Mitochondrial Translation and mtDNA Maintenance Disorders".
Molema et al., (2018) J. Inherit. Metab. Dis. 41:1179-1187 "Fibroblast Growth Factor 21 as a Biomarker for Long-term Complications in Organic Acidemias".
Parikh et al., (2014) Genetics in Medicine 1-13 "Diagnosis and Management of Mitochondrial Disease: a Consensus Statement Form the Mitochondrial Medicine Society".
Schwartz et al., (2008) Jornal de Pediatria 8-19 "Treatment of Inborn Errors of Metabolism".
Shennar et al., (2015) Qatar Medical Journal 9:1-6 "Diagnosis and Clinical Features of Organic Acidemias: A Hospital-based Study in a Single Center in Damascus, Syria".
International Preliminary Report on Patentability for PCT/US2018/049757 dated Mar. 10, 2020, 16 pages.

* cited by examiner

Primary Examiner — Changhwa J Cheu
(74) Attorney, Agent, or Firm — Leydig, Voit & Mayer, Ltd.

(57) ABSTRACT

Methods of using biomarkers in determining the efficacy of a treatment for an organic acidemia in a subject are disclosed herein. Methods of using biomarkers in determining the efficacy of a liver-directed treatment for an organic acidemia in a subject are likewise disclosed herein.

20 Claims, 29 Drawing Sheets
Specification includes a Sequence Listing.

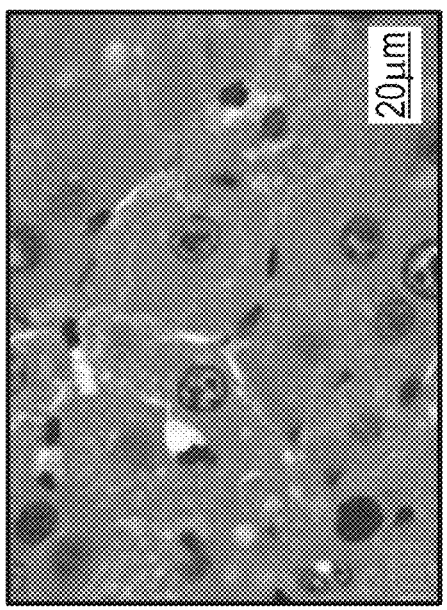
FIG. 2A
$Mut^{-/-}$;TgINS-MCK-*Mut*
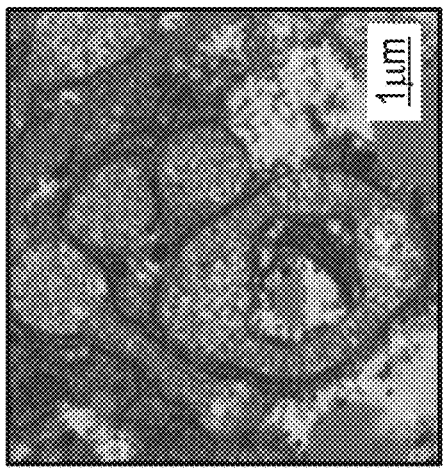
FIG. 2B
$Mut^{-/-}$;TgINS-MCK-*Mut*
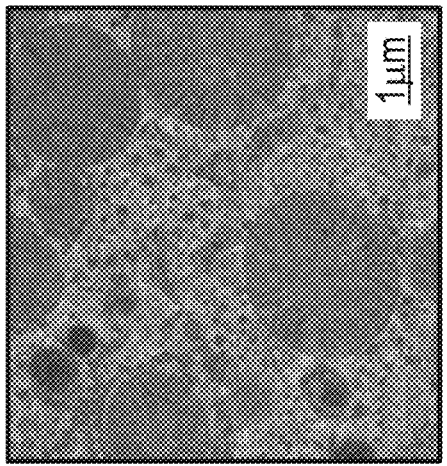
FIG. 2C
$Mut^{+/-}$;TgINS-MCK-*Mut*
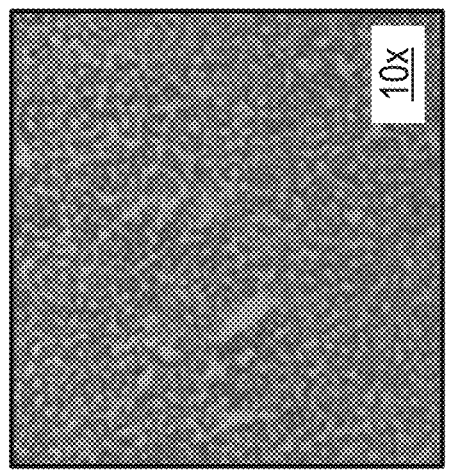
FIG. 3A
$Mut^{+/-}$;TgINS-MCK-*Mut*
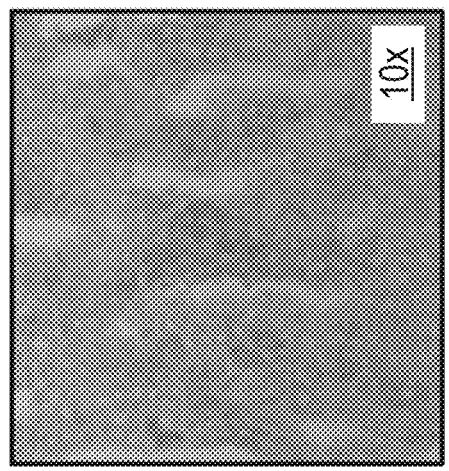
$Mut^{-/-}$;TgINS-MCK-*Mut*

$Mut^{-/-}$;Tg$^{INS-MCK-Mut}$ $Mut^{-/-}$;Tg$^{INS-MCK-Mut}$ $Mut^{+/-}$;Tg$^{INS-MCK-Mut}$

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Synthetic primer

<400> SEQUENCE: 1
ccattctggg aaggcttcta                                            20

<210> SEQ ID NO 2
<211> LENGTH: 21
<212> TYPE: DNA
<213> ORGANISM: Artificial Sequence
<220> FEATURE:
<223> OTHER INFORMATION: Synthetic primer

<400> SEQUENCE: 2
tgcacagagt gctagtttcc a                                          21

<210> SEQ ID NO 3
<211> LENGTH: 20
<212> TYPE: DNA
<213> ORGANISM: Artificial Sequence
<220> FEATURE:
<223> OTHER INFORMATION: Synthetic Primer

<400> SEQUENCE: 3
catgttgaga gctaagaatc                                            20

<210> SEQ ID NO 4
<211> LENGTH: 20
<212> TYPE: DNA
<213> ORGANISM: Artificial Sequence
<220> FEATURE:
<223> OTHER INFORMATION: Synthetic primer

<400> SEQUENCE: 4
tagaagttca ttccaatccc                                            20
```

BIOMARKERS OF ORGANIC ACIDEMIAS

RELATED APPLICATIONS

Priority Data

This application is a 35 U.S.C. § 371 national phase application of PCT/US2018/049757 (WO2019/051092), filed on Sep. 6, 2018, entitled "Biomarkers Of Organic Acidemias", which application claims priority to and the benefit of U.S. Provisional Application No. 62/556,071, filed Sep. 8, 2017, the disclosures of which are incorporated herein by reference in their entirety.

STATEMENT OF GOVERNMENT INTEREST

This invention was made with Government support under project number HG-200318-11 by the National Institutes of Health, National Human Genome Research Institute. The Government has certain rights in the invention.

SEQUENCE STATEMENT

Incorporated by reference herein in its entirety is the Sequence Listing entitled "Sequence_listing" created Jan. 10, 2019, size of 1.14 kilobytes.

FIELD

The present disclosure relates, in general, to methods of using biomarkers in determining organic acidemia activity, and more particularly, to methods of using biomarkers in determining the efficacy of a treatment, for example, a liver-directed treatment for an organic acidemia

BACKGROUND

Methylmalonic acidemia ("MMA") is an autosomal recessive disorder caused by defects in the mitochondrial localized enzyme methylmalonyl-CoA mutase (MUT). The estimated incidence of MMA is 1 in 25,000-48,000. MUT is an enzyme that catalyzes the conversion of L-methylmalonyl-CoA to succinyl-CoA. This reaction is one of several enzymatic reactions required to metabolize branch chain amino acids, odd chain fatty acids, cholesterol, and propionate produced by the gut flora (Chandler, et al. 2005 *Mol Genet Metab* 86:34-43). MUT deficiency, the most common cause of isolated MMA, is characterized by the accumulation of methylmalonic acid and other disease-related metabolites (Manoli and Venditti, Genereviews). The disease is managed by dietary restriction of amino acid precursors and cofactors, but lacks definitive therapy. MMA is associated with metabolic instability, seizures, pancreatitis, strokes, and kidney failure, and it can be lethal, even when patients are being properly managed, underscoring the need for new therapies for this disease.

MMA treatments include, but are not limited to, dietary restrictions, liver transplantation, combined liver and kidney transplantation, and liver-directed gene therapy.

The MUT enzyme requires adenosylcobalamin (Ado-Cbl) as coenzyme. Therefore, methylmalonic acid metabolism is inevitably linked to vitamin B12 (cobalamin), its adequate intake and correct uptake, transport, and intracellular metabolism. The cblA, cblB, and variant 2 form of cblD complementation groups are linked to processes unique to Ado-Cbl synthesis. The cblC, cblD, cblF, cblJ complementation groups are associated with defective methyl-cobalamin synthesis, as well. Combined MMA and homocystinuria, cobalamin C (cblC) type, is the most common disorder of cobalamin metabolism. (Carrillo et al. GeneReviews 2013, Disorders of Intracellular Cobalamin Metabolism.) CblC typically presents in the neonatal period with neurological deterioration, failure to thrive, cytopenias, and multisystem pathology including renal and hepatic dysfunction. (Weisfeld-Adams et al. Mol Genet Metab. 2010 February; 99(2): 116-123.)

The related disorder, propionic acidemia ("PA"), is an autosomal recessive disorder caused by defects in propionyl CoA carboxylase ("PCC") of either the propionyl CoA carboxylase alpha (PCCA) or beta subunits (PCCB). PCC is inactive in affected individuals with either PCCA or PCCB deficiency. Patients with PA cannot metabolize branch chain amino acids, odd chain fatty acids, cholesterol, and propionate produced by the gut flora (Schechlechov and Venditti, Genereviews). The condition leads to an abnormal buildup of particular acids known as organic acids such as propionic acid, 2-methylcitric acid, and 3-hydroxypropionic acid. As a result, a substance called propionyl-CoA and other potentially harmful compounds can accumulate to toxic levels in the body. This accumulation damages the brain, nervous system and heart, causing the serious health problems associated with PA. The disease is managed by dietary restriction of amino acid precursors and cofactors, but lacks definitive therapy. PA is associated with metabolic instability, seizures, pancreatitis, strokes, and a propensity to develop hyperammonemia. Like MMA, PA can be lethal, even when patients are being properly managed, underscoring the need for new therapies for this disease.

PA treatments include, but are not limited to, dietary restrictions, liver transplantation, and liver-directed gene therapy.

There are needs to develop better therapies and better methods for determining the efficacy of therapies for MMA, PA, cobalamin metabolic disorders and other organic acidemias in a subject.

BRIEF SUMMARY

Methods of determining efficacy of a treatment for an organic acidemia in a subject are provided. In one aspect, the organic acidemia is MMA or PA. In another aspect, the treatment is liver-directed treatment. Methods of determining the effects of hepatic mitochondrial dysfunction in patients suffering from an organic acidemia are provided.

In one aspect, the invention provides a method for determining the efficacy of a treatment for an organic acidemia in a subject. The method includes the steps of detecting the level of a biomarker or biomarkers in a biological sample from the subject prior to the treatment, wherein the biomarker comprises an FGF21 gene expression product or a GDF15 gene expression product, or both. The method further comprises the step of detecting the level of the biomarker or biomarkers in a biological sample from the subject after the treatment, wherein a decrease in the level of the biomarker after the treatment compared to the level of the biomarker or biomarkers prior to the treatment indicates efficacy of the treatment.

In another aspect, the invention provides a method for determining efficacy of a treatment for an organic acidemia in a subject. The method comprises the step of detecting the level of a biomarker or biomarkers in a biological sample from the subject after the treatment, wherein a decrease in the level of the biomarker compared to a predetermined standard level indicates efficacy of the treatment, wherein the biomarker comprises an FGF21 gene expression product, a GDF15 gene expression product, or both.

In some embodiments, the invention provides a method of treating a subject for an organic acidemia. The method comprises the steps of detecting the level of a biomarker or biomarkers in a biological sample from the subject prior to the treatment, wherein the biomarker comprises an FGF21 gene expression product or a GDF15 gene expression product, or both. The method further comprises the step of administering a treatment to the subject to improve compromised hepatic enzyme activity associated with the organic acidemia. In certain embodiments, the enzyme is MUT or PCC. The method further comprises the step of detecting the level of the biomarker in a biological sample from the subject after the treatment, wherein a decrease in the level of biomarker after the treatment compared to the level of the biomarker prior to the treatment indicates efficacy of the treatment. In one aspect, the invention further comprises the steps of discontinuing, altering, or continuing the treatment based on the level after treatment compared to the level before the treatment.

In one aspect, the invention provides a method for improving hepatic enzyme activity in a subject having an organic acidemia. The method comprises detecting the level of a biomarker or biomarkers in a biological sample from the subject prior to treatment, wherein the biomarker is a fibroblast growth factor 21 (FGF21) gene expression product or a growth differentiation factor 15 (GDF15) gene expression product, or both. The method further comprises the step of administering a treatment to the subject to improve compromised hepatic enzyme activity associated with the organic acidemia. The method further comprises detecting the level of the biomarker in a biological sample from the subject after the treatment. The method further comprises the step of discontinuing, altering, or continuing the treatment based on the level after treatment compared to the level before treatment.

In another aspect, the invention provides a method for diagnosing hepatic mitochondrial dysfunction in a subject suffering from an organic acidemia. The method comprises detecting the level of a biomarker or biomarkers in a biological sample from the subject, wherein the biomarker is a fibroblast growth factor 21 (FGF21) gene expression product or a growth differentiation factor 15 (GDF15) gene expression product, or both; wherein an increase in the level of the biomarker compared to a predetermined standard level indicates that the subject is suffering from hepatic mitochondrial dysfunction.

In another aspect, the invention provides a method for determining the efficacy of a treatment for an organic acidemia in a subject. The method comprises the step of detecting the level of a biomarker or biomarkers in a biological sample obtained from the subject prior to the treatment, wherein the biomarker or biomarkers is selected from the group consisting of Gadd45b, Gstm3, Pdk4, Rragd, Slc7A11, Asns, Abcc4, Fasn, and Hsd3b2 gene expression product. The method further comprises the step of detecting the level of the biomarker or biomarkers in a biological sample from the subject after the treatment. In certain embodiments, a decrease in the level of the biomarker or biomarkers after the treatment compared to the level of the biomarker or biomarkers prior to the treatment indicates efficacy of the treatment.

In yet another aspect, the invention provides kits for treating or diagnosing an organic acidemia. In this embodiment, the kit comprises an antibody that specifically recognizes a protein selected from the group consisting of FGF21, GDF15, Gadd45b, Gstm3, Pdk4, Rragd, Slc7A11, Asns, Abcc4, Fasn, and Hsd3b2, guidance for testing before, during, and/or after treatment, and guidance for interpreting the test result. In another embodiment, the kit comprises DNA that recognizes mRNA that expresses a protein selected from the group consisting of FGF21, GDF15, Gadd45b, Gstm3, Pdk4, Rragd, Slc7A11, Asns, Abcc4, Fasn, and Hsd3b2, guidance for testing before, during, and/or after treatment, and guidance for interpreting the test results.

The following numbered paragraphs describe further aspects of the present invention:

1. A method for determining the efficacy of a treatment for an organic acidemia in a subject, the method comprising: detecting the level of a biomarker or biomarkers in a biological sample from the subject prior to the treatment, wherein the biomarker or biomarkers is a fibroblast growth factor 21 (FGF21) gene expression product or a growth differentiation factor 15 (GDF15) gene expression product, or both; and detecting the level of the biomarker or biomarkers in a biological sample from the subject after the treatment;

wherein a decrease in the level of the biomarker or biomarkers after the treatment compared to the level of the biomarker or biomarkers prior to the treatment indicates efficacy of the treatment.

2. The method of claim 1, wherein the biomarker is a FGF21 gene expression product.

3. The method of claim 1, wherein the biomarker is a GDF15 gene expression product.

4. The method of claim 1, wherein the biomarker or biomarkers comprises both a FGF21 gene expression product and a GDF15 gene expression product.

5. The method of claim 1, wherein the biomarker is a protein.

6. The method of claim 1, wherein the biomarker is detected at the nucleic acid level.

7. The method of claim 1, wherein the biological sample is a serum sample.

8. The method of claim 1, wherein the biological sample is a plasma sample.

9. The method of claim 1, wherein the treatment is a liver-directed treatment.

10. The method of claim 1, wherein the treatment comprises administering a liver-directed gene transfer vector to the subject.

11. The method of claim 1, wherein the treatment is selected from the group consisting of gene therapy, mRNA therapy, cell therapy, small molecule, enzyme specific chaperonins, engineered microbes/microbiome, enzyme replacement therapy, and genome editing therapies.

12. The method of claim 1, wherein the organic acidemia is selected from the group consisting of all forms of methylmalonic acidemia (MMA), all forms of propionic acidemia (PA), isovaleric acidemia, glutaric aciduria type 1 (GA1), beta-ketothiolase deficiency (BKT), 3-methylcrotonyl-CoA carboxylase deficiency (3-MCC), 3-hydroxy-3-methylglutaryl-CoA lyase deficiency (HMG), 3-Methylglutaconic acidemia or 3-Methylglutaconyl-CoA Hydratase Deficiency (MGA), D-2 Hydroxyglutaric Aciduria (D2-HGA), Isobutyryl-CoA Dehydrogenase Deficiency 3-Hydroxyisobutyric aciduria (ICBD), L-2-Hydroxy-glutariscaciduria (L2HGA), Malonyl-CoA Decarboxylase Deficiency aka Malonic Acidemia (MA), Multiple carboxylase deficiency (MCD, holocarboxylase synthetase), and 3-Hydroxyisobutyryl-CoA Hydrolase Deficiency (HIBCH).

13. The method of claim 1, wherein the organic acidemia is methylmalonic acidemia or propionic acidemia.

14. The method of claim 1, wherein the organic acidemia is a disorder of propionate metabolism or a cobalamin metabolic and transport disorder causing MUT deficiency.

15. The method of claim 14, wherein the disorder of propionate metabolism is caused by isolated methylmalonyl-CoA mutase (MUT) deficiency, MMAA, MMAB, MMADHC, or cblA, cblB, cblD variant 2 classes of MMA.

16. The method of claim 14, wherein the cobalamin metabolic and transport disorders is selected from the group consisting of MMACHC, MMADHC, LMBRD1, ABCD4, TC2, CD320, AMN, cblC, cblD, cblF, cblJ, TC2, TCBLR and Imerslund-Graesbeck forms of combined MMAemia-hyperhomocysteinemia.

17. The method of claim 1, wherein the treatment is liver transplantation or combined liver and kidney transplantation.

18. A method of treating a subject for an organic acidemia, the method comprising:
detecting the level of a biomarker or biomarkers in a biological sample from the subject prior to treatment, wherein the biomarker is a fibroblast growth factor 21 (FGF21) gene expression product or a growth differentiation factor 15 (GDF15) gene expression product, or both;
administering a treatment to the subject to improve compromised hepatic enzyme activity associated with the organic acidemia;
detecting the level of the biomarker or biomarkers in a biological sample from the subject after the treatment; and
discontinuing, altering, or continuing the treatment based on the level after treatment compared to the level before treatment.

19. A method for determining efficacy of a treatment for an organic acidemia in a subject, the method comprising:
detecting the level of a biomarker or biomarkers in a biological sample from the subject after the treatment, wherein a decrease in the level of the biomarker compared to a predetermined standard level indicates efficacy of the treatment, wherein the biomarker or biomarkers is a fibroblast growth factor 21 (FGF21) gene expression product, a growth differentiation factor 15 (GDF15) gene expression product, or both.

20. A method for improving hepatic enzyme activity in a subject having an organic acidemia, the method comprising:
detecting the level of a biomarker or biomarkers in a biological sample from the subject prior to treatment, wherein the biomarker or biomarkers is a fibroblast growth factor 21 (FGF21) gene expression product or a growth differentiation factor 15 (GDF15) gene expression product, or both;
administering a treatment to the subject to improve compromised hepatic enzyme activity associated with the organic acidemia;
detecting the level of the biomarker or biomarkers in a biological sample from the subject after the treatment; and
discontinuing, altering, or continuing the treatment based on the level after treatment compared to the level before treatment.

21. The method of claim 20, where in the enzyme is selected from the group consisting of methylmalonyl-CoA mutase, propionyl CoA carboxylase, isovaleryl-CoA dehydrogenase, Glutaryl CoA Dehydrogenase, beta-ketothiolase, 3-methylcrotonyl-CoA carboxylase, 3-hydroxy-3-methylglutaryl-CoA lyase, 3-Methylglutaconyl-CoA Hydratase, Isobutyryl-CoA Dehydrogenase, Malonyl-CoA Decarboxylase, Multiple carboxylase, and 3-Hydroxyisobutyryl-CoA Hydrolase.

22. A method of treating a subject for an organic acidemia, the method comprising:
detecting the level of a biomarker or biomarkers in a first biological sample from the subject, wherein the biomarker is a fibroblast growth factor 21 (FGF21) gene expression product or a growth differentiation factor 15 (GDF15) gene expression product, or both; and
detecting the level of the biomarker or biomarkers in a second biological sample from the subject;
wherein the first biological sample is obtained from the subject before the subject is administered a treatment to improve compromised hepatic enzyme activity associated with the organic acidemia, and the second biological is obtained from the subject after the subject is administered the treatment;
wherein a decrease in the level of biomarker or biomarkers from the second biological sample compared to the level of the biomarker or biomarkers from the first biological sample indicates efficacy of the treatment.

23. A method for diagnosing hepatic mitochondrial dysfunction in a subject suffered from an organic acidemia, the method comprising:
detecting the level of a biomarker or biomarkers in a biological sample from the subject, wherein the biomarker is a fibroblast growth factor 21 (FGF21) gene expression product or a growth differentiation factor 15 (GDF15) gene expression product, or both;
wherein an increase in the level of the biomarker or biomarkers compared to a predetermined standard level indicates that the subject is suffering from hepatic mitochondrial dysfunction.

24. A kit comprising:
an antibody that specifically recognizes a protein selected from the group consisting of FGF21 GDF15, Gadd45b, Gstm3, Pdk4, Rragd, Slc7A11, Asns, Abcc4, Fasn, and Hsd3b2;
guidance for testing before, during, and/or after treatment; and
guidance for interpreting the test results.

25. A kit comprising:
DNA that recognizes mRNA that expresses a protein selected from the group consisting of FGF21, GDF15, Gadd45b, Gstm3, Pdk4, Rragd, Slc7A11, Asns, Abcc4, Fasn, and Hsd3b2;
guidance for testing before, during, and/or after treatment; and
guidance for interpreting the test results.

26. A method for determining the efficacy of a treatment for an organic acidemia in a subject, the method comprising:
detecting the level of a biomarker or biomarkers in a biological sample from the subject prior to the treatment, wherein the biomarker or biomarkers is selected from the group consisting of Gadd45b, Gstm3, Pdk4, Rragd, Slc7A11, Asns, Abcc4, Fasn, and Hsd3b2 gene expression product; and
detecting the level of the biomarker or biomarkers in a biological sample from the subject after the treatment;
wherein a decrease in the level of the biomarker or biomarkers after the treatment compared to the level of the biomarker or biomarkers prior to the treatment indicates efficacy of the treatment.

27. A method for monitoring the severity of an organic acidemia in a subject, the method comprising:

detecting the level of fibroblast growth factor 21 (FGF21) in a biological sample from the subject prior to a treatment and detecting the level of FGF21 in a biological sample from the subject after the treatment;
wherein a decrease in the level of FGF21 after the treatment compared to the level of FGF21 prior to the treatment indicates reduced severity of the organic acidemia

BRIEF DESCRIPTION OF THE DRAWINGS

(FIG. 1A) Overview of the strategy used to generate Mut$^{-/-}$; Tg$^{INS-MCK-Mut}$ mice (FIG. 1B) survival compared to Mut$^{-/-}$ mice (FIG. 1C) weight gain on varied diets (FIG. 1D) the phenotypic appearance of Mut$^{-/-}$; Tg$^{INS-MCK-Mut}$ mice compared to control littermates fed a regular or high-fat diet (FIG. 1E) Mut mRNA expression in the various tissues from Mut$^{-/-}$; Tg$^{INS-MCK-Mut}$ mice (FIG. 1F) Western analysis showing over-expression confined to the skeletal muscle (FIG. 1G) plasma methylmalonic acid in the Mut$^{-/-}$; Tg$^{INS-MCK-Mut}$ mice and the effect of diet (FIG. 1H) 1-C-13 propionate oxidation in the Mut$^{-/-}$; Tg$^{INS-MCK-Mut}$ mice.

FIG. 2 shows hepatic ultrastructural changes in Mut$^{-/-}$; Tg$^{INS-MCK-Mut}$ mice (a,b) compared to a Mut$^{+/-}$; Tg$^{INS-MCK-Mut}$ control (c).

FIGS. 3A-B shows diminished hepatic electron transport chain immunoreactive enzyme (FIG. 3A) and activity (FIG. 3B) in Mut$^{-/-}$; Tg$^{INS-MCK-Mut}$ mice compared to a Mut$^{+/-}$; Tg$^{INS-MCK-Mut}$ control.

DETAILED DESCRIPTION OF CERTAIN EMBODIMENTS

Figure 1A:
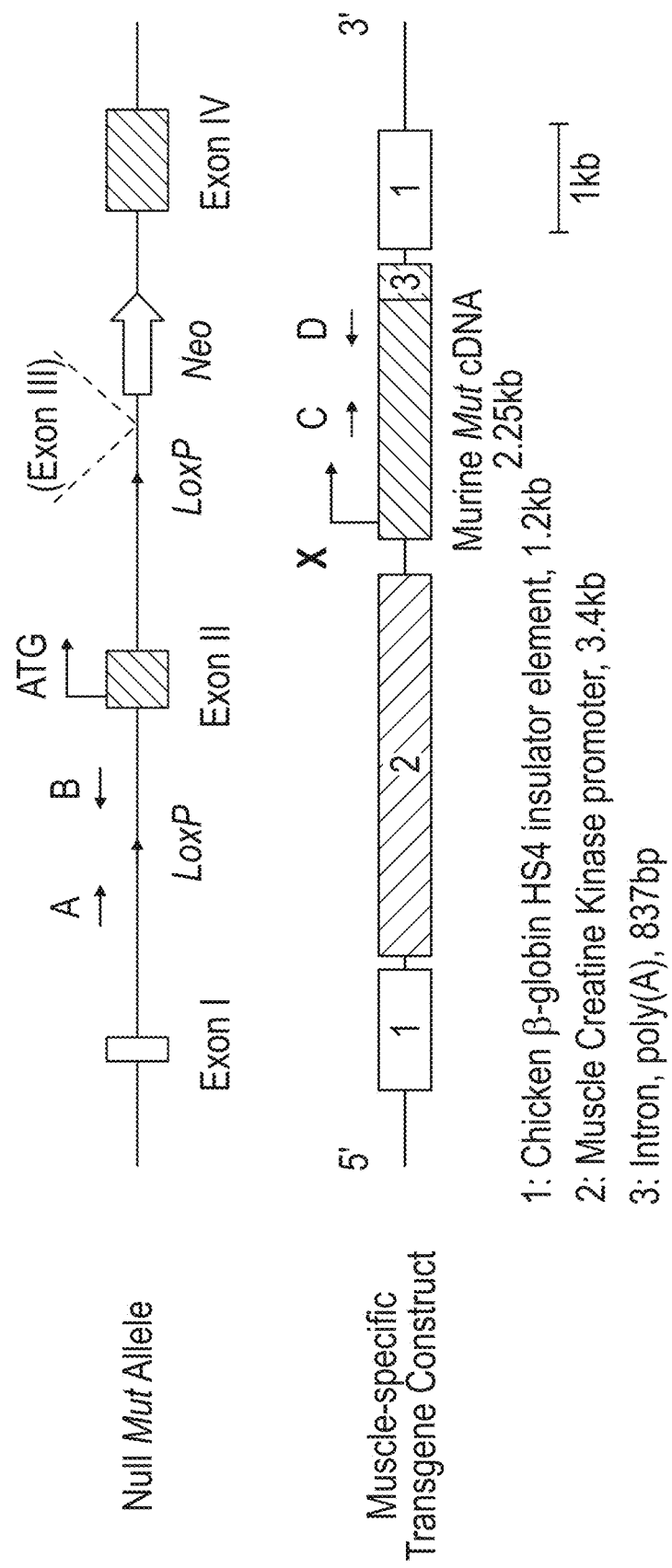
FIGS. 1A-H.

Reference will now be made in detail to representative embodiments of the invention. While the invention will be described in conjunction with the enumerated embodiments, it will be understood that the invention is not intended to be limited to those embodiments. On the contrary, the invention is intended to cover all alternatives, modifications, and equivalents that may be included within the scope of the present invention as defined by the claims.

One skilled in the art will recognize many methods and materials similar or equivalent to those described herein, which could be used in and are within the scope of the practice of the present invention. The present invention is in no way limited to the methods and materials described.

Definitions

Unless defined otherwise, technical and scientific terms used herein have the same meaning as commonly understood by one of ordinary skill in the art to which this invention belongs. Any methods, devices, and materials similar or equivalent to those described herein can be used in the practice or testing of the invention.

As used in this application, including the appended claims, the singular forms "a," "an," and "the" include plural references, unless the content clearly dictates otherwise, and are used interchangeably with "at least one" and "one or more."

As used herein, the term "about" represents an insignificant modification or variation of the numerical value such that the basic function of the item to which the numerical value relates is unchanged.

As used herein, the terms "comprises," "comprising," "includes," "including," "contains," "containing," and any variations thereof, are intended to cover a non-exclusive inclusion, such that a process, method, product-by-process, or composition of matter that comprises, includes, or contains an element or list of elements does not include only those elements but may include other elements not expressly listed or inherent to such process, method, product-by-process, or composition of matter.

The term "subject" or "patient", as used herein, refers to a domesticated animal, a farm animal, a primate, a mammal, for example, a human.

As used herein, "determining", "determination", "detecting", or the like are used interchangeably herein and refer to the detecting or quantitation (measurement) of a molecule using any suitable method, including immunohistochemistry, fluorescence, chemiluminescence, radioactive labeling, surface plasmon resonance, surface acoustic waves, mass spectrometry, infrared spectroscopy, Raman spectroscopy, atomic force microscopy, scanning tunneling microscopy, electrochemical detection methods, nuclear magnetic resonance, quantum dots, and the like. "Detecting" and its variations refer to the identification or observation of the presence of a molecule in a biological sample, and/or to the measurement of the molecule's value.

As used herein, the terms "treat," "treating", and "treatment" mean to alleviate symptoms, eliminate the causation of symptoms either on a temporary or permanent basis, or to prevent or slow the appearance of symptoms of the named disorder or condition. Treatment is, in certain embodiments, directed at a subject or patient suffering from an organic acidemia, and may reduce the severity of the organic acidemia, or retard or slow the progression of the organic acidemia. Standard treatments include, but are not limited to, a limited protein/high carbohydrate diet, intravenous fluids, amino acid substitution, vitamin supplementation, carnitine, induced anabolism, and tube-feeding. Exemplary treatments include more aggressive treatments like liver transplant, combined liver and kidney transplant, and emerging therapies involving gene, mRNA, cell, small molecule, microbiome, or any other processes that could improve MUT or PCC activity or propionate oxidation or associated mitochondrial dysfunction. In one embodiment, the treatment is liver-directed treatment.

As used herein, the term "organic acidemia" refers to a group of inheritable metabolic disorders which disrupt normal amino acid metabolism, particularly branched-chain amino acids, causing a buildup of acids which are usually not present. Exemplary organic acidemias include, but not limited to, methylmalonic acidemia (MMA), propionic acidemia (PA), isovaleric acidemia (IVA), glutaric aciduria type 1 (GA1), beta-ketothiolase deficiency (BKT), 3-methylcrotonyl-CoA carboxylase deficiency (3-MCC), 3-hydroxy-3-methylglutaryl-CoA lyase deficiency (HMG), 3-Methylglutaconic acidemia or 3-Methylglutaconyl-CoA Hydratase Deficiency (MGA), D-2 Hydroxyglutaric Aciduria (D2-HGA), Isobutyryl-CoA Dehydrogenase Deficiency 3-Hydroxyisobutyric aciduria (ICBD), L-2-Hydroxy-glutaricaciduria (L2HGA), Malonyl-CoA Decarboxylase Deficiency aka Malonic Acidemia (MA), Multiple carboxylase deficiency (MCD, holocarboxylase synthetase), and 3-Hydroxyisobutyryl-CoA Hydrolase Deficiency (HIBCH). MMA is an autosomal recessive disorder caused by defects in the mitochondrial localized enzyme methylmalonyl-CoA mutase (MUT) resulting in the accumulation of methylmalonic acid. Defects in the transport and metabolism of the cofactor for MUT, 5'deoxyadenosylcobalamin, also can cause MUT deficiency. These disorders include cblA, cblB and cblD class of MMA, and the corresponding genes, MMAA (cblA), MMAB (cblB), and MMADHC (cblD). In addition, MMACHC (cblC), LMBRD1 (cblF), ABCD4 (cblJ), TC2 (transcobalamin 2), CD320, AMN (encoding amnionless), cblC, cblF, cblJ, TC2, TCBLR (transcobalamin receptor) or Imerslund-Graesbeck forms of combined MMAemia-hyperhomocysteinemia may also cause MUT deficiency. PA is an autosomal recessive disorder caused by defects in propionyl-CoA carboxylase (PCC) of either the propionyl CoA carboxylase alpha (PCCA) or beta subunits (PCCB) and resulting in the accumulation of propionic acid and related metabolites. IVA is an autosomal recessive inborn error of leucine metabolism caused by a deficiency of the mitochondrial enzyme isovaleryl-CoA dehydrogenase (IVD) resulting in the accumulation of derivatives of isovaleryl-CoA.

As used herein, the term "cobalamin metabolic and transport disorder" refers to disorders associated with cobalamin deficiency. Exemplary cobalamin metabolism disorders include, but are not limited to, MMACHC (cblC), MMADHC (cblD), LMBRD1(cblF), ABCD4(cblJ), TC2, CD320, AMN, cblC, cblD, cblF, cblJ, TC2, TCBLR (transcobalamin receptor) or Imerslund-Gräesbeck forms of combined MMAemia-hyperhomocysteinemia. Diagnosis of disorders of intracellular cobalamin metabolism is confirmed by identification of biallelic pathogenic variants in one of the following genes (associated complementation groups indicated in parentheses): MMACHC (cblC), MMADHC (cblD and cblD variant 1), MTRR (cblE), LMBRD1 (cblF), MTR (cblG), and ABCD4 (cblJ). cblC is the most common cobalamin metabolic disorder.

As used herein, the term "disorder of propionate metabolism" refers to disorders associated with the chemical reactions and pathways involving propionate. Exemplary disorders of propionate metabolism include, but are not limited to, MMA and PA.

As used herein, the term "gene expression product" encompasses both nucleic acid (e.g., mRNA or cDNA derived from it) and protein products of expression of a gene. Nucleic acid expression products may or may not include subsequences that do not encode and/or get translated into protein. Gene expression product encompass both full-length, naturally occurring molecules, as well as fragments thereof, provided the fragments permit identification of the gene expression product, relative to other molecules expected to be present in the sample being analyzed.

As used herein, the term "efficacy" refers to any increase in the therapeutic benefit to the subject.

As used herein, the term "biological sample" refers to a sample obtained from a biological subject. Exemplary biological samples include, but not limited to, cell lysate, a cell culture, a cell line, a tissue, oral tissue, gastrointestinal tissue, an organ, an organelle, a biological fluid, a blood sample, a plasma sample, a serum sample, a urine sample, a skin sample, and the like.

As used herein, the term "biomarker" refers to a measurable parameter, or combination of parameters, that can be used as an indicator of a biological state and includes, but not limited to, proteins and nucleic acids. In one embodiment, the biomarker is a cytokine. Exemplary biomarkers include, but are not limited to, FGF21, GDF15, Gadd45b, Gstm3, Pdk4, Rragd, Slc7A11, Asns, Abcc4, Fasn, and Hsd3b2 gene expression product, and any combination thereof.

As used herein, the term "predetermined standard level" refers to an accepted level of the biomarker used to compare the biomarker level derived from a sample of a subject. In one embodiment, the predetermined standard level of the biomarker indicates an unaffected, i.e., non-disease, state of a subject who does not have an organic acidemia.

As used herein, the term "decrease" refers to a level of the biomarker smaller in value. As used herein, the term "increase" refers to a level of the biomarker larger in value.

"Level of a biomarker" refers to the amount of gene expression product (e.g., mRNA or protein) and may be normalized or standardized by any suitable means.

"Determining a level of a biomarker" is a dynamic (i.e., before, during, or following treatment) measurement of the amount of a gene expression product and encompasses both measurement at a single timepoint, as well as multiple measurements—such as a time series of at least 2, 3, 4, 5, or more measurements. A "time series" is a group of 2 or more determined levels of gene expression product relative to a treatment—e.g. a series of pre-treatment and/or post-treatment measurements. Measurement(s) may be analyzed as absolute measurements of concentration or may be transformed, e.g., log normalized; normalized as a difference or fold change, e.g. between baseline and peak (relative maximum) in the same series of measurement or relative to another time (e.g. a pre-treatment baseline measurement from another time series for the subject, or a reference standard, e.g., either pre- or post-treatment reference standards); total or incremental area under the curve (AUC); total or incremental AUC after peak levels; or time (or rate) to increase (or decrease) to (from) a peak level, or some fraction thereof, e.g. 95, 90, 80, 70, 60, 50, 40, 30, 20, 10, or 5%, and in particular embodiments about 50% of peak level. The determined level(s) or transformed level(s) of a gene expression product is the subjects' "treatment response".

Methods

In one embodiment, the methods provided by the invention entail determining the level of a biomarker in a biological sample from the subject. The biomarker or biomarkers is selected from the group consisting of FGF21, GDF15, Gadd45b, Gstm3, Pdk4, Rragd, Slc7A11, Asns, Abcc4, Fasn, and Hsd3b2 gene expression product, and combination thereof. Any portion of a gene expression product may be suitable for detection, provided it sufficiently identifies the gene expression product relative to other materials expected to be present in the biological sample.

The biomarker levels can be determined at either the protein or nucleic acid level by any suitable means known in the art. For example, for measuring FGF21/GDF15 levels at the protein level, the level of FGF21/GDF15 protein gene expression product may be determined by ELISA, Western Blotting, RIA (radioimmunoassay), nucleic acid-based or protein-based aptamer techniques, HPLC (high performance liquid chromatography), SPR (surface plasmon resonance), SAT (suspension array technology-including both immune-based, aptamer-based, or combination methods), direct peptide sequencing (such as Edman degradation sequencing), or mass spectrometry (such as MS/MS, optionally coupled to HPLC). In particular embodiments, the level of an FGF21/GDF15 protein gene expression product is determined by ELISA.

Many of the modalities for determining the level of a protein gene expression product employ antibodies. The gene is FGF21, GDF15, Gadd45b, Gstm3, Pdk4, Rragd, Slc7A11, Asns, Abcc4, Fasn, or Hsd3b2. "Antibody," "antibodies," and the like, as used herein, refers to an immunoglobulin or a part thereof, and encompasses any polypeptide comprising an antigen binding site regardless of the source, species of origin, method of production, and characteristics. As a non-limiting example, the term "antibody" includes human, orangutan, mouse, rat, goat, rabbit, sheep, and chicken antibodies. The term includes but is not limited to polyclonal, monoclonal, monospecific, polyspecific, non-specific, humanized, camelized, singlechain, chimeric, synthetic, recombinant, hybrid, mutated, and CDR-grafted antibodies. For the purposes of the present invention, it also includes, unless otherwise stated, antibody fragments such as Fab, F(ab')2, Fv, scFv, Fd, dAb, VHH (also referred to as nanobodies), and other antibody fragments that retain the antigen-binding function. In some embodiments, the term "antibody" includes an antigen-binding molecule based on a scaffold other than an immunoglobulin.

Antibodies can be raised against any of the suitable analytes for protein gene expression products, described above. Numerous antibodies are available commercially from a variety of vendors. All of these antibodies can be adapted for use in the methods provided by the invention. Antibodies for use in the methods provided by the invention can be detectably labeled (e.g., biotinylation, fluorescent, radio labeled, etcetera) by any suitable means or may be detected indirectly, e.g., using a detectably labeled secondary antibody. In particular embodiments, the antibody is part of a kit, such as an ELISA kit.

Likewise, for measuring levels of a nucleic acid gene expression product (e.g. in a liver biopsy or subcutaneous adipose biopsy), the level of nucleic acid gene expression can be determined by microarray, quantitative polymerase chain reaction (qPCR), quantitative real-time polymerase chain reaction (qRTPCR), sequencing, northern blotting, digital drop PCR (ddPCR), or Southern blotting.

FGF21, a potent activator of glucose uptake, has been proposed to be related to insulin resistance, metabolic syndrome (MetS), nonalcoholic fatty liver disease (NAFLD), and weight status. FGF21 stimulates glucose uptake in adipocytes via the induction of glucose transporter-1. This action is additive and independent of insulin. FGF21 is a hormone with antihyperglycemic, antihyperlipidemic, and thermogenic properties. FGF21 activity depends on its binding to FGFRs and a cofactor called β-Klotho, a single-pass transmembrane protein whose expression is induced during differentiation from preadipocytes to adipocytes. The cofactor β-Klotho is predominantly expressed in metabolic organs including liver, white adipose tissue, and pancreas.

FGF21 expression is controlled by different transcriptional factors such as peroxisome proliferator-activated receptor α (PPAR α (PPARA)) in the liver and PPARγ (PPARG) in adipocytes. FGF21 reduces physical activity and promotes torpor in mice, a short-term hibernation state with the aim of saving energy by reducing physical activity and body temperature energy. FGF21 increases in healthy subjects only after a 7-day fast, supporting the hypothesis that FGF21 is induced by prolonged fasting in humans as also occurs in mice.

GDF15 belongs to the TGF-β superfamily, which has a function of regulating inflammation and apoptosis during progress of damaged tissue or disease. GDF15 is also known as TGF-PL, MIC-1, PDF, PLAB, and PTGFB.

The invention advantageously provides a non-invasive blood-based biomarker for monitoring, for example, mitochondrial dysfunction in MMA and PA. In one embodiment, the invention replaces known invasive monitoring procedures, such as muscle, liver, or renal biopsies. In another embodiment, the invention provides a more sensitive biomarker for clinical treatment responses, i.e., can monitor mitochondrial dysfunction responses to therapeutics before showing clinical symptoms, for example, of hepatic mitochondrial function.

In certain embodiments, the invention provides biomarkers FGF21 and GDF15 to measure the effects of any intervention on hepatic MUT or PCC activity and the effects of hepatic MUT or PCC deficiency, and the secondary mitochondropathy associated with MUT and PCC deficiency. In some embodiments, the invention provides new biomarkers that could be used to monitor the effects of gene, mRNA, cell, small molecule, microbiome, or any other process that could improve MUT or PCC activity or propionate oxidation or associated mitochondrial dysfunction. Such monitoring would be helpful for vitamin B12 deficiency and any enzymes that depend on vitamin B12 and possibly biotin. The new biomarkers can be similarly used to follow treatment(s) for propionic acidemia, or other organic acidemias. In one aspect, the new biomarker is FGF21, GDF15, Gadd45b, Gstm3, Pdk4, Rragd, Slc7A11, Asns, Abcc4, Fasn, or Hsd3b2.

In certain embodiments, the invention could be applied to propionate oxidation disorders, including all forms of propionic acidemia, methylmalonic acidemia, cobalamin defects (cblA, B, C, D, F, J; TC2, TCBLR, AMN), vitamin B12 and biotin deficiency; disorders that affect hepatic mitochondrial metabolism; to test for effects of drugs that affect hepatic metabolism such as HIV medicines, and any therapies directed toward these disorders, including but not limited to, hepatic gene therapy with any vector (AAV, adenovirus, lentivirus), cell therapy, small molecules, enzyme specific chaperonins, engineered microbes/microbiome, mRNA therapy, enzyme replacement therapy, and genome editing therapies. In one embodiment, the method is applied for any form of MMA or PA.

In some embodiments, the invention provides a method for determining the efficacy of a treatment for an organic acidemia in a subject. The method comprises the step of detecting the level of a biomarker or biomarkers in a biological sample from the subject prior to the treatment, wherein the biomarker or biomarkers is an FGF21 gene expression product or a GDF15 gene expression product, or both. The method further comprises the step of detecting the level of the biomarker in a biological sample from the subject after the treatment, wherein a decrease in the level of the biomarker or biomarkers after the treatment compared to the level of the biomarker prior to the treatment indicates efficacy of the treatment.

In another embodiment, the biomarker is an FGF21 gene expression product. In another embodiment, the biomarker is a GDF15 gene expression product. In another embodiment, the biomarker comprises both an FGF21 gene expression product and a GDF15 gene expression product. In another embodiment, the biomarker is a protein. In another embodiment, the biomarker is detected at the nucleic acid level. In another embodiment, the biological sample is a serum sample. In another embodiment, the biological sample is a plasma sample.

In another embodiment, the treatment is a liver-directed treatment. In another embodiment, the treatment comprises administering to the subject a liver-directed gene transfer vector. In another embodiment, the treatment is selected from the group consisting of gene therapy, mRNA therapy, cell therapy, small molecule therapy, and microbiome therapy. In another embodiment, the gene therapy reagents comprise adeno-associated viral (AAV) vectors. In another embodiment, the treatment comprises mRNA therapy, integrating AAV vectors to accomplish MUT genome editing into the albumin locus, and microbiome engineering to clear toxic metabolites from the gut.

In another embodiment, the organic acidemia is selected from the group consisting of methylmalonic academia, propionic academia, isovaleric academia, glutaric aciduria type 1 (GA1), beta-ketothiolase deficiency (BKT), 3-methylcrotonyl-CoA carboxylase deficiency (3-MCC), 3-hydroxy-3-methylglutaryl-CoA lyase deficiency (HMG), 3-Methylglutaconic acidemia or 3-Methylglutaconyl-CoA Hydratase Deficiency (MGA), D-2 Hydroxyglutaric Aciduria (D2-HGA), Isobutyryl-CoA Dehydrogenase Deficiency 3-Hydroxyisobutyric aciduria (ICBD), L-2-Hydroxyglutaricaciduria (L2HGA), Malonyl-CoA Decarboxylase Deficiency aka Malonic Acidemia (MA), Multiple carboxylase deficiency (MCD, holocarboxylase synthetase), and 3-Hydroxyisobutyryl-CoA Hydrolase Deficiency (HIBCH). In another embodiment, the organic acidemia is methylmalonic academia or propionic academia. In another embodiment, the organic acidemia is a disorder of propionate metabolism or a cobalamin metabolic and transport disorder causing MUT deficiency. In another embodiment, the disorders of propionate metabolism is caused by isolated MUT (mut) deficiency, or MMAA (cblA), MMAB (cblB), MMADHC (cblD) or cblA, cblB, cblD variant 2 classes of MMA. In another embodiment, the cobalamin metabolic and transport disorder is MMACHC (cblC), MMADHC (cblD), LMBDR1 (cblF), ABCD4 (cblJ), TC2 (transcobalamin 2), CD320, AMN (encoding amnionless), cblC, cblD, cblF, cblJ, TC2, TCBLR (transcobalamin receptor) or Imerslund-Gräesbeck forms of combined MMAemia-hyperhomocysteinemia.

In another embodiment, the treatment is liver transplantation or combined liver and kidney transplantation.

In some embodiments, the method comprises the step of detecting the level of a biomarker or biomarkers in a biological sample from the subject after the treatment, wherein a decrease in the level of the biomarker compared to a predetermined standard level indicates efficacy of the treatment, wherein the biomarker is an FGF21 gene expression product, a GDF15 gene expression product, or both.

In some embodiments, the invention provides a method for determining the efficacy of a liver-directed treatment for an organic acidemia in a subject.

In some embodiments, the invention provides a method of treating a subject for an organic acidemia. The method comprises the step of detecting the level of a biomarker or biomarkers in a biological sample from the subject prior to the treatment, wherein the biomarker is an FGF21 gene expression product or a GDF15 gene expression product, or both. The method further comprises the step of administering a treatment to the subject to improve compromised hepatic enzyme activity associated with the organic acidemia associated with the organic acidemia. The method further comprises the step of detecting the level of the biomarker in a biological sample from the subject after the treatment, wherein a decrease in the level of biomarker after the treatment compared to the level of the biomarker prior to the treatment indicates efficacy of the treatment. In another embodiment, the subsequent treatment course can be altered or continued based on the degree of treatment efficacy.

In some embodiments, the invention provides a method for improving hepatic enzyme activity in a subject having an organic acidemia. The method comprises the step of detecting the level of a biomarker or biomarkers in a biological sample from the subject prior to the treatment, wherein the biomarker is an FGF21 gene expression product or a GDF15 gene expression product, or both. The method further comprises a step of administering a treatment to the subject to improve compromised hepatic enzyme activity associated with the organic acidemia. The method further comprises a step of detecting the level of the biomarker in a biological sample from the subject after the treatment. The method further comprises the step of discontinuing, altering, or continuing the treatment based on the level after treatment compared to the level before treatment. In another embodiment, the method further comprises the step of subsequently continuing the course of treatment on the subject upon determining a decrease in the level of the biomarker after the treatment compared to the level of the biomarker prior to the treatment. In another embodiment, the treatment is a liver-directed treatment. In some embodiments, the enzyme is selected from the group consisting of methylmalonyl-CoA mutase, propionyl CoA carboxylase, isovaleryl-CoA dehydrogenase, Glutaryl CoA Dehydrogenase, beta-ketothiolase, 3-methylcrotonyl-CoA carboxylase, 3-hydroxy-3-methyl-glutaryl-CoA lyase, 3-Methylglutaconyl-CoA Hydratase, Isobutyryl-CoA Dehydrogenase, Malonyl-CoA Decarboxylase, Multiple carboxylase, and 3-Hydroxyisobutyryl-CoA Hydrolase.

In some embodiments, the invention provides a method of treating a subject with an organic acidemia. The method comprises a step of detecting the level of a biomarker or biomarkers in a first biological sample from the subject, wherein the biomarker is an FGF21 gene expression product or a GDF15 gene expression product, or both. The method further comprises a step of detecting the level of the biomarker in a second biological sample from the subject. The first biological sample is obtained from the subject before the subject is administered a treatment to improve compromised hepatic enzyme activity associated with the organic acidemia associated with the organic acidemia, and the second biological is obtained from the subject after the subject is administered the treatment. A decrease in the level of biomarker from the second biological sample compared to the level of the biomarker from the first biological sample indicates efficacy of the treatment.

In some embodiments, the invention provides a method for diagnosing hepatic mitochondrial dysfunction in a subject suffered from an organic acidemia. The method comprises detecting the level of a biomarker or biomarkers in a biological sample from the subject, wherein the biomarker is an FGF21 gene expression product, a GDF15 gene expression product, or both, wherein an increase in the level of the biomarker compared to a predetermined standard level indicates the subject is suffered from hepatic mitochondrial dysfunction.

In some embodiments, the invention provides a method for determining the efficacy of a treatment for an organic acidemia in a subject. The method comprises the step of detecting the level of a biomarker or biomarkers in a biological sample obtained from the subject prior to the treatment, wherein the biomarker or biomarkers is selected from the group consisting of Gadd45b, Gstm3, Pdk4, Rragd, Slc7A11, Asns, Abcc4, Fasn, and Hsd3b2 gene expression product. The method further comprises the step of detecting the level of the biomarker or biomarkers in a biological sample from the subject after the treatment. In the embodiments, a decrease in the level of the biomarker or biomarkers after the treatment compared to the level of the biomarker or biomarkers prior to the treatment indicates efficacy of the treatment.

In one embodiment, the method could be applied to propionate oxidation disorders, including all forms of propionic acidemia, methylmalonic acidemia, cobalamin defects (cblA-J), vitamin B12 and biotin deficiency; disorders that affect hepatic mitochondrial metabolism; to test for effects of drugs that affect hepatic metabolism such as HIV medicines, and any therapies directed toward these disorders, including but not limited to, hepatic gene therapy with any vector (AAV, adenovirus, lentivirus), cell therapy, small molecules, enzyme specific chaperonins, engineered microbes/microbiome, mRNA therapy, enzyme replacement therapy, and genome editing therapies.

Kits

In one embodiment, a kit for detecting the mRNA level of FGF21, GDF15, or both is provided. In one embodiment, the kit comprises one or more probes that bind specifically to the mRNAs of FGF21 or GDF15. In one embodiment, the kit further comprises a washing solution. In certain embodiments, the kit further comprises reagents for performing a hybridization assay, mRNA isolation or purification means, detection means, as well as positive and negative controls. In certain embodiments, the kit further comprises instructions for using the kit. The instructions can be in the form of printed material or in the form of an electronic support capable of storing instructions such that they can be read by a subject, such as electronic storage media (magnetic disks, tapes and the like), optical media (CD-ROM, DVD) and the like. Alternatively or in addition, the media can contain Internet addresses that provide the instructions. The kit can be tailored for in-home use, clinical use, or research use.

In one embodiment, a kit for detecting the protein level of FGF21, GDF15, or both is provided. In one embodiment, the kit comprises a dipstick coated with an antibody that recognizes the protein biomarker, washing solutions, reagents for performing the assay, protein isolation or purification means, detection means, as well as positive and negative controls. In certain embodiments, the kit further comprises an instruction for using the kit. The kit can be tailored for in-home use, clinical use, or research use.

In one embodiment, the invention provides a kit useful for determining the efficacy of a treatment for an organic acidemia. In one embodiment, the invention provides a kit useful for determining the efficacy of a liver-directed treatment for an organic acidemia.

In some embodiments, the invention provides a kit for diagnosing a subject for an organic acidemia. The kit comprises an antibody that specifically recognizes a protein selected from the group consisting of FGF21 and GDF15. The kit may further comprise guidance for testing before, during, and/or after treatment and guidance for interpreting the results. In one aspect, the kit further comprises a therapeutic agent for the organic acidemia. Additionally, the kits of the invention can contain instructions for the simultaneous, sequential or separate use of the different components contained in the kit.

In some embodiments, the kit includes DNA that recognizes mRNA that expresses a protein selected from the group consisting of FGF21 and GDF15. The kit may further comprise guidance for testing before, during, and/or after treatment and guidance for interpreting the results. In one aspect, the kit further comprises a therapeutic agent for the organic acidemia. Additionally, the kits of the invention can contain instructions for the simultaneous, sequential or separate use of the different components contained in the kit.

In some embodiments, the kit comprises an antibody that specifically recognizes a protein selected from the group consisting of Gadd45b, Gstm3, Pdk4, Rragd, Slc7A11, Asns, Abcc4, Fasn, and Hsd3b2, guidance for testing before, during, and/or after treatment, and guidance for interpreting the test result. In another embodiment, the kit comprises DNA that recognizes mRNA that expresses a protein selected from the group consisting of Gadd45b, Gstm3, Pdk4, Rragd, Slc7A11, Asns, Abcc4, Fasn, and Hsd3b2, guidance for testing before, during, and/or after treatment, and guidance for interpreting the test results.

EXAMPLES

Example 1: Methods and Materials

Example 1.1 Generation of Mut$^{-/-}$; Tg$^{INS-MCK-Mut}$ Mice

Mut$^{-/-}$; Tg$^{INS-MCK-Mut}$ Mice used in the studies described herein. Methylmalonyl-CoA mutase (Mut) knockout mice harboring a deletion of exon three have been described, with confirmation of disrupted enzymatic function of methylmalonyl-CoA mutase and lack mRNA and protein production (Chandler et al. BMC Med Genet. 2007; 8:64, Metabolic phenotype of methylmalonic acidemia in mice and humans: the role of skeletal muscle.). Mice homozygous for this mutation display neonatal lethality.

A skeletal-muscle specific transgene, Tg$^{INS-MCK-Mut}$ was engineered to express the murine Mut gene under the control of the muscle creatine kinase (MCK) promoter. The construct was flanked by chicken β-globin 5' HS4 insulator elements to suppress position effect variegation. Founder C57BL/6 animals were screened for the presence of the INS-MCK-Mut transgene and bred to C57BL/6 mice to test transmission. Transgenic carrier mice were then bred with Mut$^{+/-}$ heterozygous mice of the Mut knock-out line to generate Mut$^{-/-}$; Tg$^{INS-MCK-Mut}$ mice. All animal experiments were approved by the Institutional Animal Care and Use Committee of the National Human Genome Research Institute (NHGRI), National Institutes of Health (NIH).

Example 1.2: Mouse Genotyping

Genotyping carried out in the studies described herein. Mouse genotyping was performed on tail genomic DNA extracted using standard protocols. PCR amplifications were performed across the loxP site of the targeting construct, as well as across the Mut cDNA to detect the INS-MCK-Mut transgene. Primers used were: forward 5'-loxP site: 5'-CCATTCTGGGAAGGCTTCTA-3' and reverse 3'-loxP site 5'-TGCACAGAGTGCTAGTTTCCA-3'. Detection of the INS-MCK-Mut transgene was completed by amplification across the Mut cDNA with primers:

```
Forward: 5'-CATGTTGAGAGCTAAGAATC-3'
and
Reverse: 5'-TAGAAGTTCATTCCAATCCC-3'.
```

Example 1.3: Diet and Housing

Diet and Housing carried out in the studies described herein. Mice were housed in a controlled, pathogen-free environment with a 12 hour light/dark cycle and fed ad libitum with standard chow (PicoLab Mouse Diet 20, LabDiet, St. Louis, Mo.) or a high fat and sugar diet consisting of Diet Induced Obesity Diet (OpenSource Diets™), fruit, and Nutrical® (Tomlyn, Fort Worth, Tex.). A soft version of the regular chow (Nutra-gel diet, Bio-Serv, Flemington, N.J.) was provided for the studies involving AAV administration. For studies involving high protein diet a 70% (wt/wt) casein, or 61% protein chow, (TD.06723, Harlan Laboratories, Madison, Wis.) was provided ad libitum.

Example 4: Fasting Study

Ten male (four Mut$^{-/-}$; Tg$^{INS-MCK-Mut}$ mice and 6 Mut$^{+/-}$; Tg$^{INS-MCK-Mut}$ mice) and nine female (three Mut$^{-/-}$; Tg$^{INS-MCK-Mut}$ mice and six Mut$^{+/-}$; Tg$^{INS-MCK-Mut}$ littermates) underwent a fasting challenge. Mice were deprived of food but had free access to water throughout the fasting study. Food was removed at 12:00 pm, and blood glucose, body temperature, and weight were monitored every 3 hours for 9 hrs, followed by every 2 hours, unless a drop in blood glucose or change in temperature or overall activity levels and behavior of the animal was observed, at which point more frequent monitoring was initiated. The experiment was terminated, and mice were euthanized, once glucose levels dropped to ≤45 mg/dl. This occurred after 16 hrs in 3 female mice that had lower body weights at baseline, (14.6±6.6 gr, mean±SD). The average body weight for the male mice was 19.57±2.3 gr, and they all tolerated the fasting well. Males were sacrificed at the same time with the females for blood and tissue collection for gene expression studies. Tissues were snap-frozen in liquid nitrogen for RNA extraction, and terminal blood sampling was obtained for metabolomic and targeted biochemical studies.

Example 1.5: FITC-Inulin Clearance Studies

FITC-Inulin Clearance carried out in the studies described herein. Glomerular filtration rate (GFR) was assessed by the single-injection FITC-inulin clearance method. Briefly, serial plasma collections were taken from tail cuts following injection of FITC-inulin and fluorescence measurements of resultant samples were used to determine the rate of decay in comparison to standard curve. Under 1-3% isoflurane anesthesia, mice were given a single bolus retro-orbital injection of 2.5% FITC-inulin (3.74 µl/g body weight). Heparinized blood collections (5 µl volume) from tail cuts were performed at 3, 7, 10, 15, 35, 55, and 75 minutes. Plasma was separated under centrifugation (3 min, 10,000 rpm). Since pH affects FITC fluorescence values, each plasma sample was buffered by mixing 10 plasma with 9 µl 500 mM HEPES solution (pH 7.4). The amount of FITC label present in the samples was then measured using a fluorospectrometer at 538-nm emission (Thermo Scientific, NanoDrop 3300). A two-compartment clearance model was used to calculate GFR. Plasma fluorescence data were fit to a two-phase exponential decay curve using nonlinear regression (GraphPad Prism, GraphPad Software, San Diego, Calif.). GFR (µl/min) was calculated using the equation: GFR=I/(A/α+B/β), where I is the amount of FITC-inulin delivered by injection, A and B are the y-intercept values of the two decay rates, and α and β are the decay constants for the distribution and elimination phases, respectively.

Example 1.6: Clinical Chemistry Screen

Clinical chemistry screen carried out in the studies described herein. Murine plasma was obtained terminally by retro-orbital blood collection using heparinized glass capillary tubes (Drummond Scientific, Broomall, Pa.) following intraperitoneal injection of pentobarbital (5 mg/ml, dose of 0.2-0.3 ml/10 g body weight). The samples were centrifuged (4° C., 10 min, 10,000 rpm), the plasma removed, and stored at −80° C. in a screw-top tube for later analysis. Methylmalonic acid was analyzed in plasma and urine samples by gas chromatography-mass spectrometry with stable isotopic calibration.

Methylmalonic acid values were measured in patient plasma samples using liquid chromatography-tandem mass spectrometry stable isotope dilution analysis (Mayo Medical Laboratories). Estimated GFR was calculated using serum creatinine, BUN and cystatin-C, using the updated CKID equation. 24-hr urine collections were performed in a subset of patients for calculating creatinine clearance (displayed as milliliters per minute per 1.73 m2).

Example 1.7: Western Blot & Enzymatic Activity

Western blot & enzymatic activity essay carried out in the studies described herein. Tissue samples were homogenized by tissue grinder in the presence of T-PER and Halt protease inhibitor mixture (both Pierce Biotechnology). Lysates were centrifuged at 10,000 rpm for 10 min at 4° C., and supernatants were collected. 20-30 µg of clarified protein extract were analyzed by Western blot. Protein bands were quantified using ImageJ software (NIH).

To determine mitochondrial respiratory complex activity 40-70 mg of tissue was homogenized in CPT (0.5 M Tris-HCl, 0.15 M KCl; pH 7.5) and centrifuged at 2,500×g for 20 min at 4° C. Resulting supernatant was used for protein quantification, detection, and enzymatic activity. 10% Extracts of CPT solution were used to measure Complex I activity by oxidation of NADH, and cytochrome c oxidase (COX or complex IV) reduction of cytochrome c at 340 and 550 nm respectively.

Example 1.8: Histology & Immunohistochemistry

Histology & Immunohistochemistry carried out in the studies described herein. To visualize histological features and mitochondrial abnormalities, frozen sections of kidney and liver were cut and stained with COX, SDH, and combined COX-SDH reactions. These sections were examined with an Olympus BX51 microscope with a computer-assisted image analysis system. H&E staining was also performed on paraffin sections of various tissues by Histoserv, Inc, Germantown, Md.

Example 1.9: Electron Microscopy

Electron microscopy carried out in the studies described herein. Transmission electron microscopy (EM) samples were fixed over night, embedded in resin, and cut into ~80 nm sections and placed onto 330-mesh copper grids for staining. Samples were imaged in the JEM-1200EXII electron microscope (JEOL) at 80 kV.

Example 1.10: Patient Studies

The human studies were approved by the NHGRI institutional review board as part of a NIH protocol (ClinicalTrials.gov identifier: NCT00078078) and were performed in compliance with the Helsinki Declaration.

Example 1.11: Microarray

Microarray studies were carried out as described herein. For transcriptome analysis liver tissue RNA expression was studied in livers from the following 4 conditions: heterozygote Mut$^{+/-}$; Tg$^{INS-MCK-Mut}$ mice at baseline and after 12 hrs of fasting, mutant Mut$^{-/-}$; Tg$^{INS-MCK-Mut}$ mice at baseline and after 8-12 hrs of fasting. Four mice in each genotype group and fed or fasting state were sacrificed for liver and RNA extraction. All the mice used in this study were males, at 4 months of age. After organ removal, livers were snap frozen in liquid nitrogen. Total RNA from liver tissue was extracted using the RNA mini kit (74104 Qiagen). cDNA was labeled by the GeneChip Ambion WT expression kit for 1.0 ST chips (4411973; Ambion) and hybridized to Affymetrix GeneChip Mouse Gene 1.0ST Arrays (901168; Affymetrix) according to the manufacturer's instructions. Data were analyzed using Partel Genomics Suite software (Partek) and pathway analysis was conducted using Ingenuity Pathway analysis (Ingenuity Systems).

Principal component analysis was performed generating histograms to assess the biological variability of the microarrays. Using hierarchical cluster analysis, the transcriptomes of the 4 different groups of mice showed satisfactory segregation and differential clustering. Baseline, non-fasting mutant mice showed the lower co-segregation, as expected, given their mixed, non-standardized dietary composition (regular chow, supplemented by fruit/enercal and high fat, for caloric support).

To investigate biological patterns, canonical pathway enrichment analysis was performed using the Ingenuity Pathway Analysis, and a P value for each pathway that was adjusted for multiple testing using the Benjamini-Hochberg method was calculated. A P-value of 0.05 after correcting for multiple comparisons was used to determine statistical significant changes.

Example 1.12: Quantitative Real-Time PCR Analysis

Quantitative real-time PCR analysis carried out in the studies described herein. Total RNA from frozen tissue was extracted using the RNeasy Mini Kit (74104; Quiagen, Valencia, Calif.). DNase digestion was performed using DNA-free (AM1906; Ambion, Austin, Tex.) and 2 µg of RNA was reverse transcribed using the High Capacity cDNA Kit (4368814; Applied Biosystems, Foster City, Calif.). Taqman gene expression assays were performed in triplicate according to the manufacturer's instructions using the Fast Universal PCR Master Mix (4352042, Applied Biosystems) and the Applied Biosystems 7500 Fast Real-Time PCR System. TaqMan probes specific to individual genes tested for differential expression used (Applied Biosystems. Foster City, Calif.). mRNA expression levels were normalized to GAPDH (Mm99999915_g1; Applied Biosystems) and quantification of relative gene expression, presented as percentage of the relevant baseline, was calculated using the 2^-[delta][delta]CT (comparative threshold) method.

Example 1.13: Western Analysis and ELISA

Western analysis and ELISA carried out in the studies described herein. Tissue samples were homogenized with a 2-ml Tenbroeck tissue grinder (Wheaton, Millville, N.J.) in ice-cold T-PER (Pierce Biotechnology, Rockford, Ill.) in the presence of Halt protease inhibitor cocktail (Pierce Biotechnology) with deacetylase inhibitors for the post-translational modification studies. Lysates were centrifuged at 10,000 rpm for 10 min at 4° C. and supernatants were collected. Twenty to thirty micrograms of clarified protein extract were analyzed by Western blot using an affinity-purified, rabbit polyclonal antisera raised against the murine Mut enzyme at a dilution of 1:1,000. The Complex III subunit Core 2 monoclonal antibody was used as a loading control at a dilution of 1:3,000 (MS304; MitoSciences, Eugene, Oreg.). Horseradish peroxidase labeled anti-rabbit IgG (NA934VS; Amersham Biosciences, Piscataway, N.J.) or anti-mouse IgG (NA931VS; Amersham) were used as the secondary antibody at a dilution of 1:10,000 or 1:30,000, respectively. Signal was visualized using the SuperSignal West Pico chemiluminescence substrate (34080; Thermo Scientific, Rockford, Ill.).

Plasma FGF21 concentrations (pg/ml) were measured by quantikine ELISA (DF2100 for human and MF2100 for the mouse assay, R&D Systems). Specimens, standards and reagents were prepared according to the manufacturer's instructions. All samples were measured in duplicate. Samples above 4,000 pg/ml were diluted 10, 20 and 40× to achieve levels within the reference range. Normal levels according to the manufacturer are for human heparin plasma mean=186 pg/ml, (N=35, range ND-1012), while for mouse heparin plasma concentrations was 877 pg/ml (N=20, range 283-2280).

Example 1.14: Histology, Immunohistochemistry and Electron Microscopy

Histology, immunohistochemistry and electron microscopy carried out in the studies described herein. Tissues were fixed in 10% formalin, embedded in paraffin, sectioned, stained with hematoxylin and eosin following standard procedures (Histoserv), and examined by light microscopy. Sections of white fat, inguinal or subcutaneous were stained for UCP1 (ab-23841; Abeam) for immunohistochemistry, following the manufacturers' instructions [Ready-to-Use Vectastain Universal ABC Kit (Vector Labs)]. Tissue slides were analyzed with an Olympus microscope at a 200× magnification. Transmission electron microscopy was performed on tissues fixed at 4° C. in 2% glutaraldehyde in 0.1M cacodylate buffer (pH 7.4). The tissues were fixed with 2% $OsO_4$ for 2 h, washed again with 0.1M cacodylate buffer three times, subsequently washed with water and placed in 1% uranyl acetate for 1 h. The tissues were serially dehydrated in ethanol and propylene oxide and embedded in EMBed 812 resin (Electron Microscopy Sciences, Hatfield, Pa., USA). Thin sections, 80 nm thick, were obtained by utilizing an ultramicrotome (Leica, Deerfield, Ill., USA) and placed onto 300 mesh copper grids and stained with saturated uranyl acetate in 50% methanol and then with lead citrate. The grids were viewed in the JEM-1200EXII electron microscope (JEOL Ltd, Tokyo, Japan) at 80 kV and images were recorded on the XR611M, mid mounted, 10.5 Mpixel, CCD camera (Advanced Microscopy Techniques Corp, Danvers, Mass., USA).

Example 1.15: Statistical Analyses

Statistical analyses carried out in the studies described herein. All data were recorded and prepared for analysis with standard spreadsheet software (Microsoft Excel). Statistical analysis was completed using Microsoft Excel, Prism 5 (GraphPad), or IBM SPSS Version 21 statistical software. Data are presented as the means±SEM with at least three animals or subjects. When applicable, a two-tailed Student t-test or one-way ANOVA was performed followed by Bonferroni or Tukey-Kramer post hoc test for multiple comparisons. Kruskal-Wallis one-way ANOVA testing was used when groups were of different sizes. Pearson's correlation coefficient and linear regression were used to establish correlations and Kaplan-Meier analyses were performed on survival. Pearson's correlation coefficient and linear regression were employed for correlations. A P value of less than 0.05 was considered significant.

Figure 1B:
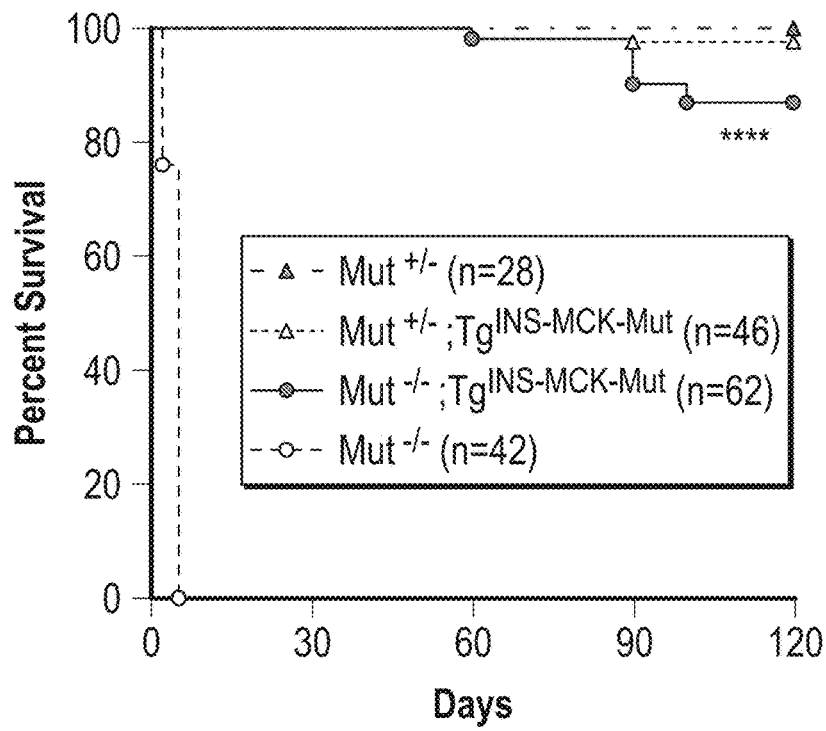
Figure 1C:
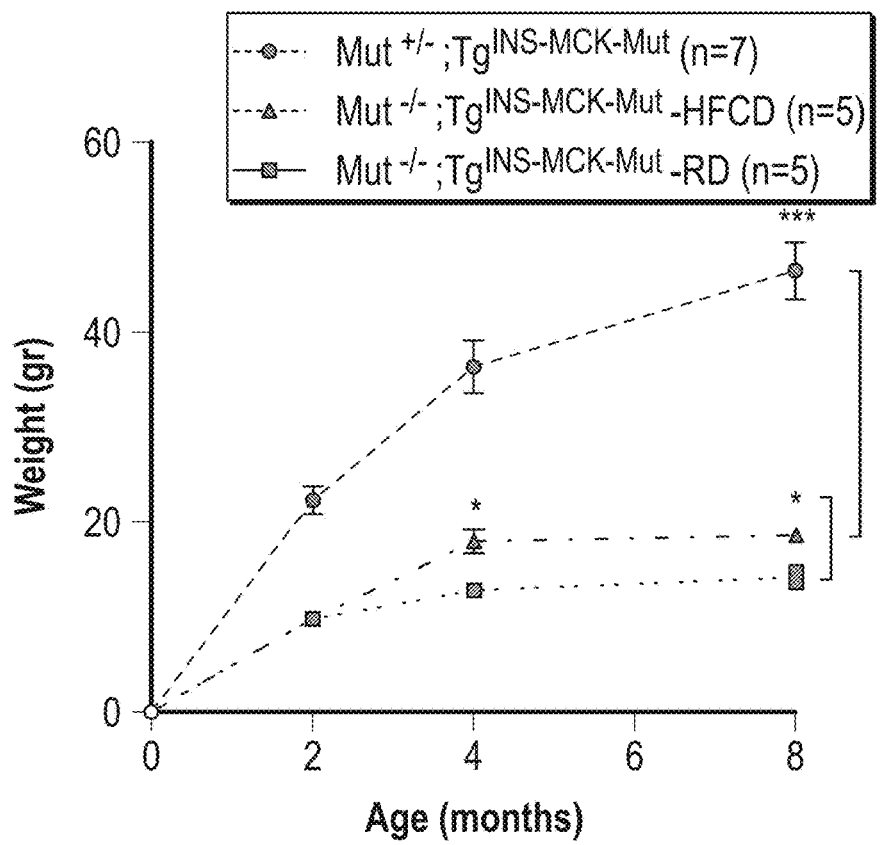
Figure 1D:
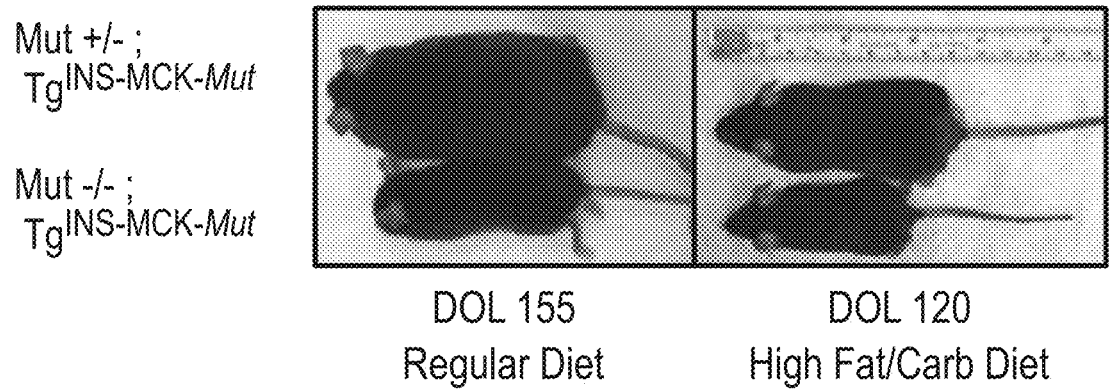
Figure 1E:
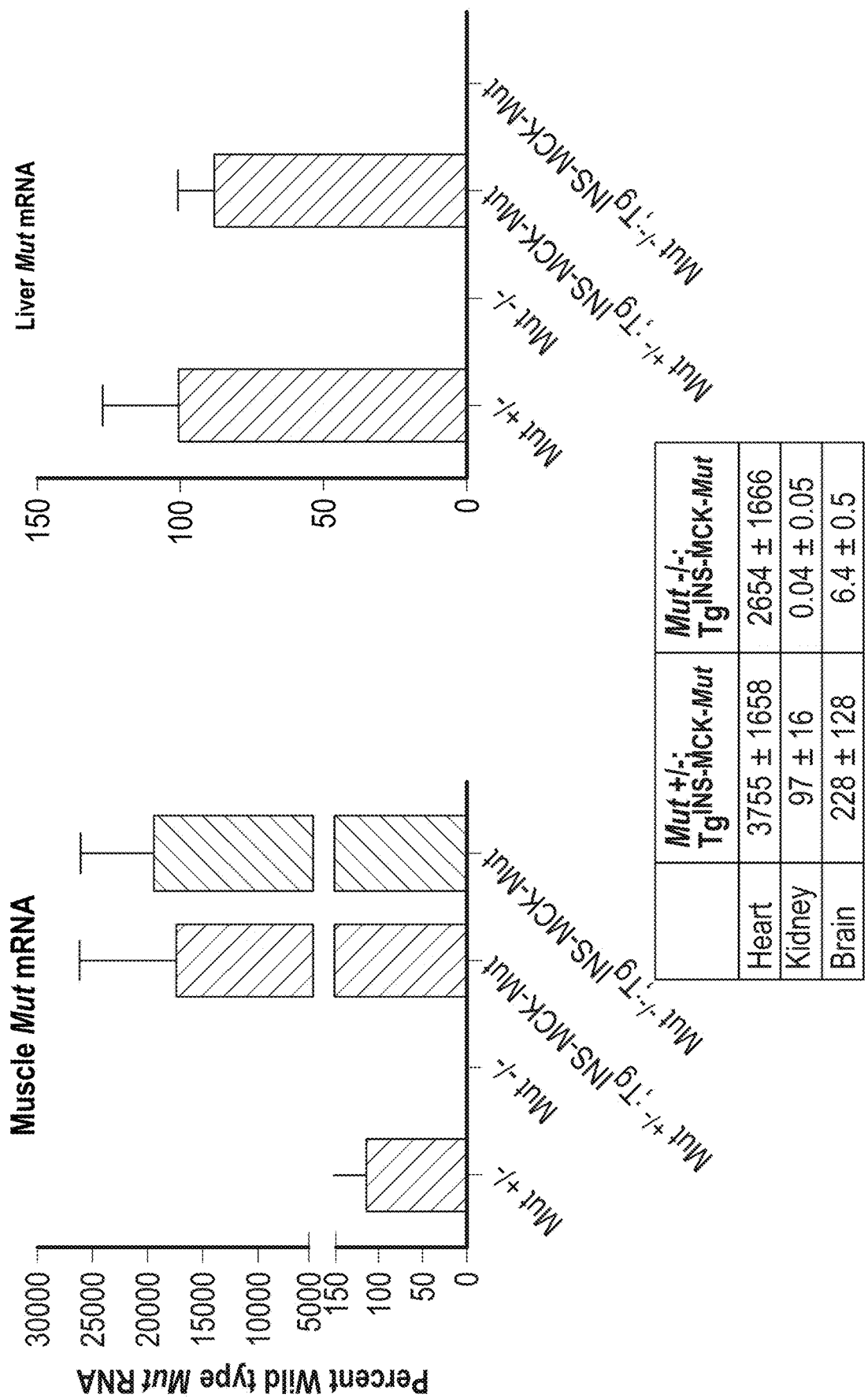
Figure 1F:
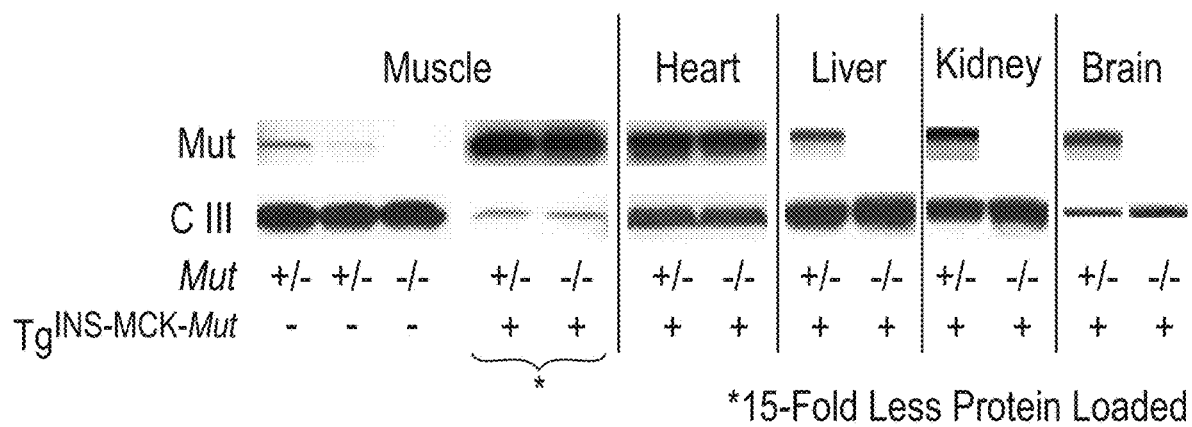

Example 2: Skeletal Muscle Expression of Mut Rescues $Mut^{-/-}$ Mice from Neonatal Lethality and Serves as a "Metabolic Sink" for Circulating Metabolites A construct was designed to express the murine Mut gene under the control of an insulated muscle creatine kinase (MCK) promoter (FIG. 1A). Transmitting founder lines were generated on a C57BL/6 background, C57BL/6 $Tg^{INS-MCK-Mut}$, and bred with C57BL/6 $Mut^{+/-}$ mice. $Mut^{-/-}$; $Tg^{INS-MCK-Mut}$ mice were born in Mendelian proportions and were protected from neonatal lethality, uniformly present in the knockout $Mut^{-/-}$ strain on the same background, with 87% showing survival past day of life 120 (N=62; p=0.001) (FIG. 1B). The $Mut^{-/-}$; $Tg^{INS-MCK-Mut}$ mice showed growth failure and remained smaller than $Mut^{+/-}$; $Tg^{INS-MCK-Mut}$ littermates throughout their lifespan (FIG. 1C). $Mut^{-/-}$; $Tg^{INS-MCK-Mut}$ mice on regular chow diets only achieved weights 25%-30% of their heterozygous littermates (FIG. 1C). Placing the mice on high fat and carbohydrate diets improved their survival and weight gain, though they still only achieved 40-50% of $Mut^{+/-}$; $Tg^{INS-MCK-Mut}$ mice weight, who became obese on the same diet (FIG. 1D). High fat diet is frequently used to alleviate patient phenotype. At 4 months there was a significant difference between average weight on high fat (17.9±1.2 g) and regular chow (12.7±0.6 g) diets (p=0.017). Lack mRNA expression was confirmed in liver and kidney (FIG. 1 E). Abundant immunoreactive MUT was detected solely in skeletal muscle and heart of $Mut^{-/-}$; $Tg^{INS-MCK-Mut}$ mice and with muscle-specific Mut RNA expression at levels comparable to protein expression (FIG. 1F).

Figure 1G:
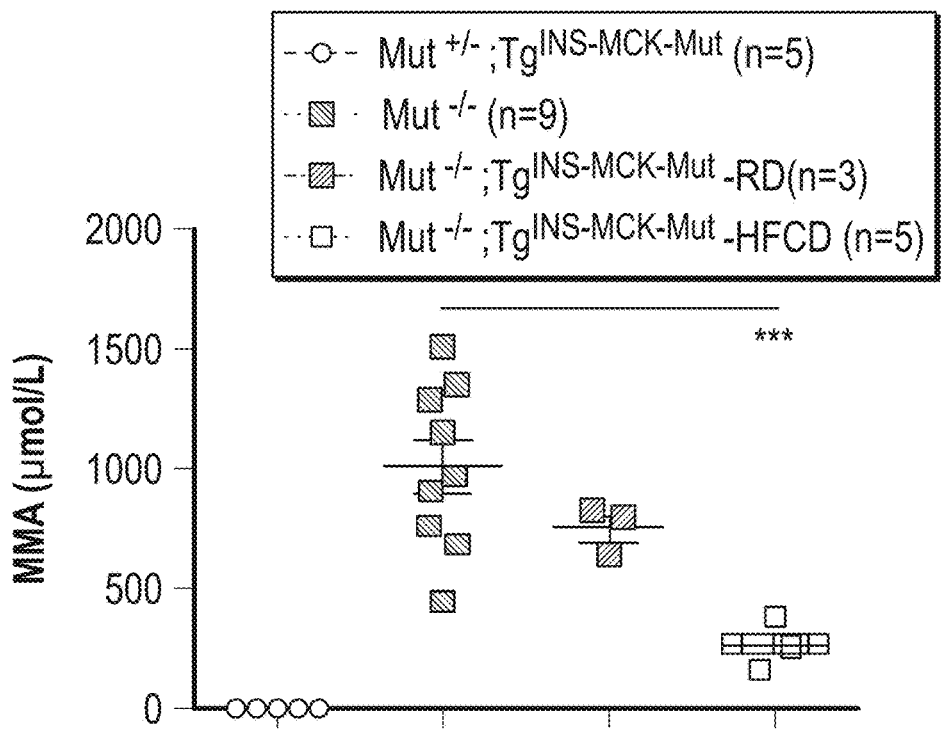
Figure 1H:
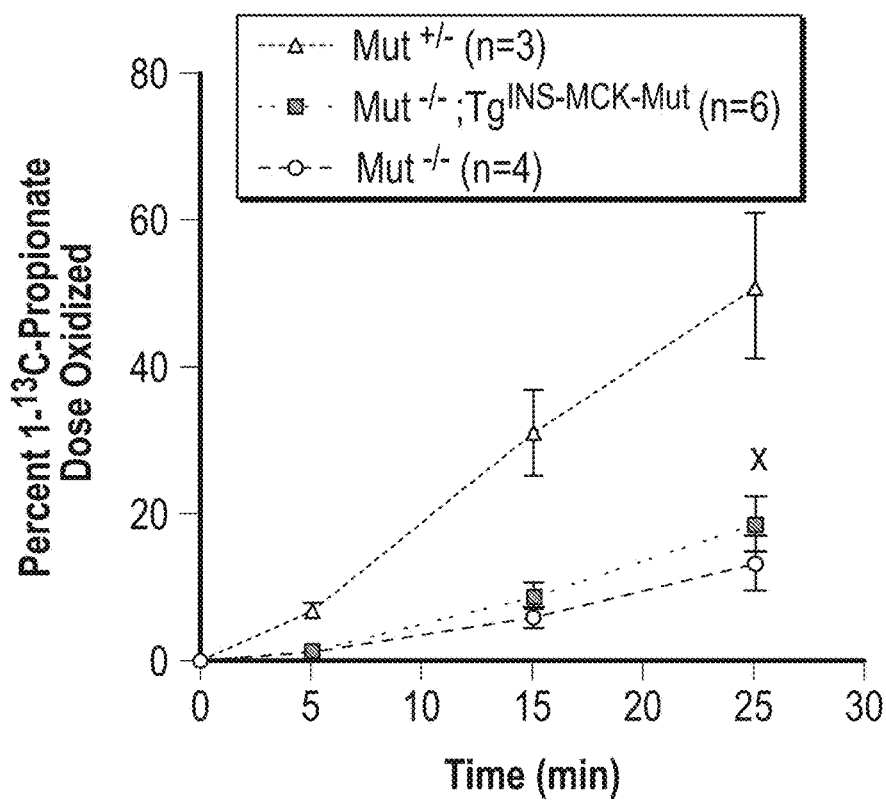

Similar to MMA patients, methylmalonic acid levels were significantly elevated in $Mut^{-/-}$; $Tg^{INS-MCK-Mut}$ mice compared with heterozygous control littermates in both high fat (p=0.001) and regular chow groups (p=0.0001). Baseline plasma MMA levels (µM) were 1107.9±66 in transgenic mice, compared to <5 in controls. $Mut^{-/-}$; $Tg^{INS-MCK-Mut}$ mice on high fat diet had methylmalonic acid levels 35% of those reared on regular chow (p=0.002) (FIG. 1G). To further assess transgene function, the in vivo oxidative capacity of $Mut^{-/-}$; $Tg^{INS-MCK-Mut}$ mice was measured through detecting metabolism of numerous $1-^{13}C$ labeled fatty acids to $^{13}CO_2$ via the Krebs Cycle. Notably, the $Mut^{-/-}$; $Tg^{INS-MCK-Mut}$ mice metabolized 18.4±3.6% of administered $[1-^{13}C]$propionate dose in 25 minutes, compared with 50.7±9.8% in $Mut^{+/-}$ and 13.1±3.7% in $Mut^{-/-}$ (FIG. 1H).

Figure 3B:
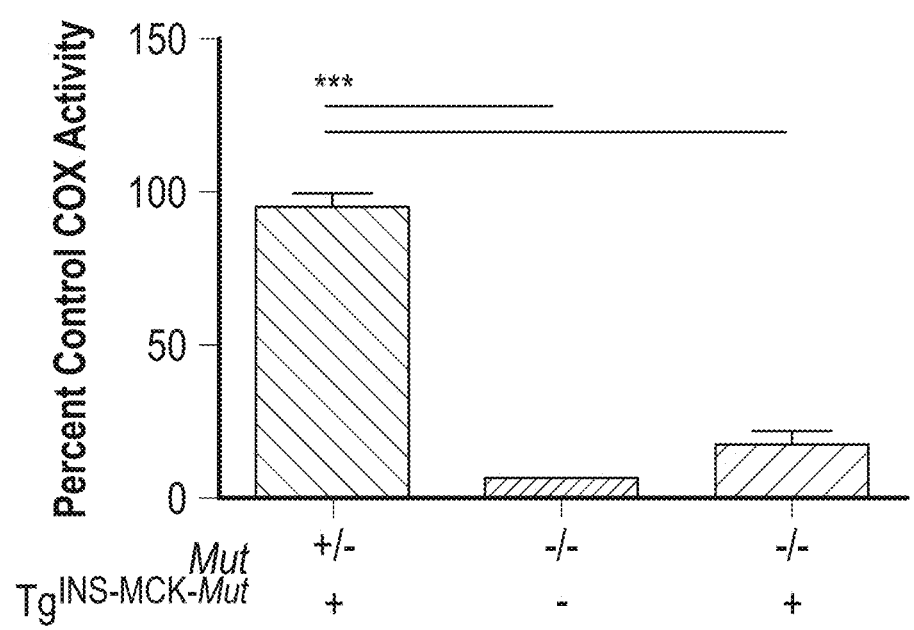
Figure 4A:
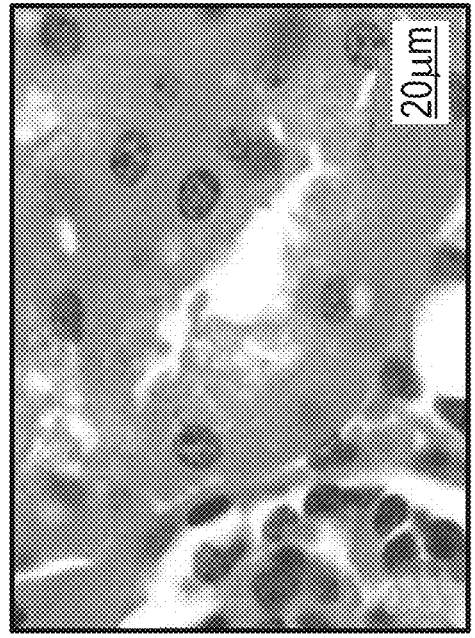
FIGS. 4A-E shows renal tubular histological (FIG. 4A) and ultrastructural changes in Mut$^{-/-}$; Tg$^{INS-MCK-Mut}$ mice (FIG. 4B) compared to a Mut$^{-/-}$; Tg$^{INS-MCK-Mut}$ control (FIG. 4C). Impaired filtration (FIG. 4D) and increased plasma lipocalin 2 (FIG. 4E) accompany the renal disease.
Figure 4B:
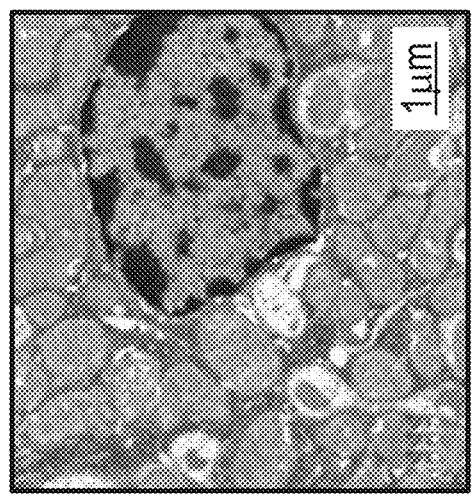
Figure 4C:
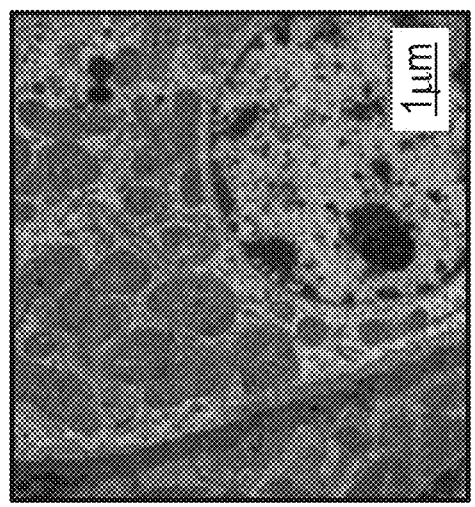
Figure 4D:
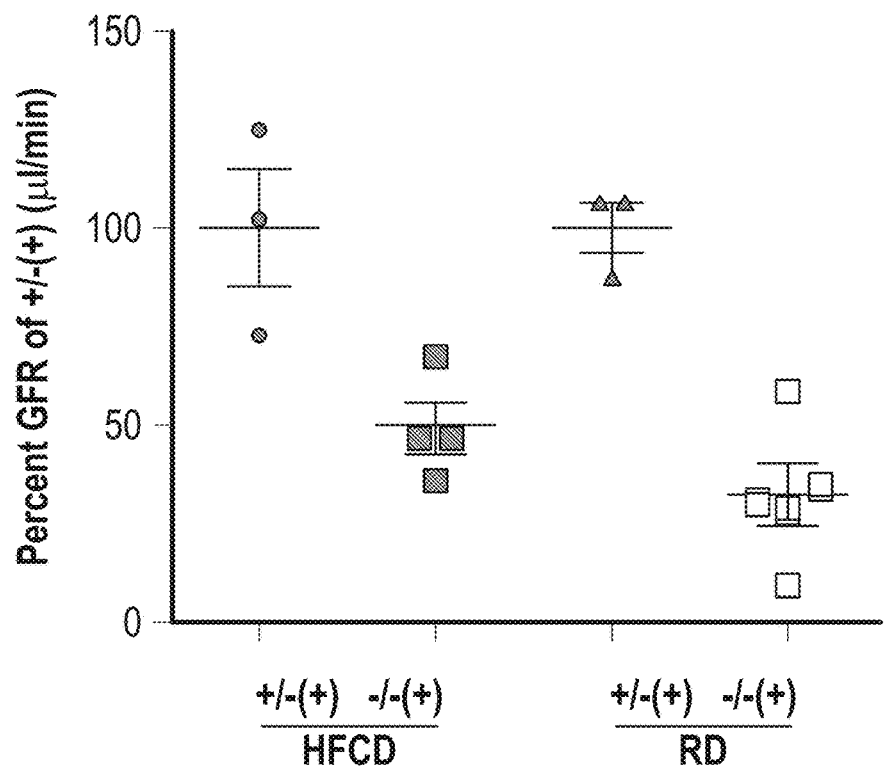
Figure 4E:
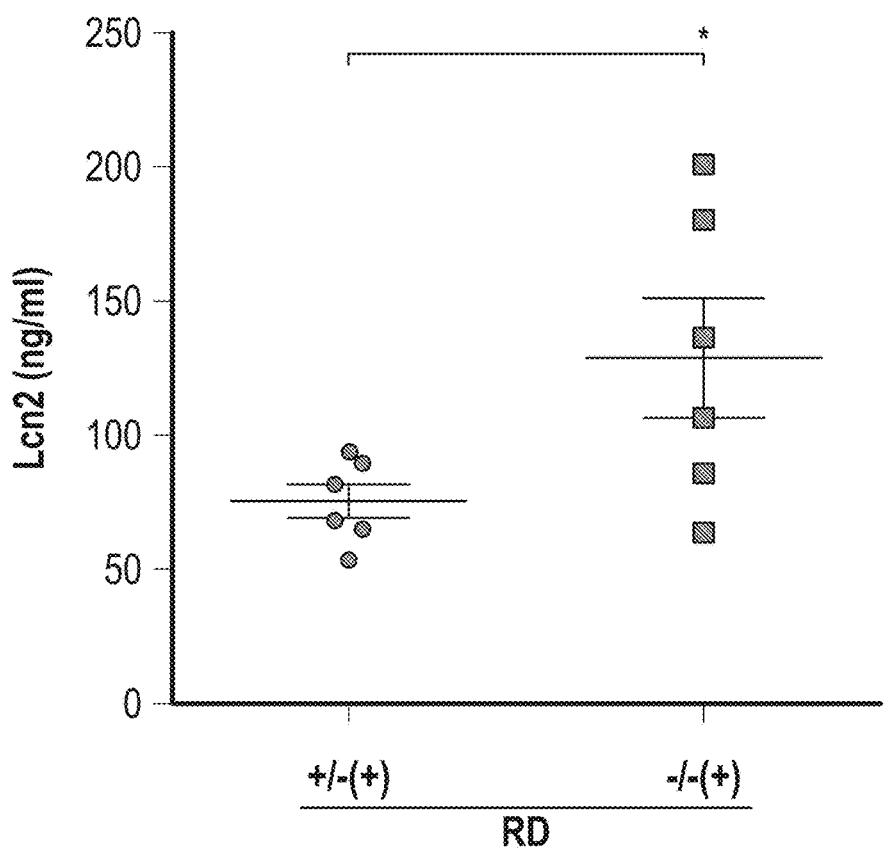

The $Mut^{-/-}$; $Tg^{INS-MCK-Mut}$ animals developed significant liver pathology, characterized by severe diffuse lipidosis, vacuolization of the cytoplasm, and megamitochondria formation, which was associated with decreased respiratory chain complex IV activity (18.2±7.4% relative to controls), similar to the $Mut^{-/-}$ mice (FIG. 2A). Further, electron microscopy of $Mut^{-/-}$; $Tg^{INS-MCK-Mut}$ livers showed mitochondria that are enlarged with shorten and flattened or no cristae (FIG. 2B). Other mitochondria formed a rosette-like pattern that may represent autophagy or mitophagy. These findings resemble changes previously noted in electron microscopy of an MMA patient liver. Control littermates had normal hepatic ultrastructure (FIG. 3C). Cytochrome oxidase (COX) and succinic dehydrogenase (SDH) were both depleted in $Mut^{-/-}$; $Tg^{INS-MCK-Mut}$ mice compared with heterozygous littermates, indicating diminished electron transport chain activity and mitochondrial biogenesis (FIGS. 3A-B). H&E staining showed that $Mut^{-/-}$; $Tg^{INS-MCK-Mut}$ mice kidneys contain large, eosinophilic vacuoles in their proximal tubules (FIG. 3A) and megamitochondria (FIG. 3B). These changes were similar to those seen in MMA patient kidneys (Manoli et al, PNAS, 2013, 13552-13557, Targeting proximal tubule mitochondrial dysfunction attenuates the renal disease of methylmalonic acidemia) but not control littermates (FIG. 3C). Glomerular filtration rate (GFR) measurements, performed in vivo with FITC-inulin, showed that $Mut^{-/-}$; $Tg^{INS-MCK-Mut\ mice}$ had 49% filtration compared with $Mut^{+/-}$; $Tg^{INS-MCK-Mut}$ mice (p=0.02) on high fat diet (FIG. 3D). Similarly on the regular chow, $Mut^{-/-}$; $Tg^{INS-MCK-Mut}$ mice had a filtration rate 32% of that of $Mut^{+/-}$; $Tg^{INS-MCK-Mut}$ mice (p=0.001). GFR measurements between Mut$^{-/-}$; Tg$^{INS-MCK-Mut}$ mice on high fat and regular diets showed no statistical difference (p=0.15) (FIG. 3D). A kidney disease biomarker, lipocalin 2, was measured, as described in prior work (Manoli et al, PNAS, 2013, 13552-13557, Targeting proximal tubule mitochondrial dysfunction attenuates the renal disease of methylmalonic acidemia) and validated in a large MMA patient cohort. Plasma Lcn2 concentrations were significantly elevated in the Mut$^{-/-}$, Tg$^{INS-MCK-Mut}$ mice compared to their heterozygote littermates (P=0.04), and correlated with the GFR measurements (FIG. 2E), further validating the reduced GFR measured and the validity of Lcn2 as a renal biomarker in MMA.

Selective muscle expression of the Mut enzyme by transgenesis at levels matching or exceeding the heterozygous controls in the skeletal and cardiac muscle resulted in near uniform rescue of the neonatal lethal phenotype of the Mut$^{-/-}$ mice, but was unable to prevent liver and kidney damage.

Severe hepatorenal pathological changes in the Mut$^{-/-}$; Tg$^{INS-MCK-Mut}$ animals replicate the hepatic and renal pathology seen in MMA patients.

Example 3: Identification of Hepatic Biomarkers in MMA

Mice that express the Mut gene under the control of an insulated, muscle creatine kinase promoter (Mut$^{INS-MCK-Mut}$) were generated. Mut$^{-/-}$; Tg$^{INS-MCK-Mut}$ mice were rescued from the neonatal lethality of the Mut$^{-/-}$ mice and showed an attenuated metabolic phenotype. They exhibited growth failure, hepatic mitochondriopathy, renal dysfunction and were resistant to obesity when fed a high caloric diet. A fasting challenge in mice was used to dissect the stress response characterizing the metabolic decompensations in patients and probed the hepatic adaptions using transcriptomics.

Figure 5A:
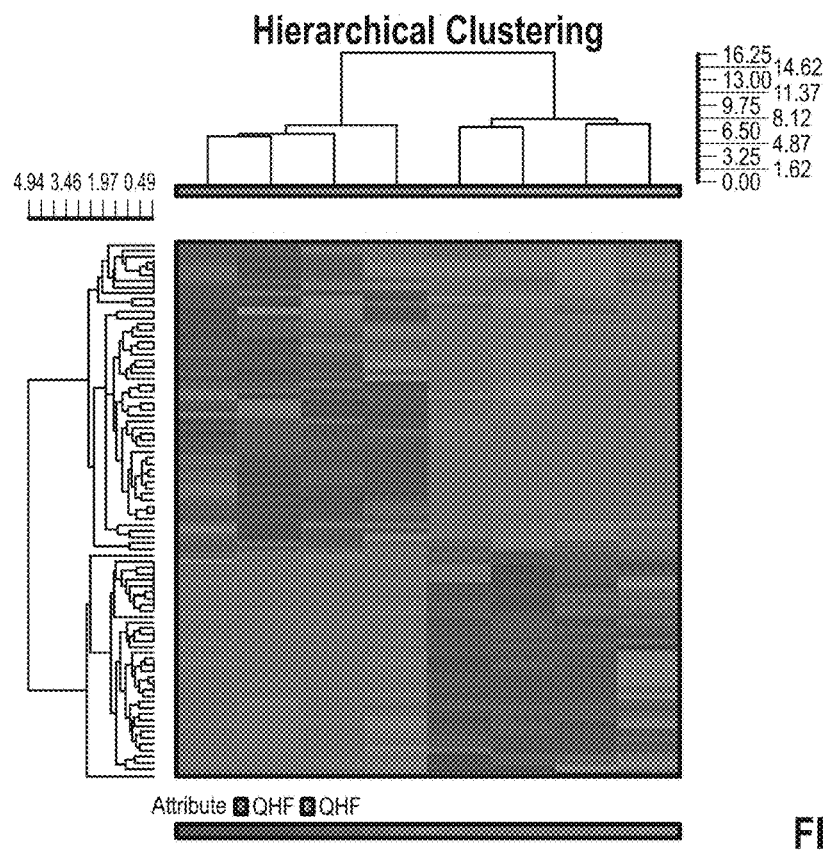
FIGS. 5A-B shows hepatic transcriptomic analysis of Mut$^{+/-}$; Tg$^{INS-MCX-Mut}$ and Mut$^{-/-}$; Tg$^{INS-MCK-Mut}$ mice shows apparent separation between groups and conditions (FIG. 5A), when selecting genes that are 2.5 fold differentially expressed. One candidate, Fgf21, was validated using qPCR (FIG. 5B).

Fasted Mut$^{-/-}$; Tg$^{INS-MCK-Mut}$ mice developed hypoglycemia and abberant hepatic gene expression of many genes (FIG. 5A), including a key circulating metabolic regulator, FGF21. Significant enrichment of MMA related hepatic metabolic adaptations was identified (Table 1, below). Some pathways are involved in immune/inflammatory responses, including the LPS/IL-1-mediated Inhibition of RXR function pathway (Gstm3, Fmo3, Fabp5, CPT1B, Cyp2a12, Abcc4) that downregulates hepatic genes involved in metabolism; transport and/or biosynthesis of lipid, cholesterol, bile acid and organic anion/xenobiotics during infection; and inflammation or injury through the secretion of IL1 and TNF in different cell types, especially in macrophages. Additional pathways and genes that differed between mutant and heterozygote mice at fasting were: acute phase response and complement system signaling (Orm1, Saa4, Socs2, Saa2, C9, C6), fatty acid metabolism (Cyp2B13/9, Cpt1B, Cyp2A12/22), steroid metabolism (Hsd3b1, Cyp7b1) and cell cycle regulation/cancer signaling (Myc, Ccnd1). A list of selected up- and downregulated pathways associated with MMA related hepatic metabolic adaptations is presented in Table 1.

The identified genes showed a dissimilar response to fasting between heterozygote and mutant mice and performed quantitative qRT-PCR in tissues from both male and female animals to be able to be used to study gender specific effects, because of previous gender-specific findings in microarrays from the liver-transgenic mouse model kidneys. Table 2, below, presents a list of genes that were 2.5 fold or more dysregulated between the Mut$^{-/-}$; Tg$^{INS-MCK-Mut}$ mice and control littermates, in the fasting state. Table 3, below, presents a list of genes that were 2.5 fold or more dysregulated between the Mut$^{-/-}$; Tg$^{INS-MCK-Mut}$ mice and control littermates, at baseline. Select genes were validated by RT-PCR as shown in bold in Tables 2 and 3. The results of the RT-PCR are illustrated at FIGS. 6A-L.

Figure 5B:
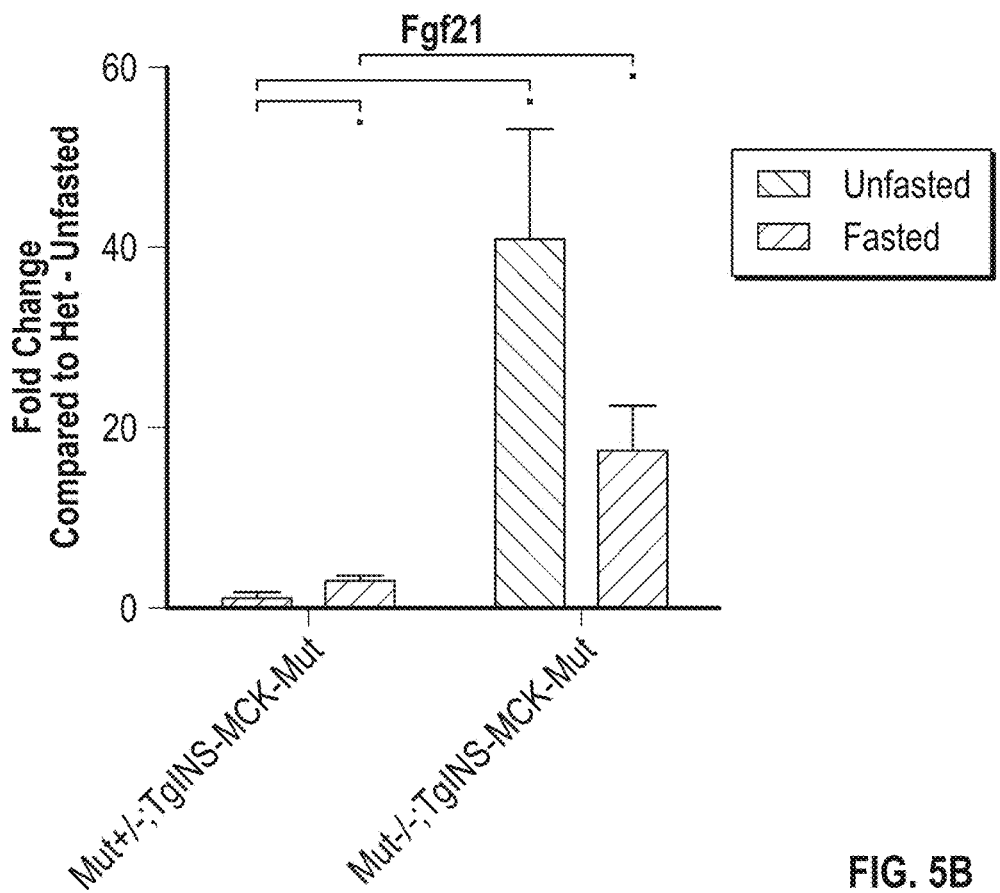

The gene that showed the most divergent response to fasting in the Mut$^{-/-}$; Tg$^{INS-MCK-Mut}$ mice was Fgf21. Fgf21 showed a 41.23±23.8% higher mRNA expression in the liver of the Mut$^{-/-}$; Tg$^{INS-MCK-Mut}$ compared to heterozygote and wild type controls, while instead of showing an induction with fasting, like the heterozygote animals (3.3±0.53% control from 1.25±0.9), the showed a lower than baseline expression (17.5±9.5% control, down from 41.23±23.8) (FIG. 5B).

Figure 6A:
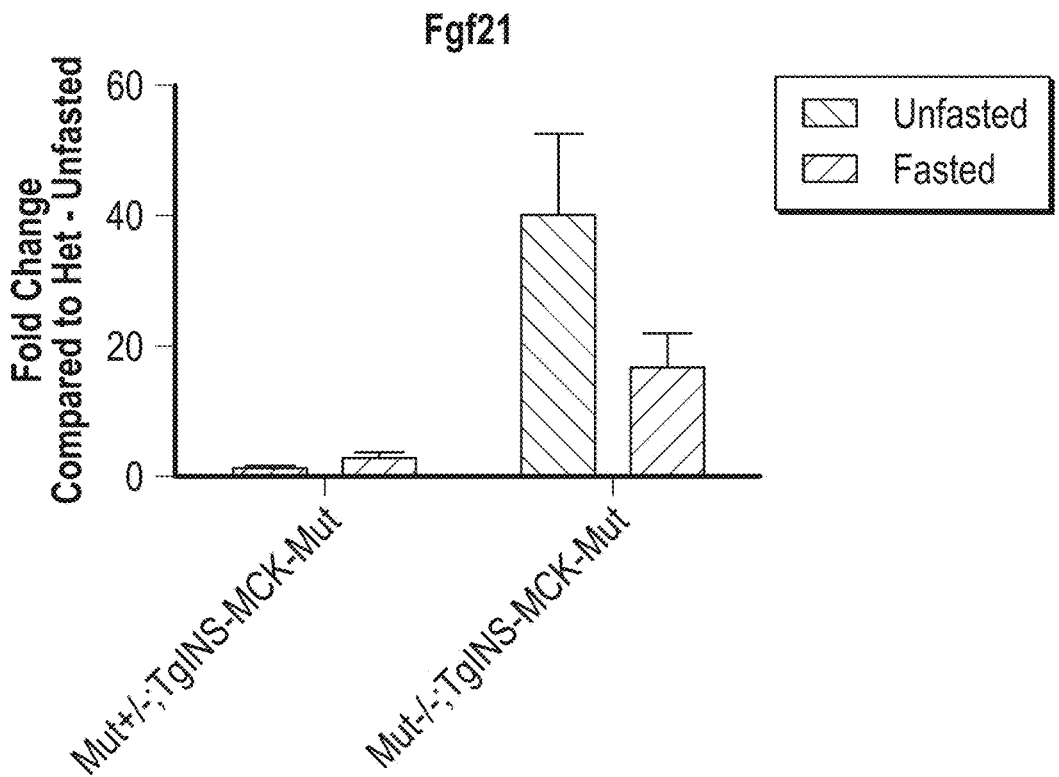
FIGS. 6A-L shows validation by qPCR of key metabolic enzymes that are differentially expressed in MMA. Upregulated (FIGS. 6A-I) and downregulated (FIGS. 6J-L).
Figure 6B:
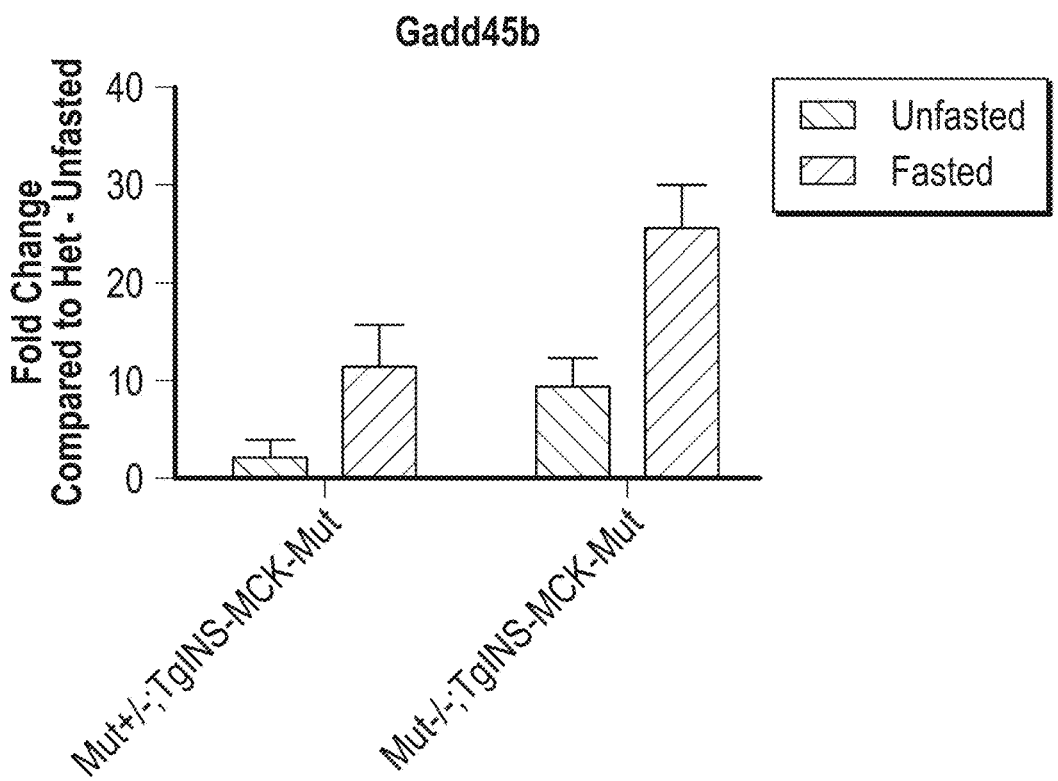
Figure 6C:
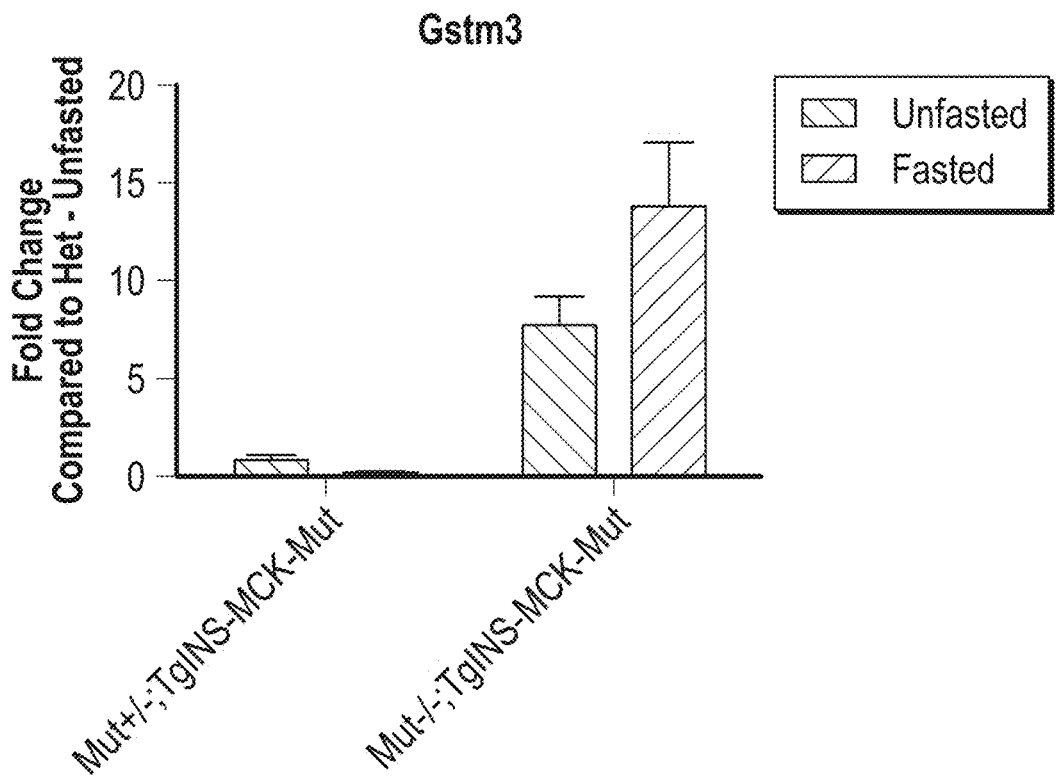
Figure 6D:
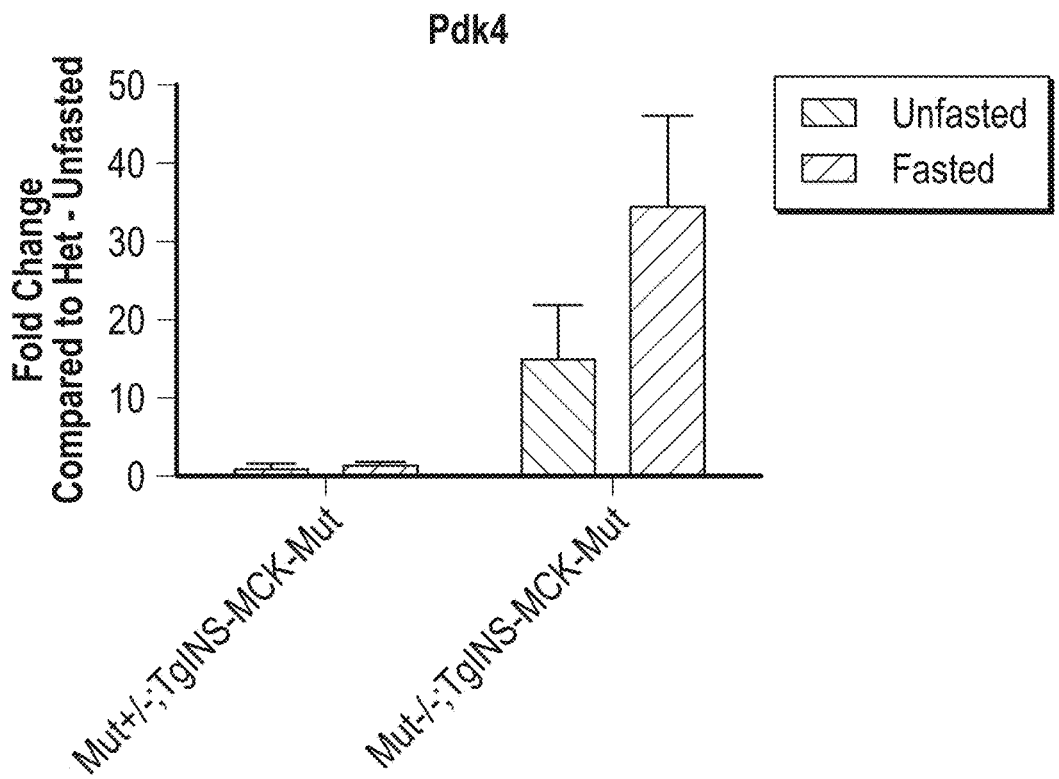
Figure 6E:
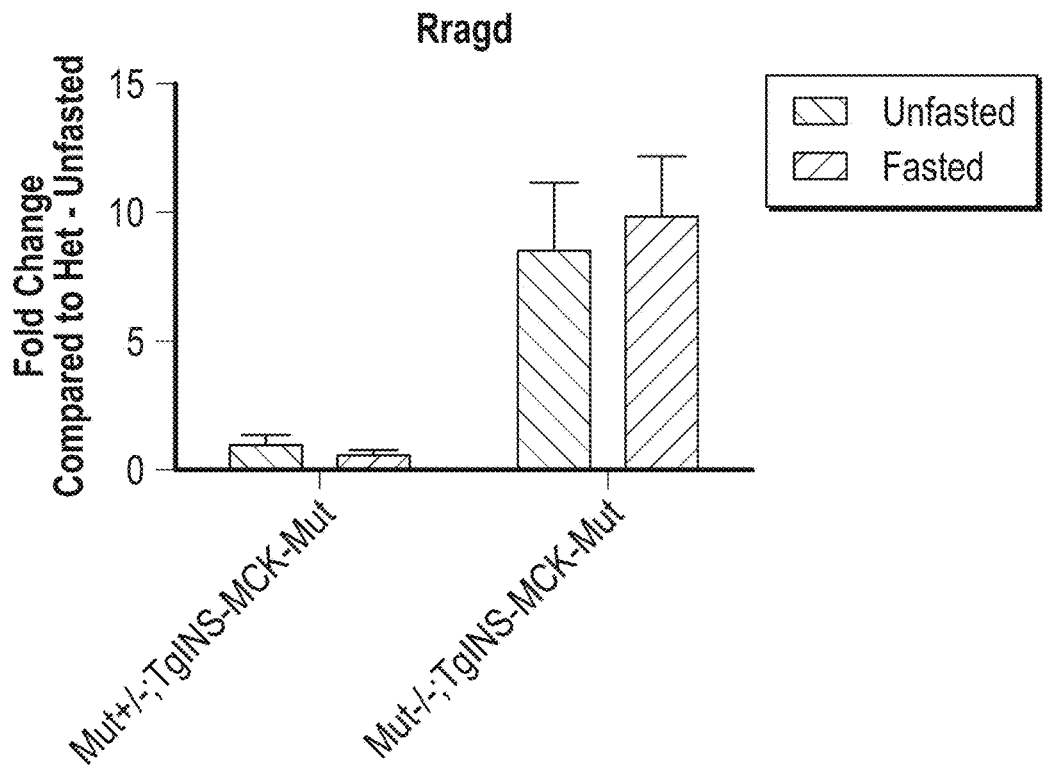
Figure 6F:
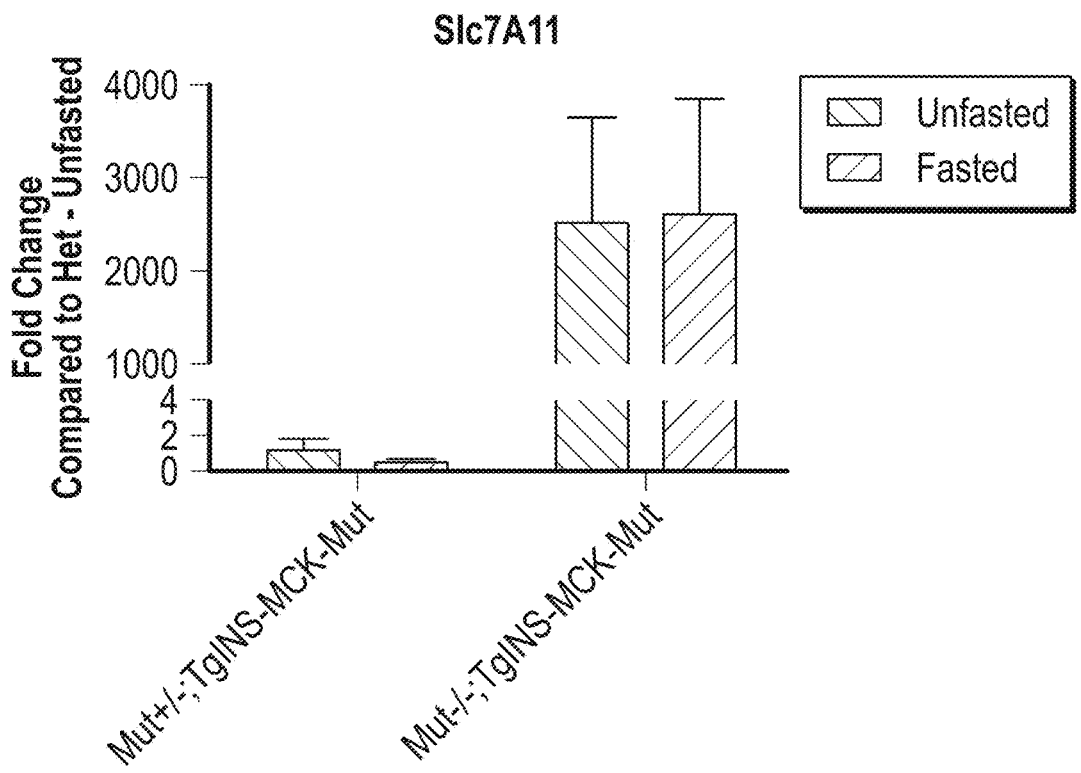
Figure 6G:
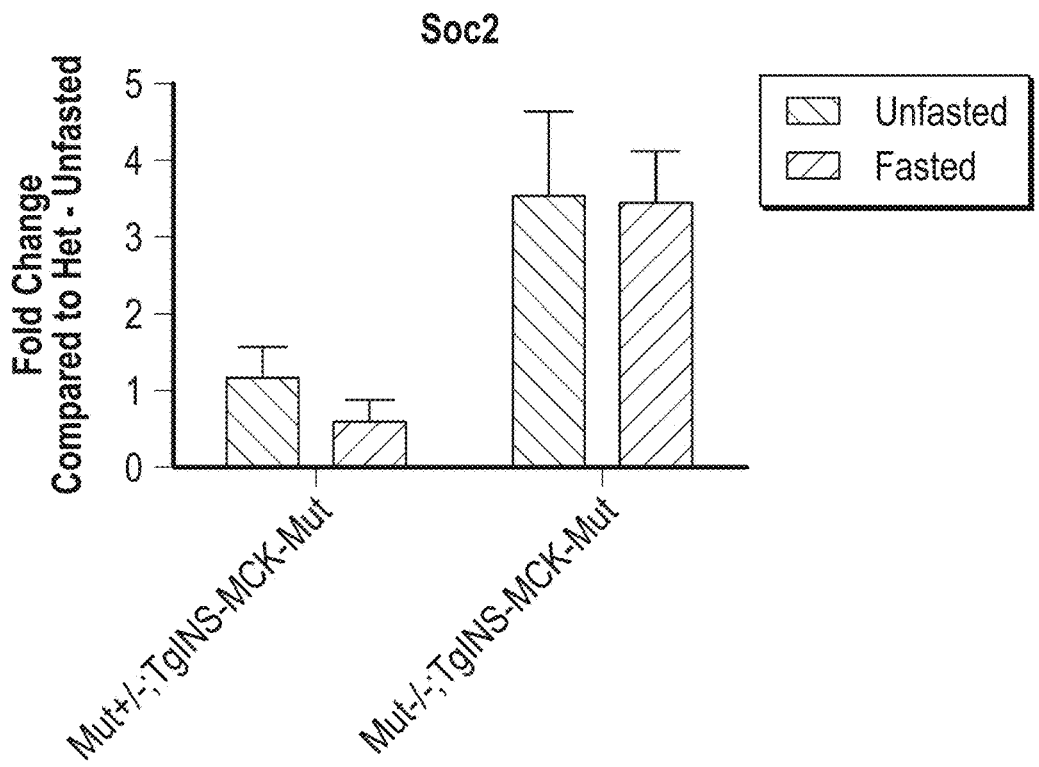
Figure 6H:
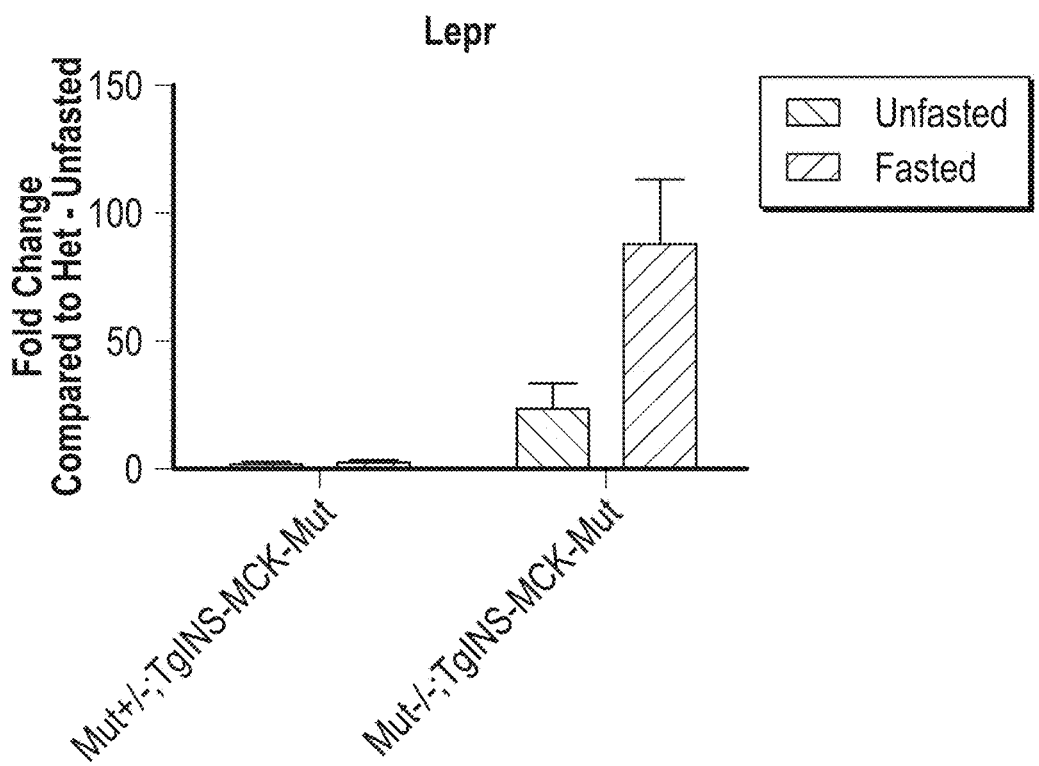
Figure 6I:
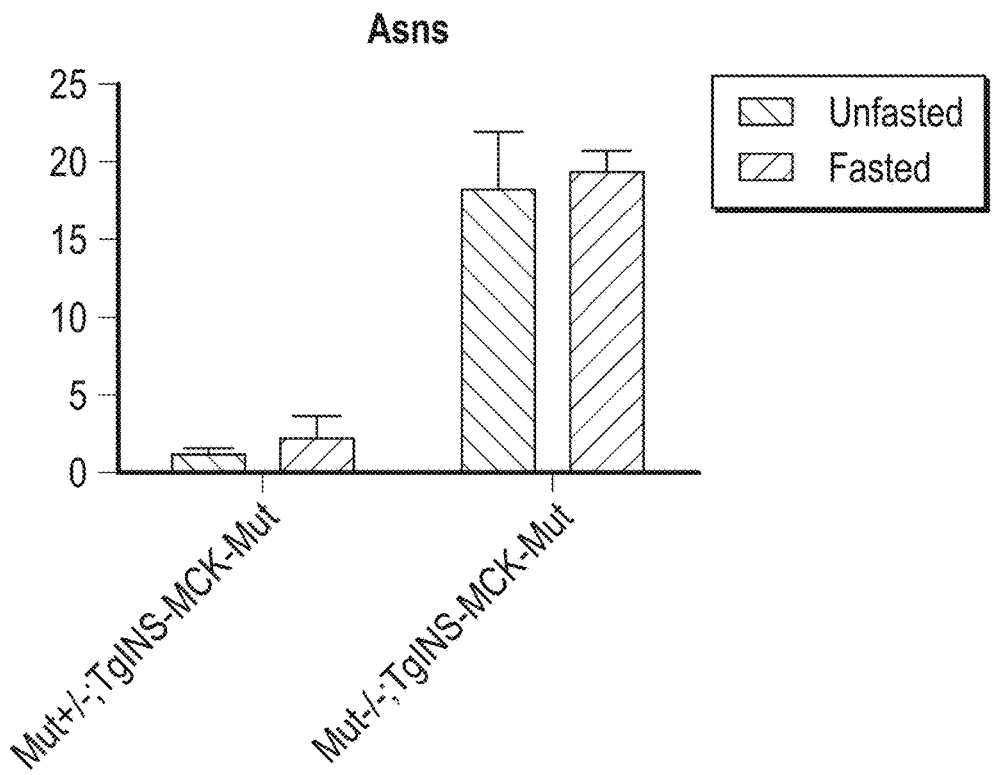
Figure 6J:
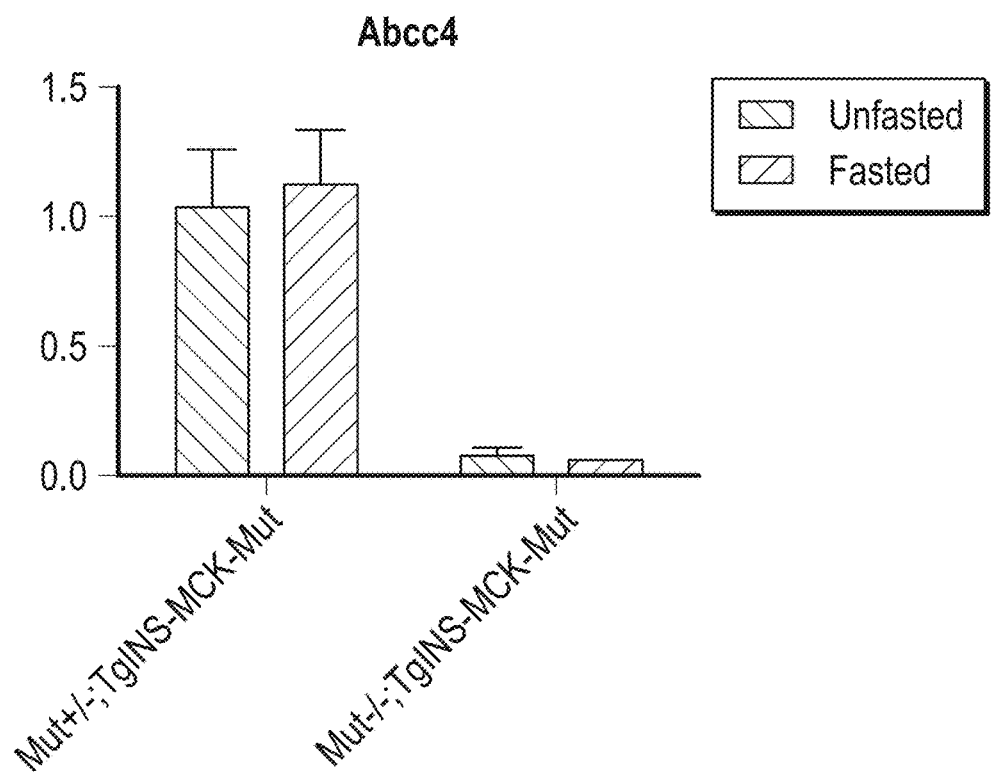
Figure 6K:
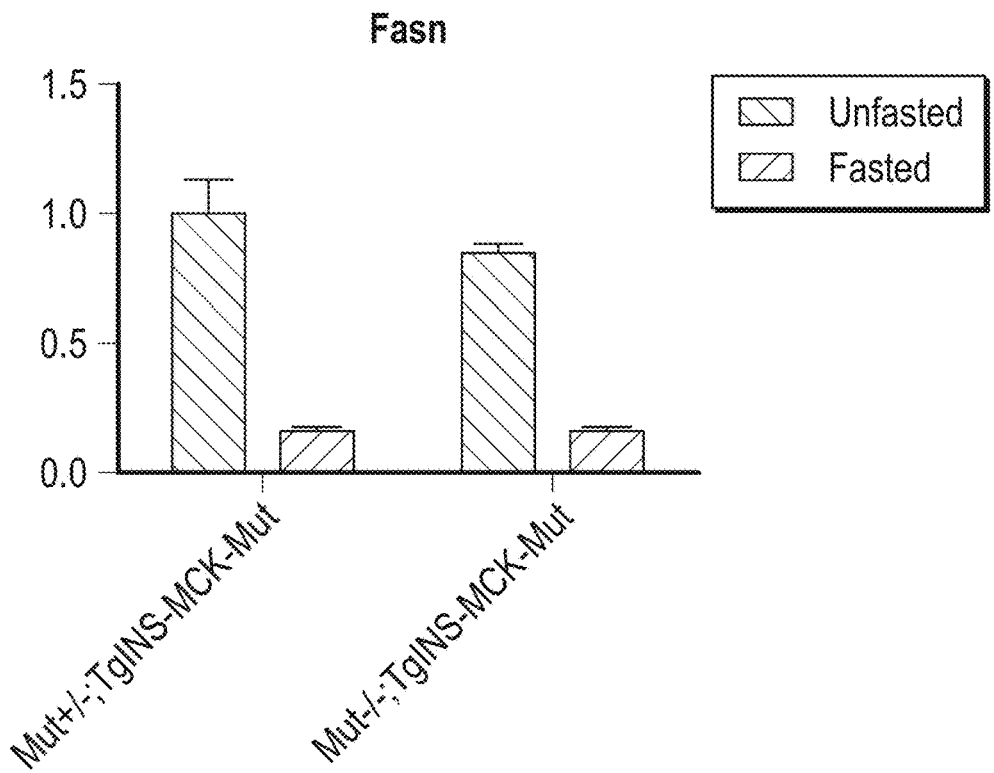
Figure 6L:
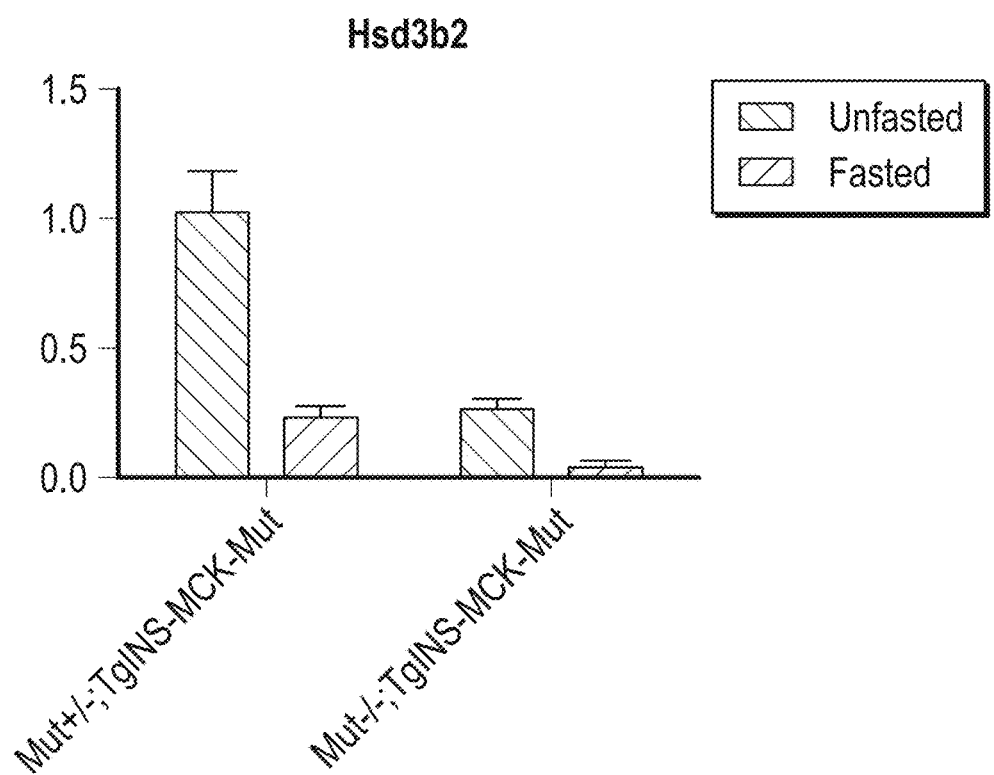

Other biomarkers were also validated for differential expression, including Gadd45b (FIG. 6B), Gstm3 (FIG. 6C), Pdk4 (FIG. 6D), Rragd (FIG. 6E), Slc7A11 (FIG. 6F), Asns (FIG. 6I) and Abcc4 (FIG. 6J), Fasn (FIG. 6K), and Hsd3b2 (FIG. 6L). These genes and proteins play critical roles in intermediary metabolism but have not been identified as being associated with MMA. Several of the dysregulated genes are targets of the AMP-activated kinase (AMPK), sirtuin 1 (SIRT1), PPAR-gamma coactivator alpha (PGC-1alpha), peroxisome proliferator-activated receptor alpha (PPARalpha), and sterol regulatory element-binding protein 1 (SREBP-1), pathways that have well studied roles in non-alcoholic fatty liver disease (NAFLD) and non-alcoholic steatohepatitis (NASH).

Gene expression profiling on liver tissues at the fasted state showed differential clustering in a number of pathways, with significant enrichment in genes involved in immune/inflammatory responses and the liver drug metabolism pathways, consisting of phase I or II enzymes involved in the detoxification and elimination of endogenous or exogenous compounds, i.e. organic acids, xenobiotics, steroid/bile acid biosynthesis. Cytochrome P450 (CYP) enzyme system related genes, including Cyp2A12, Cyp2A22, Cyp2B9, Cyp2B13, as well as Gstm3, encoding glutathione S-transferase involved in detoxification of environmental toxins by conjugation to glutathione and Fmo3—flavin-containing monooxygenase were significantly upregulated, likely to process the massive flux of endogenous toxins accumulating as a result of the block in the organic acid metabolic pathway. On the other hand, synthetic pathways including bile acid and steroid biosynthesis including Cyp8B1, Cyp7B1, Cyp11B1, Hsd3b2, 3 and 5 or fatty acid metabolism, like Elovl3, Acnat2, involved in peroxisomal lipid metabolism were suppressed.

A significant induction of genes involved in rate-controlling steps in both lipid and glucose metabolism were also observed, Cpt1B and Pdk4, respectively, indicating an exaggerated switch to lipid catabolism when glucose is sparse.

Gstm3, a glutathione S-transferase important in the detoxification by conjugation with glutathione of environmental toxins, drugs, carcinogens and oxidative stress products, was a gene that instead of being downregulated with fasting, it was highly upregulated both at baseline and after fasting in the Mut$^{-/-}$; Tg$^{INS-MCK-Mut}$ mice.

In aggregate, these differentially regulated genes serve as hepatic biomarkers of MMA.

To further explore Fgf21 as an MMA associated disease biomarker, and as an outcome parameter for future human treatment studies, we used mouse models to interrogate the influence of hepatic Mut expression on plasma Fgf21 levels via germ line transgenesis or gene addition. We first compared the Mut$^{-/-}$; Tg$^{INS-MCK-Mut}$ Fgf21 concentrations to those measured in the liver transgenic mice (Tg$^{INS-Alb-Mut}$).

Figure 15:
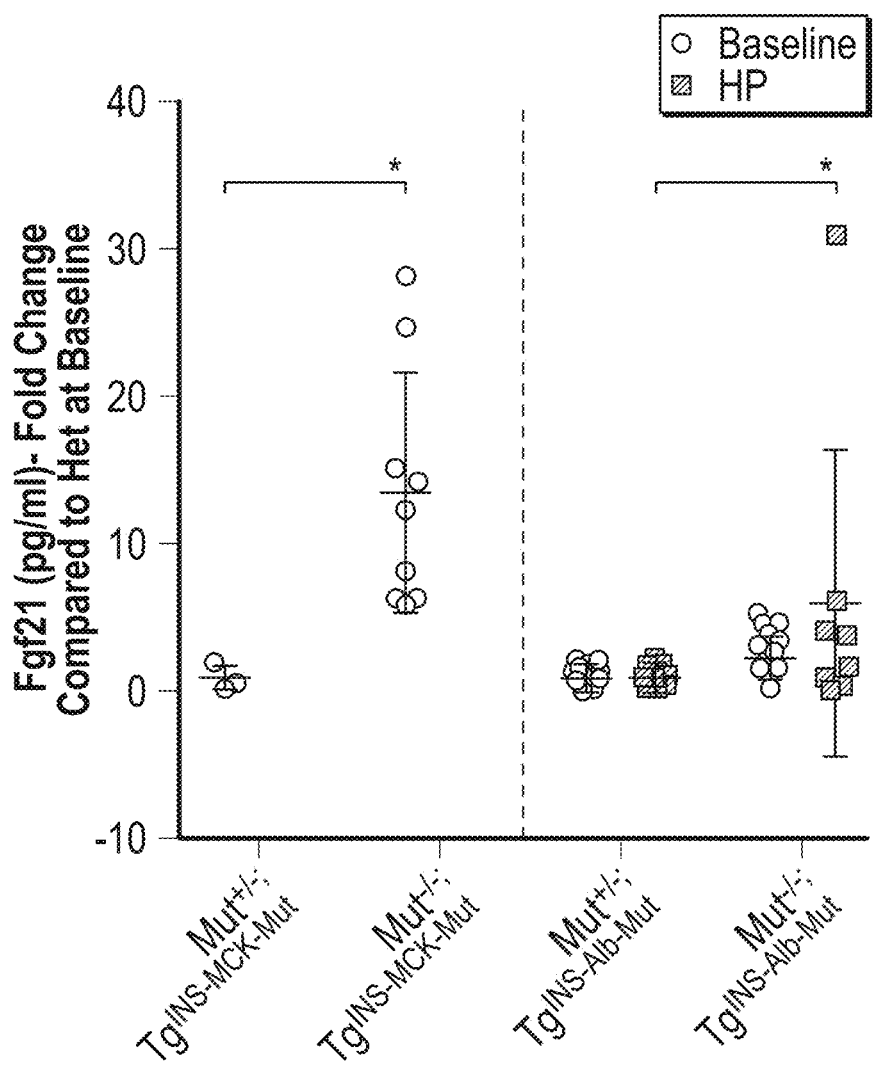
FIG. 15 shows liver transgenic animals, Mut$^{-/-}$; Tg$^{INS-Alb-Mut}$ display milder elevations in plasma Fgf21 concentrations (2.282±0.337-fold higher than their heterozygote littermates, n=21 and 19 respectively, P=NS), that were relatively unaffected by high protein challenge, except for a sick male mutant animal (6.07±3.62-fold higher than controls, n=8, P=NS).

Liver transgenic mice had minimal elevations of plasma Fgf21 compared to the muscle transgenic animals. Moreover, Fgf21 plasma concentrations remained largely unchanged (except for one sick outlier male mouse) even after a 2-month high protein challenge, a dietary treatment that induces massive plasma metabolite elevations with an accompanying significant decline in renal function in these mice (FIG. 15).

Example 4: Validation in MMA Patient Plasma: FGF21 Concentrations are Higher in More Severe Patients and Display Correlations to Clinically Important Patient Parameters It was particularly important to discover Fgf21, a key metabolic regulator with antihyperglycemic, antihyperlipidemic, and thermogenic properties, amongst the most significantly dysregulated genes in the Mut$^{-/-}$; Tg$^{INS-MCK-Mut}$ liver microarray analysis.

Human FGF21 is a 181-amino acid peptide (~22.3 kDa) derived from a 208-amino acid mature protein encoded by the FGF21 gene located in chromosome 19. It is highly conserved and there is nearly 80% homology with the rodent gene. Unlike other FGFs, FGF21 lacks heparin binding, and can therefore serve in an endocrine, autocrine and paracrine fashion.

From the large array of dysregulated pathways observed in the microarray experiments, Fgf21/FGF21 was chosen as a promising target for further studies, given its central role in mitochondrial metabolism. Moreover, immunoassays are readily available for measurement of plasma concentrations in both mice and patients.

Consistent with the microarray and qPCR experiments, significantly elevated Fgf21 plasma concentrations were measured in Mut$^{-/-}$; Tg$^{INS-MCK-Mut}$ mice at different ages ranging from 1,000-7,000 pg/ml, 2,767±2,264 (mean±SD, normal<200).

Figure 7A:
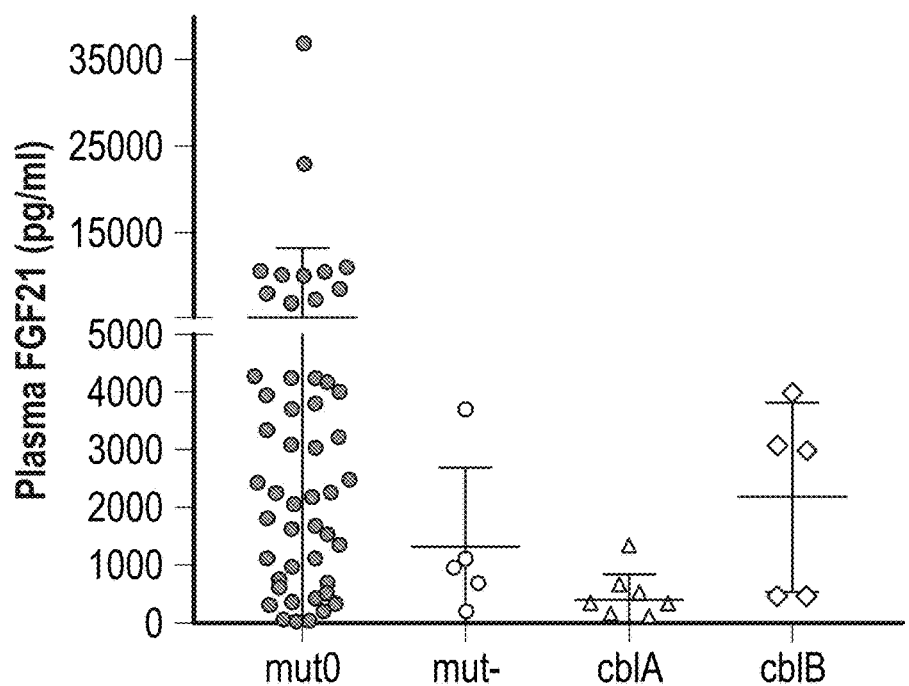
FIGS. 7A-E shows FGF21 concentrations in the plasma from different classes of isolated MMA patients (FIG. 7A). There is no correlation between FGF-21 and markers of renal disease (FIG. 7B). FGF21 correlates with height and head circumference (OFC) (FIG. 7C) and markers of oxidative stress including glycine and alanine (FIG. 7D) and urinary isoprostanes (FIG. 7E).

A survey of FGF21 concentrations in the patients with MMA was undertaken. Massively elevated FGF21 plasma concentrations were confirmed in a large MMA patient cohort. 72 patients with various MMA subtypes (49 with the mut subtype, 6 with cblB and 8 with cblA) were tested, from 1-5 samples per patient obtained at different clinic visits, mostly during the well state. Total 104 FGF21 measurements were performed to study the natural history and response to illness/decompensation (FIG. 7A). FGF21 plasma concentrations corresponded to the disease subtype severity, with the lowest concentrations observed in patients with the B12-responsive cobalamin A defect and highest levels in two patients prior to liver transplantation (FIG. 7A), one of whom had severe pathology of liver mitochondrial ultrastructure.

Concentrations of FGF21 in patients were massively elevated in the mut0 MMA patients (228.3-41,371.06 pg/ml, mean±SD: 7,139±9,462), as compared to cblB MMA (2,206±1621) and the milder B12-responsive MMA subtype, cblA (330.7±214.6, P=0.002, one-way ANOVA) (FIG. 7A). Heterozygote parental control samples in comparison were 73.6±58.94 pg/ml. These values in MMA patients are much higher than those previously reported in studies of children and adults with mitochondrial myopathies, nonalcoholic fatty liver disease or other multisystem disease states. Serial dilutions were necessary for samples exceeding the standard curve of the immunoassay (>4,000 pg/ml). The two highest values were observed in two mut0 patients that were subsequently referred for an orthotopic liver transplant. Liver pathology and electron microscopy findings showed advanced disease in these patients.

Figure 7B:
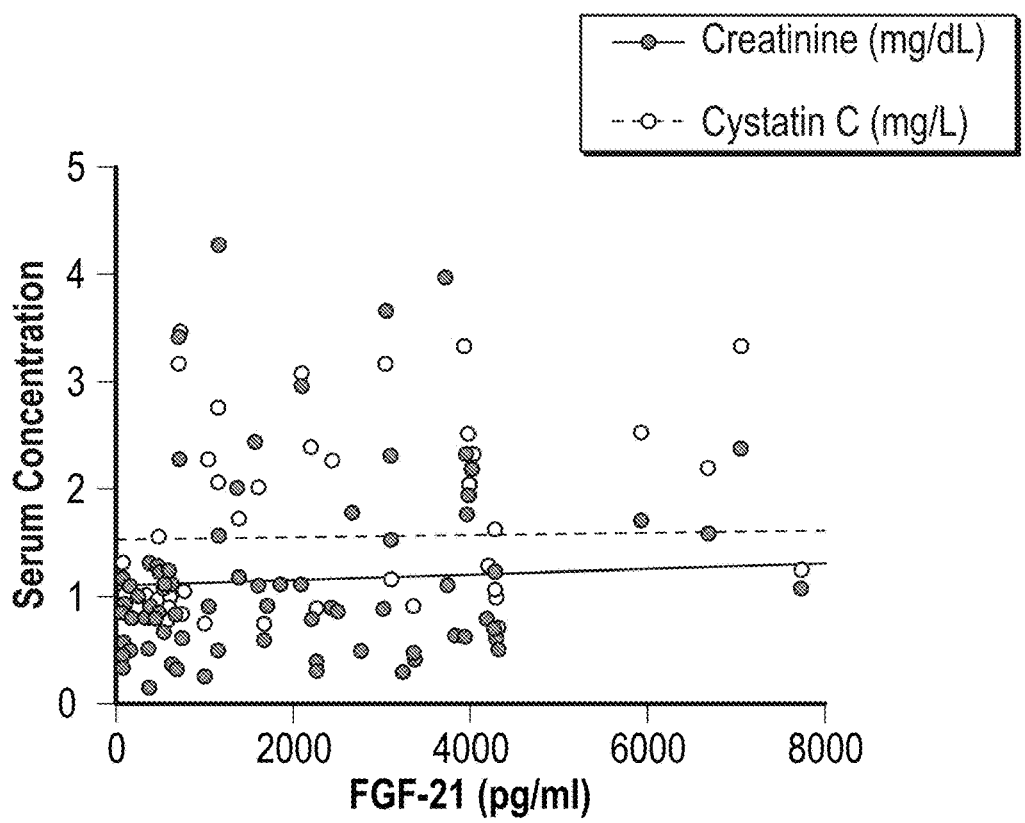

FGF21 correlated with disease subtype severity and markers of mitochondrial dysfunction, however, in contrast to serum methylmalonic acid, plasma FGF21 concentrations were not different between males and female patients, nor did they correlate significantly with age. Importantly, FGF21 levels were not affected by renal disease indices, including creatinine, cystatin-C (FIG. 7B) and therefore eGFR, suggesting FGF21 could represent a particularly useful biomarker to track liver mitochondrial damage and response to therapies independent of renal function.

Figure 7C:
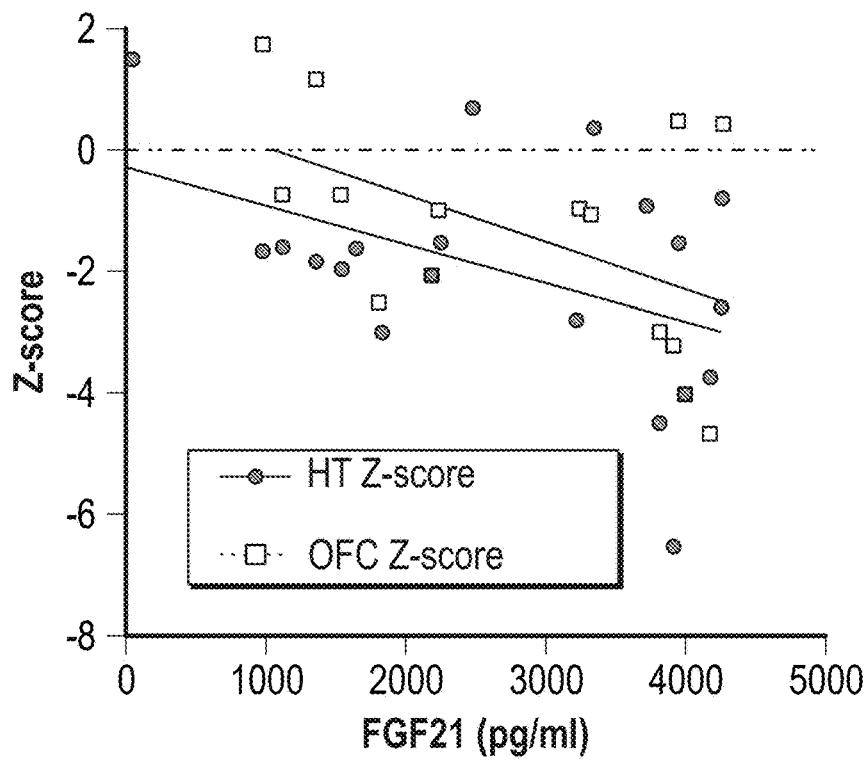
Figure 7D:
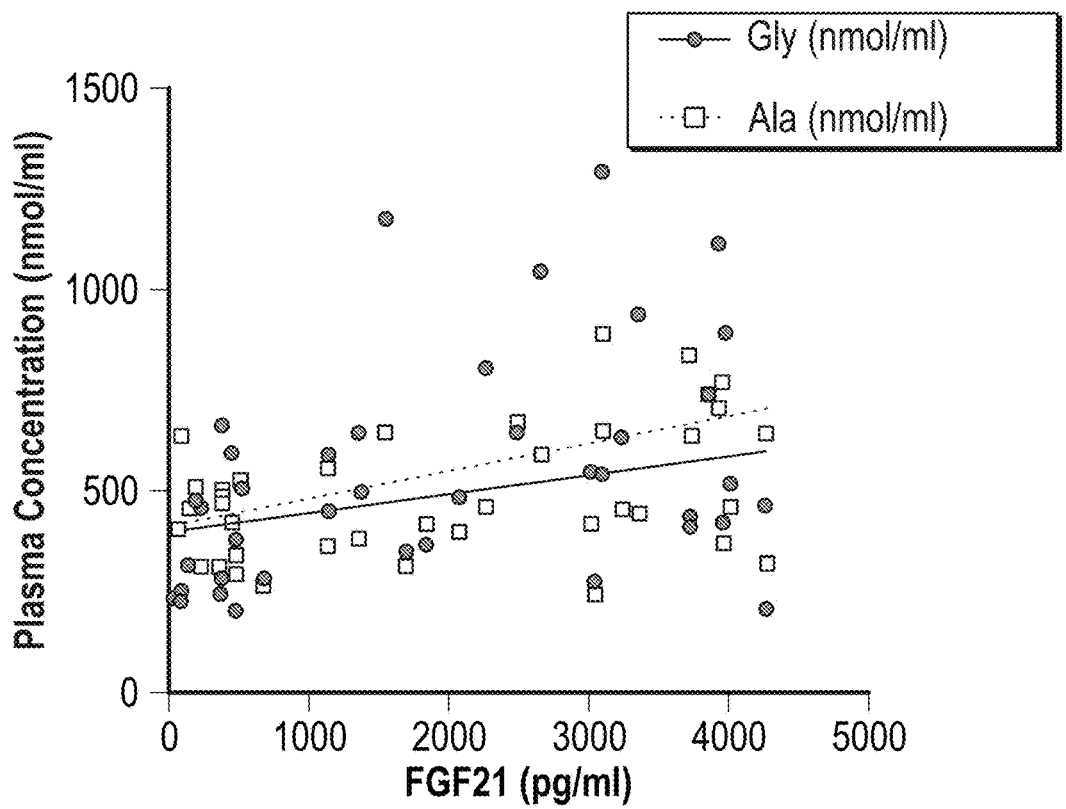
Figure 7E:
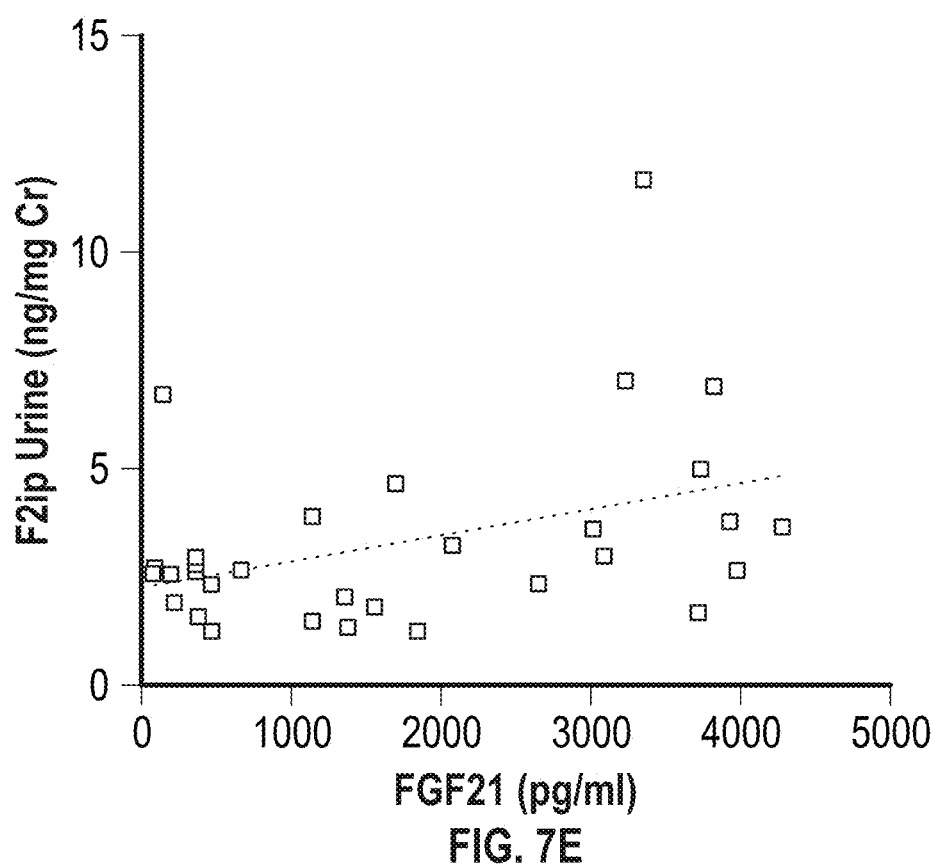

The relation to disease severity was further validated in patients with mut subtype, with correlations to other clinical outcomes and laboratory indices, like growth failure (height: r=−0.455, P=0.038, R$^2$=0.277 and head circumference Z-score: r=−0.505, P=0.05, R$^2$=0.255, FIG. 7C), plasma amino acids reflecting mitochondrial dysfunction (glycine: and alanine, FIG. 7D), and oxidative stress biomarkers such as urinary isoprostanes (FIG. 7E).

Histological studies comparing hepatic pathology between patients and mutant mice indicate that mice recapitulate the patient findings that the worst hepatic pathology had the highest measured levels of FGF21.

Figure 16A:
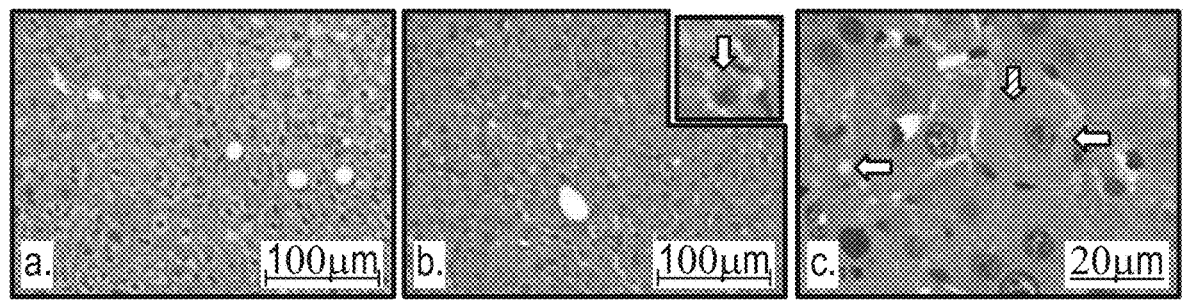
FIGS. 16A-B show hepatic pathological and ultrastructural changes in Mut$^{-/-}$; Tg$^{INS-MCK-Mut}$ mutant mice (FIG. 16A) and MMA patients (FIG. 16B).

FIG. 16A shows that hepatic pathology in mutant mice (panel b) was notable for swollen hepatocytes with increased eosinophilia and scattered Mallory bodies. Hepatocytes contained numerous cytoplasmic eosinophilic vacuoles consistent with megamitochondria (hashed arrow, FIG. 16A, panel c). Steatosis was observed in heterozygote animals reared on the same high fat and carbohydrate diet (FIG. 16A, panel a). No significant disruption of hepatic lobe architecture, fibrotic or cirrhotic changes were observed. Hematoxylin and eosin staining of liver sections from a 4-month old mouse are shown, scale bars: 20-100 μm).

Figure 16B:
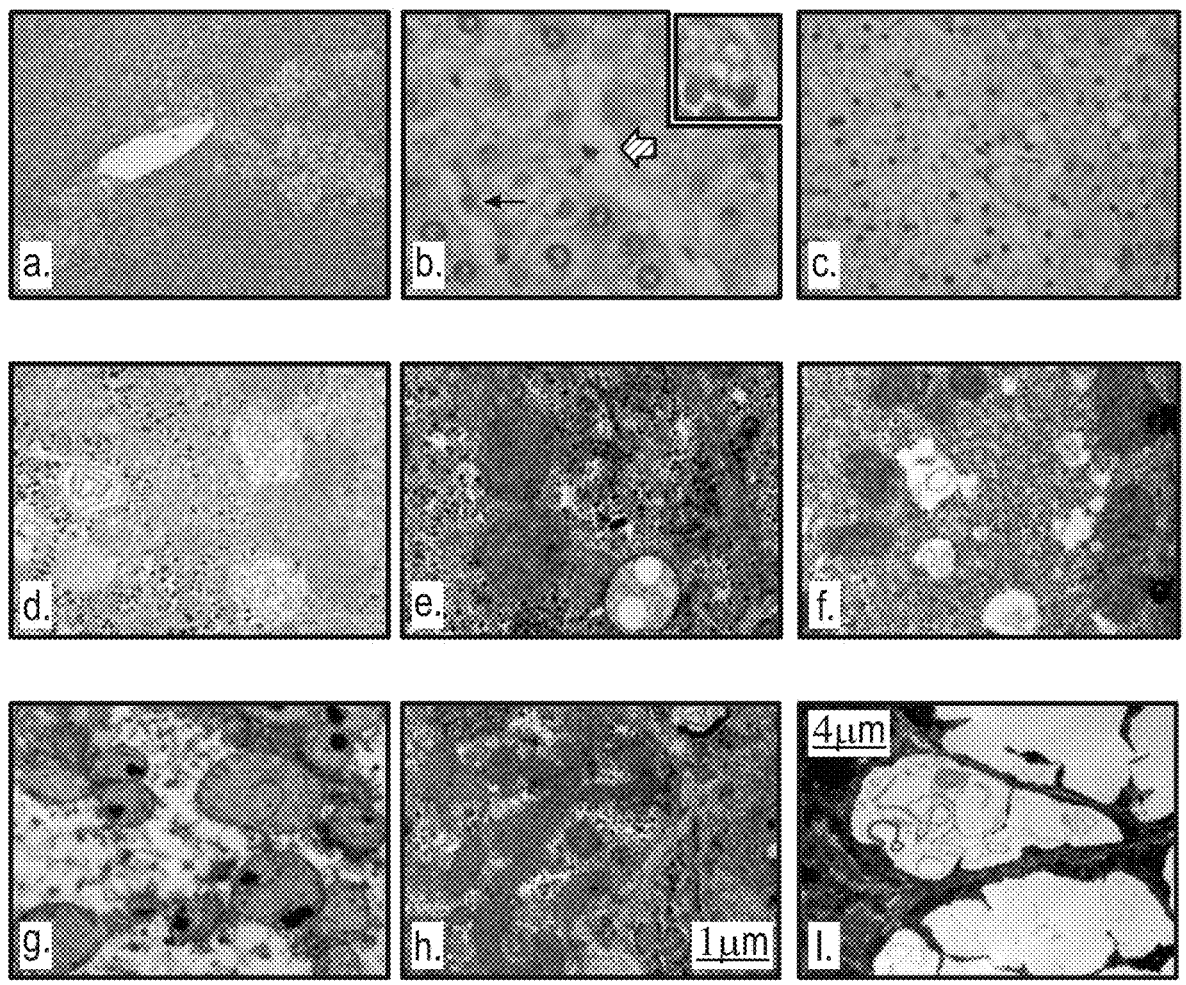

FIG. 16B shows that explanted livers from patients undergoing a liver transplantation displayed mostly macrovesicular periportal steatosis, lipid ladden stellate cells (FIG. 16B, panel b, hashed arrow) and occasional lipofuscin pigment granules (FIG. 16B inset, panel b). Mitochondria with a reduction or loss of matrix density, unusual size/shape and shortened, disorganized cristae are invariably present in liver pathology examinations by electron microscopy (FIG. 16B, panels d-h). In some patients, liver ultrastructure revealed complex cytoplasmic structures with inclusions of various size and density engulfed by membranes suggestive of autophagosomes (FIG. 16B, panel i).

Example 5: FGF21 Levels Reduce after LT or LKT in MMA

Figure 8A:
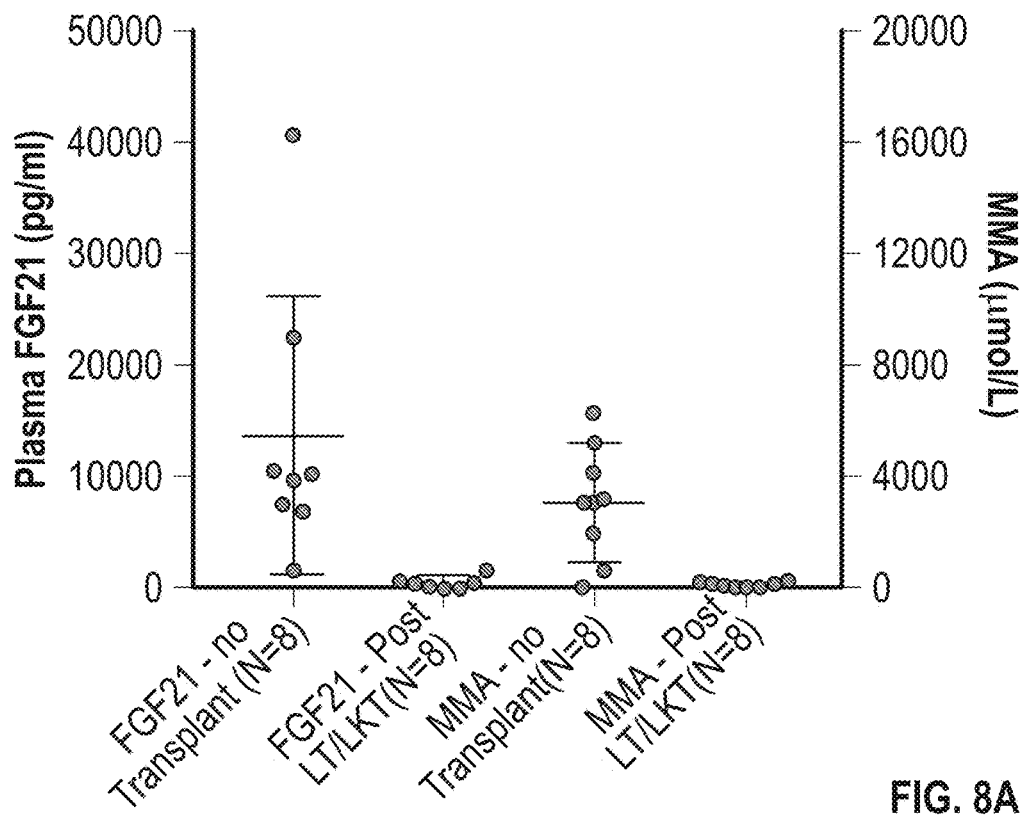
FIGS. 8A-B shows FGF21 levels in patients with MMA after combined liver kidney transplant (FIG. 8A) and (FIG. 8B) pre- and post-liver transplant with individual responses.
Figure 8B:
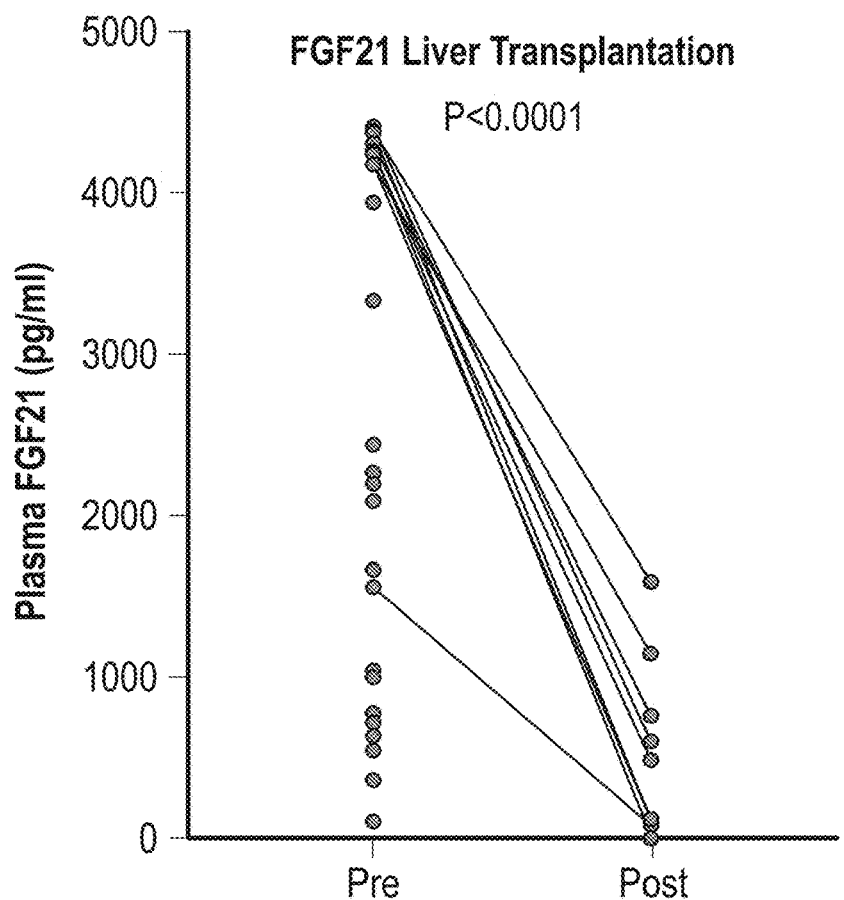

FGF21 levels were measured in a series of 8 patients with MUT MMA before and after liver or combined liver-kidney transplantation (FIG. 8A). In parallel, plasma methylmalonic acid, also designated MMA, was determined (FIG. 8B).

A subset of these MMA patients are individually presented (FIG. 8B) to illustrate the response of FGF21 to a liver directed intervention. In all patients, the levels of FGF21 show a drastic reduction after liver transplantation.

Example 6: FGF21 vs. Serum MMA (Mut Patients)

Figure 9A:
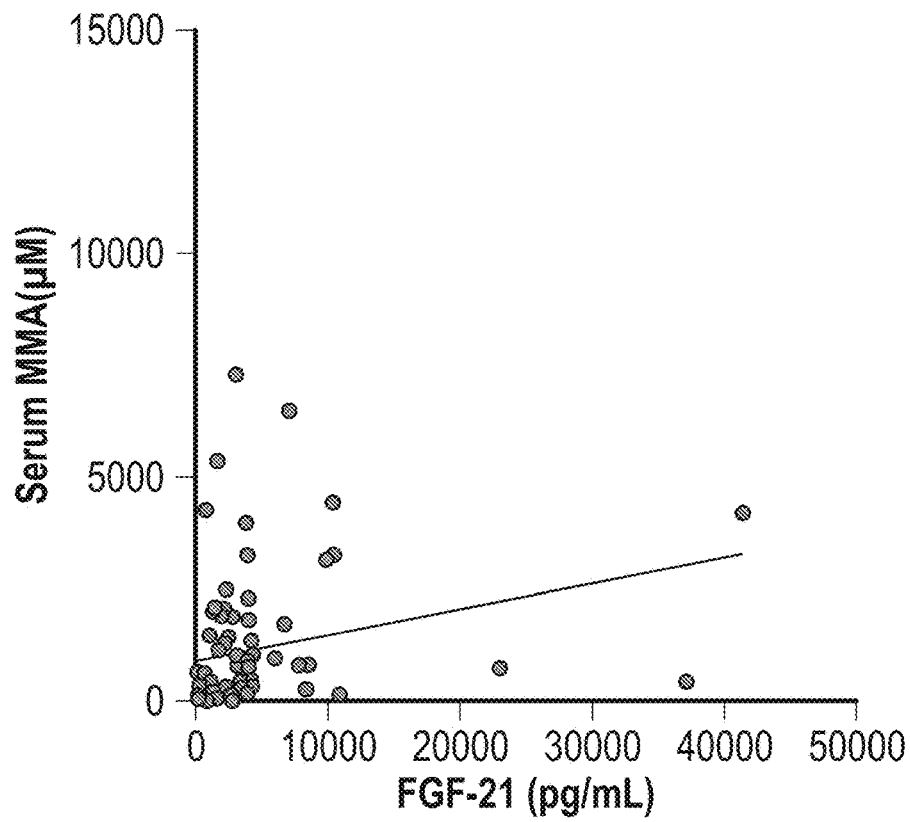
FIGS. 9A-B shows FGF21 vs. serum methylmalonic acid (MUT patients) (FIG. 9A) compared to canonical markers of renal disease such as creatinine and cystatin C (FIG. 9B).

FGF21 levels were measured in parallel with serum methylmalonic acid in a series of patients with MUT MMA. FIG. 9A presents a plot of the serum methylmalonic acid, also designated as MMA in this graph, compared to FGF21. There is a lack of correlation between the measurements.

Figure 9B:
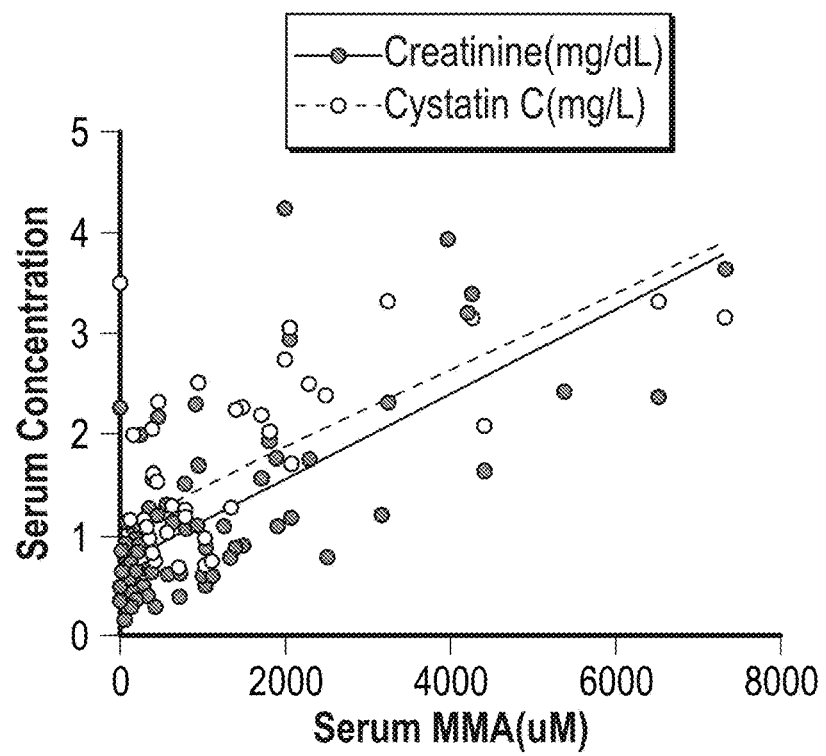

Because methylmalonic acid undergoes renal filtration, patients with MMA have increased concentrations of methylmalonic acid in the blood as renal function deteriorates. The relationships between cystatin C and creatinine, both markers of renal disease, are understood in MMA (reference Kruska et al) and exhibit a dependence in that as renal function declines, serum methylmalonic acid rises. A decline in renal function is also accompanied by a rise in cystatin C and creatinine. These relationships are depicted in FIG. 9B.

The fact that FGF21 does not correlate with methylmalonic acid levels, creatinine or cystatin C indicates that this biomarker is not affected by renal function. More specifically, the lack of interference of FGF21 levels by renal dysfunction suggests that the changes FGF21 levels can be used to assess a therapeutic response to a hepatic intervention in the setting of renal dysfunction and massive elevations of methylmalonic acid in patients with MMA.

Example 7: FGF21 in MUT AAV Gene Therapy Treated Mice

Another example of the utility of FGF21 to detect hepatic MUT function is in the settling of gene therapy where the vector transgene expresses MUT or activates MUT function.

An adenoviral associated vector (AAV) was prepared. This gene therapy vector was designed to express the MUT gene under the control of a liver-specific promoter and packaged with a serotype 8 capsid as is well understood by practitioners of the art.

Next, a cohort of 3-5 Mut$^{-/-}$, Tg$^{INS-MCK-Mut}$ mice were injected with $5 \times 10^{12}$ genome copies of either the AAV8 MUT vector using a retroorbital route of delivery.

Figure 10:
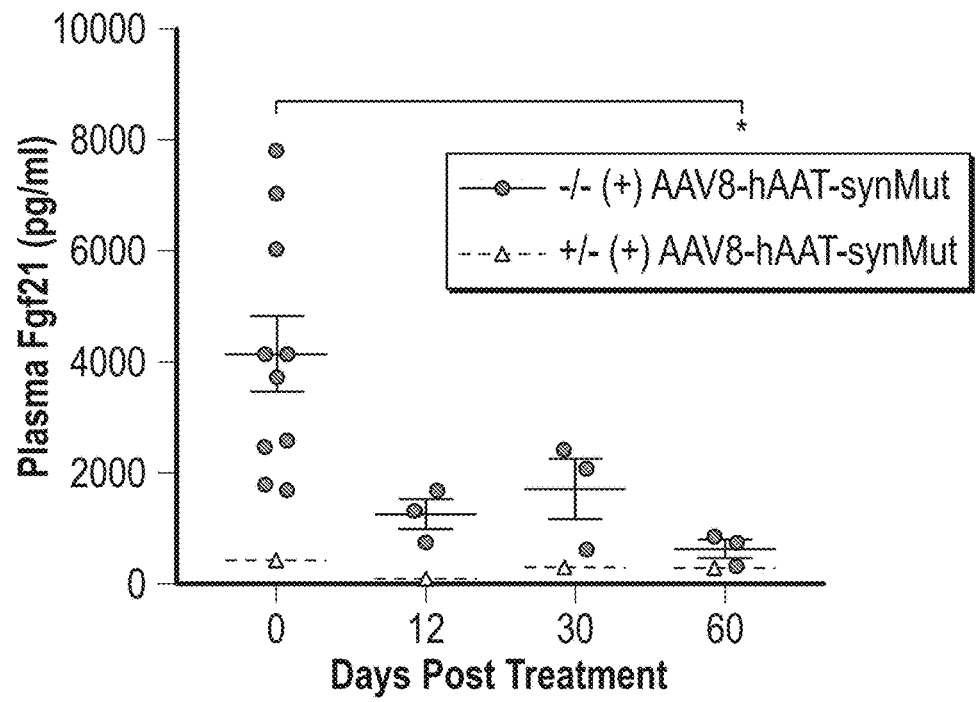
FIG. 10 shows FGF21 in MUT AAV gene therapy treated Mut$^{-/-}$; Tg$^{INS-MCK-Mut}$ mice. Each group contains 3-5 mice. Error bars surround +/— one standard deviation.

In the treated mice, FGF21 and plasma methylmalonic acid concentrations were measured at baseline, and again on days 15, 30 and 60. FIG. 10 presents the response to liver-directed AAV gene therapy in this MMA mouse model. The levels of FGF21 drop and nearly normalize in the treated Mut$^{-/-}$, Tg$^{INS-MCK-Mut}$ mice (−/− +) but not the untreated controls (+/− +). The FGF21 changes were noted to occur more rapidly and to a greater magnitude than the traditional plasma biomarker methylmalonic acid.

Figure 17A:
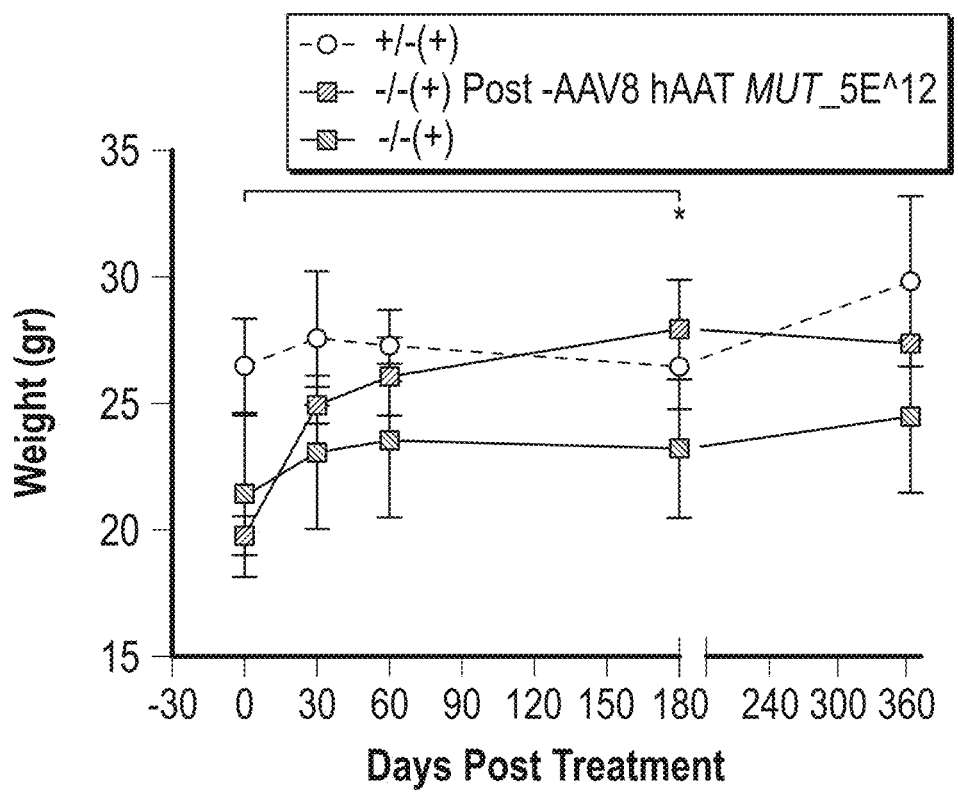
FIGS. 17A-B show hepatic Mut correction by transgenesis or AAV gene therapy confers weight gain in Mut$^{-/-}$; Tg$^{INS-MCK-Mut}$ mice, associated with a precipitous decrease in Fgf21.
Figure 17B:
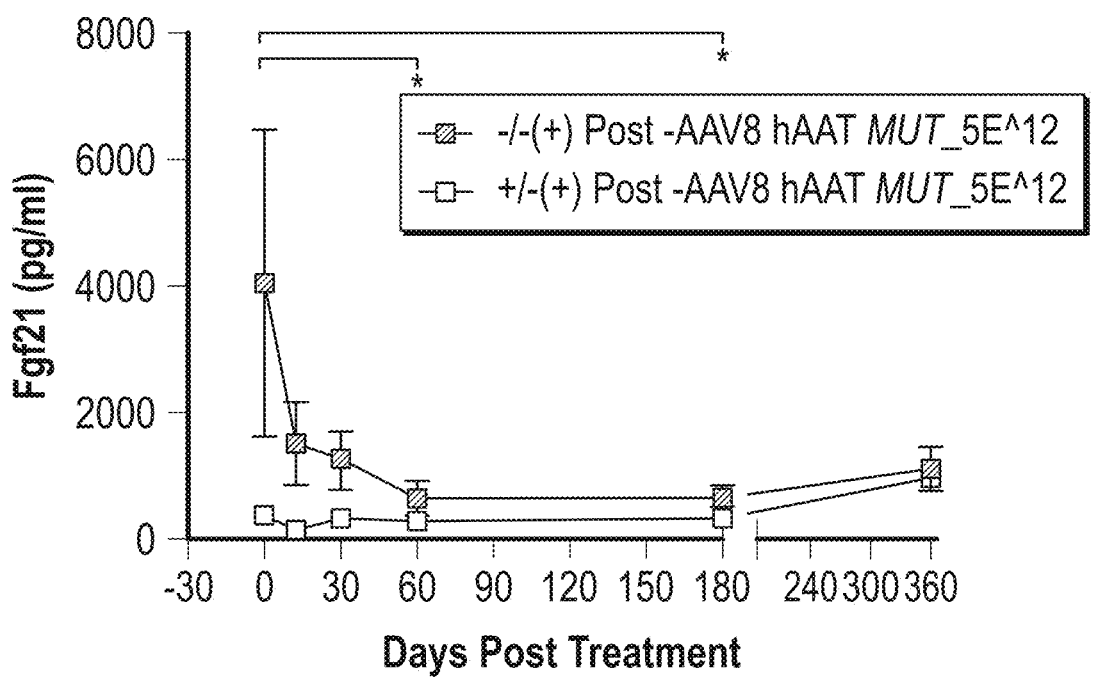

Significant and durable improvements in the clinical and biochemical parameters were observed in the AAV8 treated mice. These animals showed substantial weight gain FIG. 17A. Notably, the phenotypic correction of the Mut$^{-/-}$; Tg$^{INS-MCK-mut}$ mice was associated with a massive decrease in plasma Fgf21 concentrations (FIG. 17B) (90% decrease compared to baseline levels, from 4,084.6±823.4 pg/ml to 643.1±162.8 in 60 days and 1130.6±190.3 after one year).

This study shows that FGF21 is a sensitive biomarker of hepatic MUT function and can be used to measure the response of AAV gene therapy in MMA.

Example 8: GDF15 as a Hepatic Biomarker in MUT MMA

GDF15 has emerged as a marker of mitochondrial dysfunction in some studies. GDF15 might be useful to examine as a biomarker in MMA.

Figure 11:
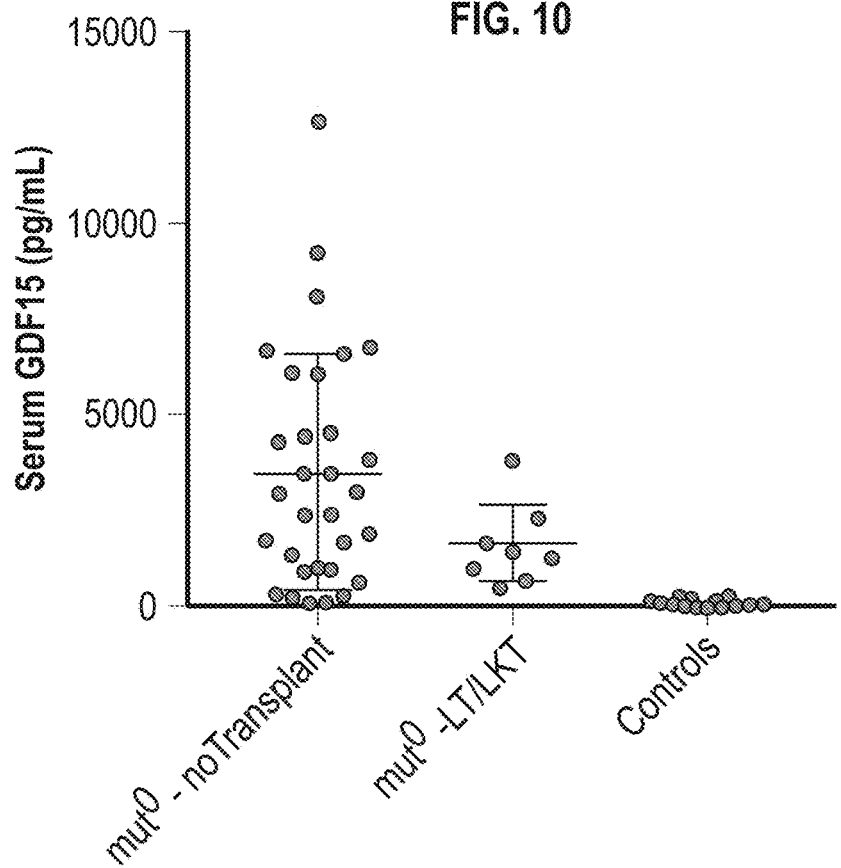
FIG. 11 shows serum GDF15 in MUT MMA patients, pre- and post-transplant, compared to controls.

GDF15 was measured using serum from patients with MMA, while those with MMA have received a liver or combined liver kidney transplant or unaffected controls, (FIG. 11) and the levels are diminished almost 3-fold after organ transplantation in patients with MMA.

Figure 12:
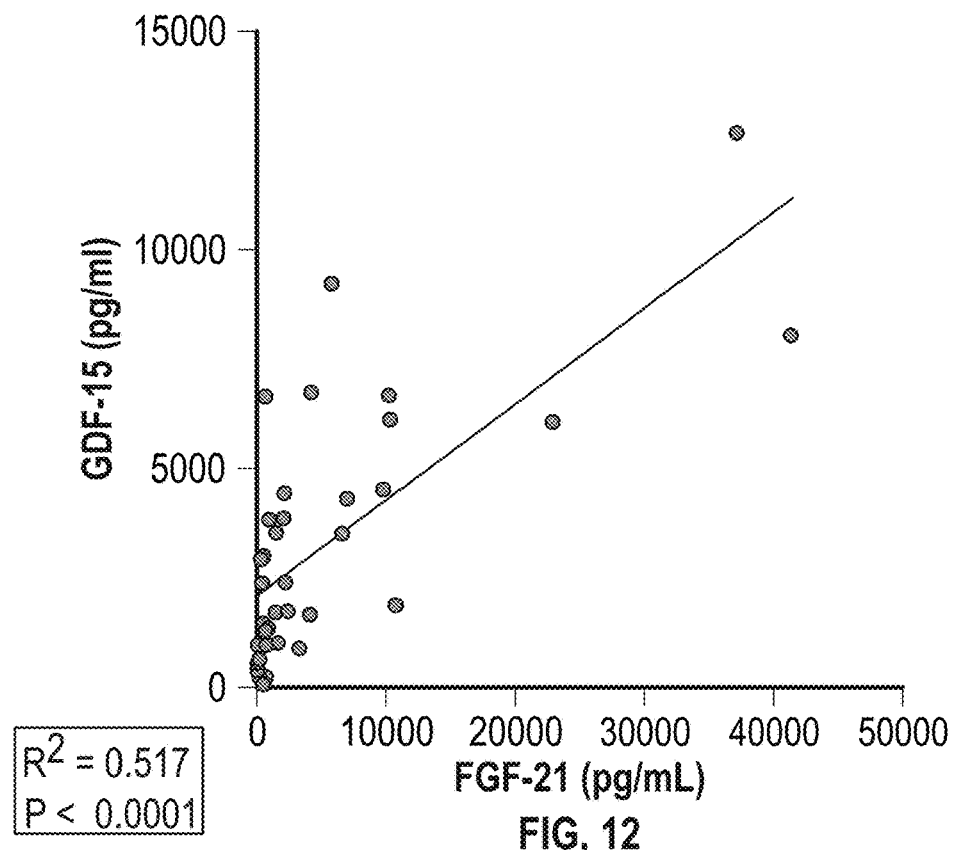
FIG. 12 shows FGF21 vs GDF15 levels in MMA patients.

FGF21 levels were compared to GDF15 in the same MMA patients (FIG. 12). There is a significant correlation between these markers, indicating that GDF15 is also a useful and predictive biomarker in patients with MMA.

Figure 13:
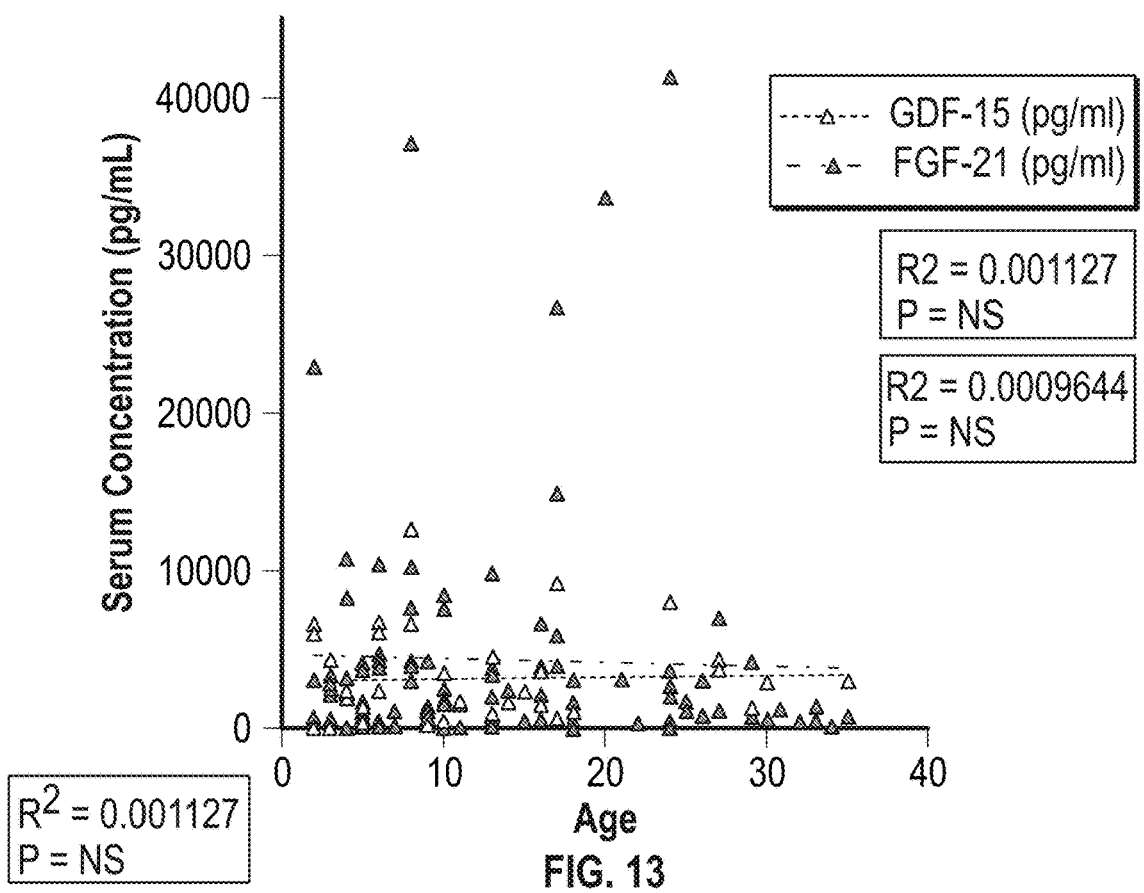
FIG. 13 shows FGF21, GDF15 levels vs. age.

To rule out a fortuitous age association, the effect of chronological age on the concentration of either marker, GDF15 or FGF21, was examined (FIG. 13). No association was present.

Example 9: Serum FGF21 in Propionic Acidemia

Propionic acidemia (PA) is caused by deficiency of the mitochondrial multimeric enzyme propionyl-CoA carboxylase that catalyzes the conversion of propionyl-CoA to D-methylmalonyl-CoA. The enzyme is composed of α- and β-subunits encoded by their respective genes, PCCA and PCCB. Deficient activity of propionyl-CoA carboxylase results in accumulation of propionic acid and propionyl-CoA related metabolites, which can be detected biochemically. Clinical manifestations of PA are often nonspecific and age of onset is variable.

The biochemical pathway where the PCC enzyme resides is linked to that of MUT and PA patients have clinical and biochemical similarities to patients with isolated MMA, including metabolic instability and hepatic mitochondrial dysfunction. The approach to dietary management is also similar, and many patients are treated by elective liver transplantation. (Shchelochkov et al. Genereviews, Propionic Acidemia)

Figure 14:
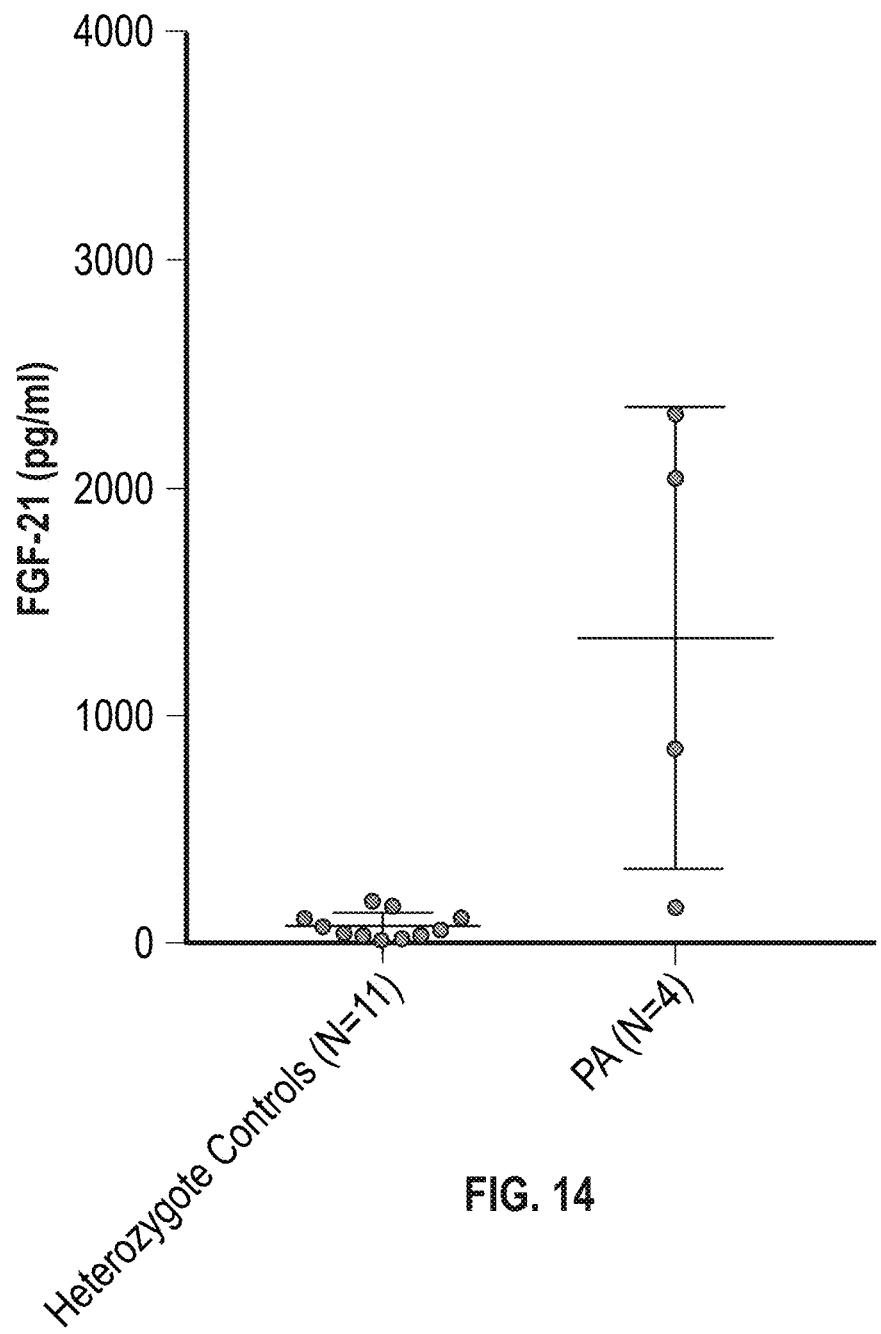
FIG. 14 shows serum FGF21 in propionic acidemia patients compared to heterozygous (parental) controls.

Therefore FGF21 in patients with PA and heterozygous parental controls was measured (FIG. 14). The clinically severe PA patients had much higher levels of FGF21 than the controls showing that FGF21 is a useful biomarker for PA.

Methylmalonic acidemia (MMA) caused by methylmalonyl-CoA mutase (MUT) deficiency, is characterized by recurrent episodes of life-threatening metabolic ketoacidosis and multiorgan complications. Studies in knockout mice (Mut−/−) and transplanted MMA patients suggested that extrahepatic organs, mainly the skeletal muscle, are a major source of circulating methylmalonic acid. To study the effects of restoring Mut activity in skeletal muscle on the hepatorenal phenotype of MMA, mice expressing the Mut gene under the control of the muscle creatine kinase promoter (Mut$^{-/-}$; Tg$^{INS-MCK-Mut}$) were generated. Although Mut expression in the muscle rescued Mut−/− mice from neonatal lethality, the Mut−/−; Tg$^{INS-MCK-Mut}$ mice exhibited severe growth failure, hepatic mitochondriopathy, renal dysfunction, and were resistant to obesity when fed a carbohydrate and lipid-enriched diet. A fasting challenge to model the metabolic decompensations seen in patients was used and the hepatic adaptations were probed using transcriptomics to identify candidate genes and pathways mediating the stress response. Among the most upregulated genes in the Mut−/−; TgINS-MCK-Mut mice was fibroblast growth factor—Fgf21, a key circulating metabolic regulator. After validation in mice, plasma FGF21 concentrations were measured in a large cohort of patients with different subtypes of isolated MMA (54 mut, 8 cblA and 5 cblB). FGF21 levels correlated with disease subtype severity (p=0.0001 between mut and cblA patients or controls) and showed an inverse relation to height Z-scores (r=−0.455, p=0.03). In contrast to serum methylmalonic acid concentrations, which are influenced by renal dysfunction, plasma FGF21 levels were not affected by renal function indices (creatinine, cystatin-C, eGFR), but did correlate with markers of secondary mitochondrial dysfunction, including plasma glycine, alanine and urinary isoprostanes (all p<0.05). In further support of the use of FGF21 as a biomarker of hepatic mitochondrial dysfunction in MMA, 9 patients before and after liver transplantation were studied, as well as Mut$^{-/-}$; Tg$^{INS-MCK-mut}$ mice treated with a liver-directed AAV8 MUT gene therapy vector. In both the patients and mice, a decrease in plasma FGF21 was accompanied by a restoration of 1-13C-propionate oxidation, reduced circulating metabolites and, in the mice, weight gain. The studies demonstrate the utility of 1-13C-propionate oxidation and plasma FGF21 as treatment biomarkers for MMA.

Example 10: FGF21 in Metabolic Crisis

Figure 18:
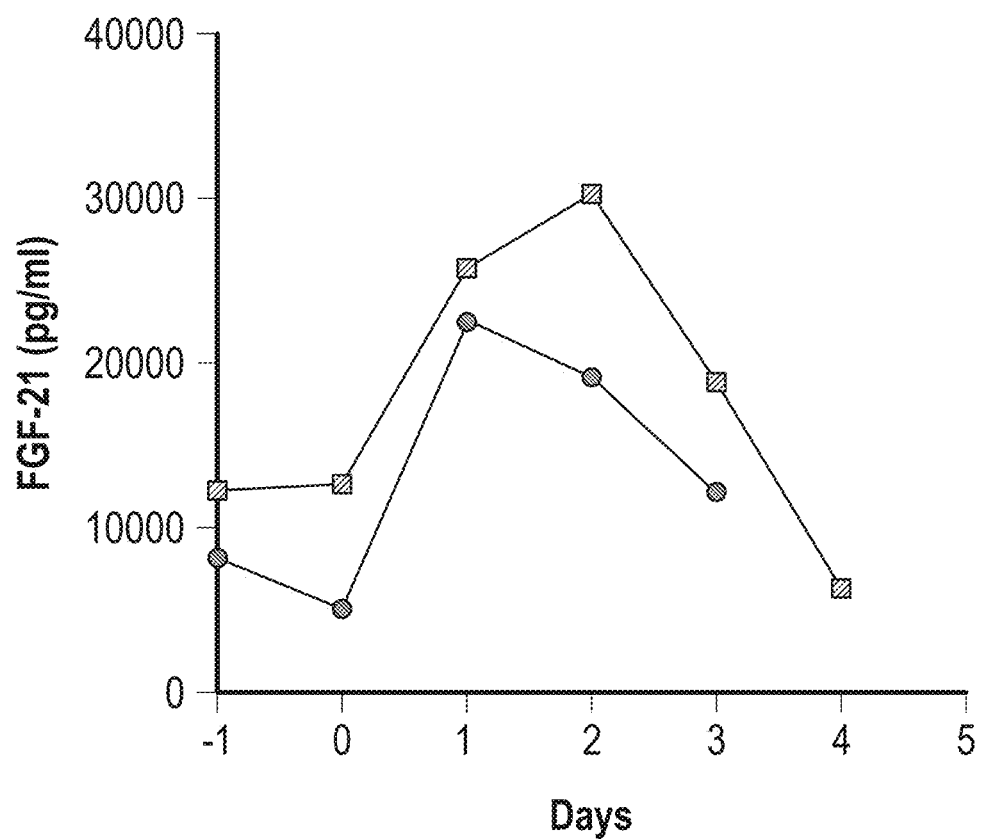
FIG. 18 shows serial FGF21 measurements before, during and after a metabolic crisis in two MMA siblings showed massive temporary increases in serum FGF21 concentrations that returned to pre-crisis levels upon recovery.

In two patients, FGF21 was measured before, during and after a metabolic crisis. FGF21 showed a significant upregulation during the episode of vomiting and metabolic ketoacidosis that required an inpatient admission for IV fluid replacement; concentrations returned to baseline upon discharge (FIG. 18).

TABLE 1

Pathway-enrichment analysis of hepatic differentially expressed genes in Mut$^{-/-}$; Tg$^{INS-MCK-Mut}$ mice

| Canonical pathway name | −log (P-value) |
| --- | --- |
| Immune responses: | |
| LPS/IL-1 Mediated Inhibition of RXR Function | 4.17E−05 |
| Acute Phase Response Signaling | 2.00E−04 |
| Complement System | 5.01E−03 |
| Metabolic processes: | |
| Tryptophan Metabolism | 7.94E−04 |
| Nitrogen Metabolism | 6.03E−03 |
| Metabolism of Xenobiotics by Cytochrome P450 | 6.03E−03 |
| Fatty Acid Metabolism | 7.08E−03 |
| Aryl Hydrocarbon Receptor Signaling | 9.77E−03 |
| Linoleic Acid Metabolism | 2.45E−02 |
| Androgen and Estrogen Metabolism | 2.63E−02 |
| Cell regulation & proliferation: | |
| Thyroid Cancer Signaling | 3.80E−04 |
| Endometrial Cancer Signaling | 1.23E−02 |
| Cell Cycle: G1/S Checkpoint Regulation | 1.41E−02 |
| Small Cell Lung Cancer Signaling | 2.19E−02 |
| Prolactin Signaling | 2.34E−02 |
| Acute Myeloid Leukemia Signaling | 2.57E−02 |
| Bladder Cancer Signaling | 3.39E−02 |
| Chronic Myeloid Leukemia Signaling | 3.72E−02 |

Abbreviations:
IL-1, interleukin-1,
LPS, lipopolysaccharide,
RXR, retinoid X receptor

TABLE 2

Hepatic differentially expressed genes in Mut$^{-/-}$; Tg$^{INS-MCK-Mut}$ mice. The fold change in mRNA expression between Mut$^{-/-}$; Tg$^{INS-MCK-Mut}$ mutant vs. heterozygous control mice is +/−2.5-fold or higher for most genes, in the fasting state. Bolded genes were validated by RT-PCR.

| Gene ID | Gene name description | Fold change |
| --- | --- | --- |
| Up-regulated in Mut$^{-/-}$; Tg$^{INS-MCK-Mut}$ | | |
| Cyp2b13 | cytochrome P450, family 2, subfamily b, polypeptide 13 | 17.2201 |
| Lepr | leptin receptor | 13.6931 |
| Cyp2b9 | cytochrome P450, family 2, subfamily b, polypeptide 9 | 11.3778 |
| Slc7a11 | solute carrier family 7 (cationic amino acid transporter, y+ system), member 11 | 11.1933 |
| Cyp2a22 | cytochrome P450, family 2, subfamily a, polypeptide 22 | 8.40305 |
| Asns | asparagine synthetase (glutamine-hydrolyzing) | 7.67448 |
| Aqp7 | aquaporin 7 | 6.14734 |
| Gstm3 | glutathione S-transferase, mu 3 | 5.76455 |
| Prss8 | protease, serine 8 (prostasin) | 5.13409 |
| Abcc4 | ATP-binding cassette, sub-family C (CFTR/MRP), member 4 | 4.62719 |
| Cd63 | CD63 antigen | 4.57022 |
| Socs2 | suppressor of cytokine signaling 2 | 4.51999 |
| Serpina7 | serine (or cysteine) peptidase inhibitor, clade A (alpha-1 antiproteinase, antitrypsin), member 7 | 4.24566 |
| Fmo3 | flavin containing monooxygenase 3 | 4.24517 |
| Fabp5 | fatty acid binding protein 5, epidermal | 4.16172 |
| Myc | myelocytomatosis oncogene | 3.96234 |
| Ly6d | lymphocyte antigen 6 complex, locus D | 3.91013 |
| Psat1 | phosphoserine aminotransferase 1 | 3.90115 |
| Itga6 | integrin alpha 6 | 3.87572 |
| Nipal1 | NIPA-like domain containing 1 | 3.71795 |
| Prrg4 | proline rich Gla (G-carboxyglutamic acid) 4 (transmembrane) | 3.70926 |
| Slc35f2 | solute carrier family 35, member F2 | 3.68109 |
| Ucp2 | uncoupling protein 2 (mitochondrial, proton carrier) | 3.61009 |
| Fabp5 | fatty acid binding protein 5, epidermal | 3.58465 |
| Nupr1 | nuclear protein transcription regulator 1 | 3.56982 |
| Acot2 | acyl-CoA thioesterase 2 | 3.56934 |
| Usp18 | ubiquitin specific peptidase 18 | 3.42937 |
| Ccnd1 | cyclin D1 | 3.40784 |
| Tuba8 | tubulin, alpha 8 | 3.32778 |
| Car2 | carbonic anhydrase 2 | 3.31722 |
| Slc22a26 | solute carrier family 22 (organic cation transporter), member 26 | 3.31718 |
| Pdk4 | pyruvate dehydrogenase kinase, isoenzyme 4 | 3.09495 |
| Cpt1b | carnitine palmitoyltransferase 1b, muscle | 3.08727 |
| Ntf3 | neurotrophin 3 | 3.05671 |
| Abcd2 | ATP-binding cassette, sub-family D (ALD), member 2 | 3.04059 |
| Hmox1 | heme oxygenase 1 | 2.99425 |
| Sqle | squalene epoxidase | 2.96694 |
| Slc22a27 | solute carrier family 22, member 27 | 2.92662 |
| Rragd | Ras-related GTP binding D | 2.89877 |
| S100a11 | S100 calcium binding protein A11 | 2.84718 |
| Cyp11b1 | cytochrome P450, family 11, subfamily b, polypeptide 1 | 2.81364 |
| Vldlr | very low density lipoprotein receptor | 2.81125 |
| Cln6 | ceroid-lipofuscinosis, neuronal 6 | 2.73666 |
| App | amyloid beta (A4) precursor protein | 2.69394 |
| Dhrs9 | dehydrogenase/reductase (SDR family) member 9 | 2.68222 |
| Pfkp | phosphofructokinase, platelet | 2.66094 |
| Acsl4 | acyl-CoA synthetase long-chain family member 4 | 2.65086 |
| Fabp3 | fatty acid binding protein 3, muscle and heart | 2.63105 |
| Sgk1 | serum/glucocorticoid regulated kinase 1 | 2.62696 |
| Renbp | renin binding protein | 2.59198 |
| Adra2a | adrenergic receptor, alpha 2a | 2.54969 |
| Morc4 | microrchidia 4 | 2.50036 |
| Fgf21 | Fibroblast growth factor 21 | 1.519 |
| Down-regulated in Mut$^{-/-}$; Tg$^{INS-MCK-Mut}$ | | |
| Elovl3 | elongation of very long chain fatty acids (FEN1/Elo2, SUR4/Elo3, yeast)-like 3 | −13.414 |
| Orm1 | orosomucoid 1 | −12.533 |
| Nnmt | nicotinamide N-methyltransferase | −10.919 |
| Slco1a1 | solute carrier organic anion transporter family, member 1a1 | −9.778 |
| Obp2a | odorant binding protein 2A (Lcn13) | −8.909 |
| Slc3a1 | solute carrier family 3, member 1 | −8.471 |
| C9 | complement component 9 | −7.428 |
| Pigr | polymeric immunoglobulin receptor | −6.746 |
| Orm3 | orosomucoid 3 | −6.603 |

TABLE 2-continued

Hepatic differentially expressed genes in Mut$^{-/-}$; Tg$^{INS-MCK-Mut}$ mice. The fold change in mRNA expression between Mut$^{-/-}$; Tg$^{INS-MCK-Mut}$ mutant vs. heterozygous control mice is +/−2.5-fold or higher for most genes, in the fasting state. Bolded genes were validated by RT-PCR.

| Gene ID | Gene name description | Fold change |
|---|---|---|
| Saa2 | serum amyloid A 2 | −6.538 |
| Cyp7b1 | cytochrome P450, family 7, subfamily b, polypeptide 1 | −4.891 |
| Ces3b | carboxylesterase 3B | −4.631 |
| Hsd3b2 | hydroxy-delta-5-steroid dehydrogenase, 3 beta- and steroid delta-isomerase 2 | −3.886 |
| Ido2 | indoleamine 2,3-dioxygenase 2 | −3.459 |
| Mut | methylmalonyl-Coenzyme A mutase | −3.448 |
| Susd4 | sushi domain containing 4 | −3.285 |
| Saa4 | serum amyloid A 4 | −3.257 |
| Mup3 | major urinary protein 3 | −3.209 |
| Slc8a1 | solute carrier family 8 (sodium/calcium exchanger), member 1 | −3.193 |
| C6 | complement component 6 | −3.113 |
| Sucnr1 | succinate receptor 1 | −2.997 |
| Scnn1a | sodium channel, nonvoltage-gated 1 alpha | −2.989 |
| Alas2 | aminolevulinic acid synthase, erythroid | −2.893 |
| P2ry4 | pyrimidinergic receptor P2Y, G-protein coupled, 4 | −2.842 |
| Car1 | carbonic anhydrase 1 | −2.820 |
| Abat | 4-aminobutyrate aminotransferase | −2.788 |
| Acnat2 | acyl-coenzyme A amino acid N-acyltransferase 2 | −2.788 |
| Nox4 | NADPH oxidase 4 | −2.769 |
| Arrdc3 | arrestin domain containing 3 | −2.762 |
| Mbl2 | mannose-binding lectin (protein C) 2 | −2.747 |
| Fam55b | neurexophilin and PC-esterase domain family, member 2 | −2.710 |
| Cyp2c54 | cytochrome P450, family 2, subfamily c, polypeptide 54 | −2.651 |
| Nr0b2 | nuclear receptor subfamily 0 group B member 2 | −2.617 |
| Hsd3b5 | hydroxy-delta-5-steroid dehydrogenase, 3 beta- and steroid delta-isomerase 5 | −2.614 |
| Fitm1 | fat storage-inducing transmembrane protein 1 | −2.614 |
| Cyp2d9 | cytochrome P450, family 2, subfamily d, polypeptide 9 | −2.584 |
| Cyp2u1 | cytochrome P450, family 2, subfamily u, polypeptide 1 | −2.561 |
| Srd5a1 | steroid 5 alpha-reductase 1 | −2.554 |
| Bdh2 | 3-hydroxybutyrate dehydrogenase, type 2 | −2.529 |
| Mfsd2a | major facilitator superfamily domain containing 2A | −2.528 |
| Hsd3b3 | hydroxy-delta-5-steroid dehydrogenase, 3 beta- and steroid delta-isomerase 3 | −2.501 |

TABLE 3

Hepatic differentially expressed genes in Mut$^{-/-}$; Tg$^{INS-MCK-Mut}$ mice. The fold change in mRNA expression between Mut$^{-/-}$; Tg$^{INS-MCK-Mut}$ mutant vs. heterozygous control mice is +/−2.5-fold or higher, at baseline. Bolded genes were validated by RT-PCR.

| Gene ID | Gene name description | Fold change |
|---|---|---|
| Up-regulated in Mut$^{-/-}$; Tg$^{INS-MCK-Mut}$ | | |
| Cyp2b13 | cytochrome P450, family 2, subfamily b, polypeptide 13 | 22.7371 |
| Cyp2b9 | cytochrome P450, family 2, subfamily b, polypeptide 9 | 15.4925 |
| Cyp2a22 | cytochrome P450, family 2, subfamily a, polypeptide 22 | 12.5795 |
| Slc7a11 | solute carrier family 7 (cationic amino acid transporter, y+ system), member 11 | 10.9933 |
| Igfbp1 | insulin-like growth factor binding protein 1 | 7.0268 |
| Asns | asparagine synthetase (glutamine-hydrolyzing) | 6.16761 |
| Lepr | leptin receptor | 5.87584 |
| Mt1 | metallothionein 1 | 5.87584 |
| Mt2 | metallothionein 2 | 5.79545 |
| Fmo3 | flavin containing monooxygenase 3 | 5.30067 |
| Pdk4 | pyruvate dehydrogenase kinase, isoenzyme 4 | 4.6963 |
| Abcd2 | ATP-binding cassette, sub-family D (ALD), member 2 | 4.68813 |
| Abcc4 | ATP-binding cassette, sub-family C (CFTR/MRP), member 4 | 4.44352 |
| Aqp7 | aquaporin 7 | 4.36222 |
| Cdkn1a | cyclin-dependent kinase inhibitor 1A (P21) | 4.30294 |
| Lcn2 | lipocalin 2 | 4.03863 |
| Slc16a5 | solute carrier family 16 member 5 | 4.00274 |
| Cyp39a1 | cytochrome P450, family 39, subfamily a, polypeptide 1 | 3.98547 |
| Acot2 | acyl-CoA thioesterase 2 | 3.89254 |
| Serpina7 | serine (or cysteine) peptidase inhibitor, clade A | 3.83673 |
| Gstm3 | glutathione S-transferase, mu 3 | 3.79305 |
| Fmo2 | flavin containing monooxygenase 2 | 3.76811 |
| Ccnd1 | cyclin D1 | 3.64218 |
| Atp6v0d2 | ATPase, H+ transporting, lysosomal V0 subunit D2 | 3.61714 |
| Tuba8 | tubulin, alpha 8 | 3.53428 |
| Itga6 | integrin alpha 6 | 3.50537 |
| Prss8 | protease, serine, 8 (prostasin) | 3.49417 |
| Ucp2 | uncoupling protein 2 (mitochondrial, proton carrier) | 3.47547 |
| Agpat9 | 1-acylglycerol-3-phosphate O-acyltransferase 9 | 3.41908 |
| Nipal1 | NIPA-like domain containing 1 | 3.38576 |
| Prrg4 | proline rich Gla (G-carboxyglutamic acid) 4 | 3.26839 |
| *Gadd45b* | growth arrest and DNA-damage-inducible 45 beta | 3.20671 |
| Fgf21 | fibroblast growth factor 21 | 3.20183 |
| Vldlr | very low density lipoprotein receptor | 3.16008 |
| Rragd | Ras-related GTP binding D | 3.13529 |
| Slc35f2 | solute carrier family 35, member F2 | 3.09305 |
| Down-regulated in Mut$^{-/-}$; Tg$^{INS-MCK-Mut}$ | | |
| Hsd3b5 | hydroxy-delta-5-steroid dehydrogenase, 3 beta | −38.006 |
| Serpina4-ps1 | serine (or cysteine) peptidase inhibitor, clade A, member 4, pseudogene 1 | −33.6911 |
| Elovl3 | elongation of very long chain fatty acids (FEN1/Elo2, SUR4/Elo3, yeast)-like 3 | −17.9672 |
| Lcn13 | lipocalin 13 | −13.4011 |
| Orm1 | orosomucoid 1 | −8.20892 |
| Slco1a1 | solute carrier organic anion transporter family, member | −7.99863 |
| Cyp7b1 | cytochrome P450, family 7, subfamily b, polypeptide 1 | −6.79284 |
| Mup21 | major urinary protein 21 | −6.24468 |
| Slc10a2 | solute carrier family 10, member 2 | −5.07917 |
| C9 | complement component 9 | −4.83417 |
| Gm4738 | predicted gene 4738 | −4.69531 |
| Slc3a1 | solute carrier family 3, member 1 | −4.55954 |
| Cyp2u1 | cytochrome P450, family 2, subfamily u, polypeptide 1 | −4.52754 |
| Pigr | polymeric immunoglobulin receptor | −4.35133 |
| Dpy19l3 | dpy-19-like 3 (C. elegans) | −4.32998 |
| Ust | uronyl-2-sulfotransferase | −3.96261 |
| Nnmt | nicotinamide N-methyltransferase | −3.93023 |
| c | predicted gene 4956 | −3.91234 |
| Hsd3b2 | hydroxy-delta-5-steroid dehydrogenase, 3 beta- and steroid delta-isomerase 2 | −3.87254 |
| Cyp8b1 | cytochrome P450, family 8, subfamily b, polypeptide 1 | −3.83379 |

TABLE 3-continued

Hepatic differentially expressed genes in Mut$^{-/-}$; Tg$^{INS-MCK-Mut}$ mice. The fold change in mRNA expression between Mut$^{-/-}$; Tg$^{INS-MCK-Mut}$ mutant vs. heterozygous control mice is +/−2.5-fold or higher, at baseline. Bolded genes were validated by RT-PCR.

| Gene ID | Gene name description | Fold change |
| --- | --- | --- |
| C6 | complement component 6 | −3.66232 |
| Srd5a1 | steroid 5 alpha-reductase 1 | −3.63131 |
| Mut | methylmalonyl-Coenzyme A mutase | −3.40601 |
| Gm11437 | predicted gene 11437 | −3.3375 |
| Adh6-ps1 | alcohol dehydrogenase 6 (class V), pseudogene 1 | −3.27739 |
| Agxt2l1 | alanine-glyoxylate aminotransferase 2-like 1 | −3.03955 |
| Sucnr1 | succinate receptor 1 | −3.01301 |

What is claimed is:

1. A method for determining the efficacy of a treatment for an organic acidemia in a subject, the method comprising:
   detecting the level of a biomarker or biomarkers in a biological sample from the subject prior to the treatment, wherein the biomarker or biomarkers is a fibroblast growth factor 21 (FGF21) gene expression product or a growth differentiation factor 15 (GDF15) gene expression product, or both;
   administering the treatment to the subject to improve compromised hepatic enzyme activity associated with the organic acidemia;
   detecting the level of the biomarker or biomarkers in a biological sample from the subject after the treatment;
   wherein a decrease in the level of the biomarker or biomarkers after the treatment compared to the level of the biomarker or biomarkers prior to the treatment indicates efficacy of the treatment; and
   altering or continuing the treatment based on the level after treatment compared to the level before treatment.

2. The method of claim 1, wherein the biomarker is a FGF21 gene expression product.

3. The method of claim 1, wherein the biomarker is a GDF15 gene expression product.

4. The method of claim 1, wherein the biomarker or biomarkers comprises both a FGF21 gene expression product and a GDF15 gene expression product.

5. The method of claim 1, wherein the biomarker is a protein.

6. The method of claim 1, wherein the biomarker is detected at the nucleic acid level.

7. The method of claim 1, wherein the biological sample is a serum.

8. The method of claim 1, wherein the biological sample is a plasma sample.

9. The method of claim 1, wherein the treatment is a liver-directed treatment.

10. The method of claim 1, wherein the treatment comprises administering a liver-directed gene transfer vector to the subject.

11. The method of claim 1, wherein the treatment is selected from the group consisting of gene therapy, mRNA therapy, cell therapy, small molecule, enzyme specific chaperonins, engineered microbes/microbiome, enzyme replacement therapy, and genome editing therapies.

12. The method of claim 1, wherein the organic acidemia is selected from the group consisting of all forms of methylmalonic acidemia (MMA), all forms of propionic acidemia (PA), isovaleric acidemia, glutaric aciduria type 1 (GA1), beta-ketothiolase deficiency (BKT), 3-methylcrotonyl-CoA carboxylase deficiency (3-MCC), 3-hydroxy-3-methylglutaryl-CoA lyase deficiency (HMG), 3-Methylglutaconic acidemia or 3-Methylglutaconyl-CoA Hydratase Deficiency (MGA), D-2 Hydroxyglutaric Aciduria (D2-HGA), Isobutyryl-CoA Dehydrogenase Deficiency 3-Hydroxyisobutyric aciduria (ICBD), L-2-Hydroxy-glutaricaciduria (L2HGA), Malonyl-CoA Decarboxylase Deficiency aka Malonic Acidemia (MA), Multiple carboxylase deficiency (MCD, holocarboxylase synthetase), and 3-Hydroxyisobutyryl-CoA Hydrolase Deficiency (HIBCH).

13. The method of claim 1, wherein the organic acidemia is methylmalonic acidemia or propionic acidemia.

14. The method of claim 1, wherein the organic acidemia is a disorder of propionate metabolism or a cobalamin metabolic and transport disorder causing MUT deficiency.

15. The method of claim 14, wherein the disorder of propionate metabolism is caused by isolated methylmalonyl-CoA mutase (MUT) deficiency, methylmalonic aciduria type A protein (MMAA), methylmalonic aciduria type B protein (MMAB), methylmalonic aciduria and homocystinuria type D protein (MMADHC), or complementation group cblA (cblA), complementation group cblB (cblB), complementation group cblD (cblD) variant 2 classes of methylmalonic acidemia (MMA).

16. The method of claim 14, wherein the cobalamin metabolic and transport disorders is selected from the group consisting of methylmalonic aciduria and homocystinuria type C protein (MMACHC), methylmalonic aciduria and homocystinuria type D protein (MMADHC), lysosomal cobalamin transporter (LMBRD1), ATP-binding cassette sub-family D member 4 (ABCD4), transcobalamin 2 (TC2), cluster of differentiation 320 (CD320), amnionless (AMN), complementation group cblC (cblC), complementation group cblD (cblD), complementation group cblF (cblF), complementation group cblJ (cblJ), and Imerslund-Graesbeck forms of combined methylmalonic acidemia hyperhomocysteinemia.

17. The method of claim 1, wherein the treatment is liver transplantation or combined liver and kidney transplantation.

18. A method of treating a subject for an organic acidemia, the method comprising:
   detecting the level of a biomarker or biomarkers in a biological sample from the subject prior to treatment, wherein the biomarker is a fibroblast growth factor 21 (FGF21) gene expression product or a growth differentiation factor 15 (GDF15) gene expression product, or both;
   administering a treatment to the subject to improve compromised hepatic enzyme activity associated with the organic acidemia;
   detecting the level of the biomarker or biomarkers in a biological sample from the subject after the treatment; and
   altering or continuing the treatment based on the level after treatment compared to the level before treatment.

19. A method for improving hepatic enzyme activity in a subject having an organic acidemia, the method comprising:
   detecting the level of a biomarker or biomarkers in a biological sample from the subject prior to treatment, wherein the biomarker or biomarkers is a fibroblast growth factor 21 (FGF21) gene expression product or a growth differentiation factor 15 (GDF15) gene expression product, or both;
   administering a treatment to the subject to improve compromised hepatic enzyme activity associated with the organic acidemia;
   detecting the level of the biomarker or biomarkers in a biological sample from the subject after the treatment; and
   altering or continuing the treatment based on the level after treatment compared to the level before treatment.

20. The method of claim 19, where in the enzyme is selected from the group consisting of methylmalonyl-CoA mutase, propionyl CoA carboxylase, isovaleryl-CoA dehydrogenase, Glutaryl CoA Dehydrogenase, beta-ketothiolase, 3-methylcrotonyl-CoA carboxylase, 3-hydroxy-3-methylglutaryl-CoA lyase, 3-Methylglutaconyl-CoA Hydratase, Isobutyryl-CoA Dehydrogenase, Malonyl-CoA Decarboxylase, Multiple carboxylase, and 3-Hydroxyisobutyryl-CoA Hydrolase.

* * * * *